US010398770B2

(12) United States Patent
Sączyńska et al.

(10) Patent No.: US 10,398,770 B2
(45) Date of Patent: Sep. 3, 2019

(54) INFLUENZA VIRUS HEMAGGLUTININ PROTEIN AS A VACCINE ANTIGEN

(71) Applicant: INSTYTUT BIOTECHNOLOGII I ANTY-BIOTYKÓW, Warsaw (PL)

(72) Inventors: Violetta Sączyńska, Warsaw (PL); Agnieszka Romanik, Ostrów Mazowiecka (PL); Katarzyna Florys, Iwaniska (PL); Violetta Cecuda-Adamczewska, Warsaw (PL); Malgorzata Kęsik-Brodacka, Warsaw (PL); Grażyna Plucienniczak, Warsaw (PL); Andrzej Plucienniczak, Warsaw (PL); Piotr Borowicz, Warsaw (PL); Natalia Lukasiewicz, Warsaw (PL); Iwona Sokolowska, Warsaw (PL); Diana Mikiewicz, Warsaw (PL); Agnieszka Sobolewska, Warsaw (PL); Piotr Baran, Warsaw (PL); Józef Kapusta, Swarzedz (PL); Michal Odrowąż-Sypniewski, Warsaw (PL); Anna Bierczyńska-Krzysik, Warsaw (PL); Zenon Minta, Pulawy (PL); Krzysztof Śmietanka, Pulawy (PL); Monika Olszewska, Chojnów (PL); Boguslaw Szewczyk, Gdańsk (PL)

(73) Assignee: INSTYTUT BIOTECHNOLOGII I ANTY-BIOTYKOW, Warsaw (PL)

( * ) Notice: Subject to any disclaimer, the term of this patent is extended or adjusted under 35 U.S.C. 154(b) by 0 days.

(21) Appl. No.: 15/320,484

(22) PCT Filed: Jun. 24, 2015

(86) PCT No.: PCT/PL2015/050025
§ 371 (c)(1),
(2) Date: Dec. 20, 2016

(87) PCT Pub. No.: WO2015/199564
PCT Pub. Date: Dec. 30, 2015

(65) Prior Publication Data
US 2017/0165352 A1 Jun. 15, 2017

(30) Foreign Application Priority Data

Jun. 24, 2014 (PL) .......................... 408649

(51) Int. Cl.
A61K 39/00 (2006.01)
A61K 39/12 (2006.01)
C07K 16/10 (2006.01)
A61K 39/145 (2006.01)
C07K 14/005 (2006.01)

(52) U.S. Cl.
CPC ............ A61K 39/145 (2013.01); A61K 39/12 (2013.01); C07K 14/005 (2013.01); C07K 16/1018 (2013.01); A61K 2039/543 (2013.01); A61K 2039/545 (2013.01); A61K 2039/552 (2013.01); A61K 2039/55505 (2013.01); C12N 2760/16122 (2013.01); C12N 2760/16134 (2013.01); C12N 2760/16151 (2013.01); C12N 2760/16171 (2013.01)

(58) Field of Classification Search
CPC ............ C12N 2760/16134; C12N 7/00; C12N 2760/16122; C12N 2760/16034; C12N 2760/16234; C12N 2760/16121; C12N 2760/16151; C12N 15/86; C12N 2760/16123; C12N 2760/16171; C12N 2760/16022; C12N 2760/16111; C12N 2830/60; A61K 39/145; A61K 39/12; A61K 2039/5254; A61K 2039/525; A61K 39/00; A61K 9/0019; A61K 2039/6075; A61K 39/42; A61K 2039/552; A61K 2039/543; A61K 2039/545; A61K 2039/55505; C07K 14/005; C07K 16/1018; C07K 2319/00; C07K 2317/33; C07K 14/11
See application file for complete search history.

(56) References Cited

FOREIGN PATENT DOCUMENTS

| WO | 2007022425 A2 | 2/2007 | |
| WO | 2012011868 A1 | 1/2012 | |
| WO | 2013041877 A2 | 3/2013 | |
| WO | WO-2013043067 A2 * | 3/2013 | |
| WO | WO-2015093996 A1 * | 6/2015 | ............. A61K 39/12 |

OTHER PUBLICATIONS

Gora-Sochacka A, Stachyra A, Sirko A. Hemagglutinin [synthetic construct]. GenBank: AFZ15787.1. Dep. Dec. 31, 2013.*
Mundt E, Weber S, Harder T, Mettenleiter TC, Werner O. Hemagglutinin [Influenza A virus (A/swan/Germany/R65/2006(H5N1))]. GenBank: ABE26829.1. Dep. Jan. 26, 2007.*
Aguilar-Yáñez JM, Portillo-Lara R, Mendoza-Ochoa GI, García-Echauri SA, López-Pacheco F, Bulnes-Abundis D, Salgado-Gallegos J, Lara-Mayorga IM, Webb-Vargas Y, León-Angel FO, Rivero-Aranda RE, et. al. An influenza A/H1N1/2009 hemagglutinin vaccine produced in *Escherichia coli*. PLoS One. Jul. 22, 2010;5(7):e11694.*

(Continued)

Primary Examiner — Rachel B Gill
(74) Attorney, Agent, or Firm — Thomas| Horstemeyer, LLP

(57) ABSTRACT

The invention relates to an influenza viruses hemagglutinin protein as a vaccine antigen against influenza viruses, in particular to a protein being a fragment of H5 hemagglutinin from highly pathogenic avian influenza virus (HPAIV) H5N1 strain, expressed in a bacterial expression system. The protein according to the invention is a potential ingredient of an anti-HPAIV H5N1 vaccine, administered to chickens parenterally or through mucous membranes in the presence of adjuvants. The object of the invention is also a method of obtaining the vaccine protein.

15 Claims, 23 Drawing Sheets
Specification includes a Sequence Listing.

(56) References Cited

OTHER PUBLICATIONS

International Search Report for PCT/PL2015/050025 dated Oct. 9, 2015.
R.P. De Vries et al., "Glycan-dependent immunogenicity of recombinant soluble trimeric hemagglutinin", Journal of Virology; vol. 86, No. 21, Aug. 22, 2012, pp. 11735-11744, XP055111254.
Zuzana Biesova et al., "Preparation characterization, and immunogenicity in mice of a recombinant influenza H5 hemagglutinin vaccine against the avian H5N1 A/Vietnam/1203/2004 influenza virus", Vaccine; vol. 27, No. 44, Oct. 1, 2009, pp. 6234-6238, XP055214012.
Gene, "Recombinant influenza A virus H5N1 hemagglutinin general information", J. Virol. J. Virol. J. Biol. Chem. J. Biol. Chem; Jan. 1, 2000, pp. 2714-2720, XP055214071.
Violetta Saczynska, "Influenza virus hemagglutinin as a vaccine antigen produced in bacteria", Acta Biochimica Polonica; Sep. 8, 2014, pp. 561-572, XP055214010.
International Search Report and Written Opinion for PCT/PL2015/050025 dated Sep. 9, 2015.
R. P. de Vries, et al., Glycan-Dependent Immunogenicity of Recombinant Soluble Trimeric Hemagglutinin, Journal of Virology 86:21, Aug. 22, 2012, pp. 11735-11744.
Zuzana Biesova, et al., Preparation, characterization, and immunogenicity in mice of a recombinant influenza H5 hemagglutinin vaccine against the avian H5N1 A/Vietnam/1203/2004 influenza virus, Vaccine 27:44, Oct. 1, 2009, pp. 6234-6238.
Recombinant Influenza A Virus H5N1 Hemagglutinin General Information, Sino Biological, Inc. Catalog No. 11059-V0861. Retrieved online: http://www.tokyofuturestyle.com/products/jp/infection/list/pdf/H5N1/11059-V08B1%20Abar-headed%20gooseQinghai142008%20(H5N1).pdf. Accessed Apr. 25, 2017.
Violetta Saczynska, Influenza virus hemaglutinin as a vaccine antigen produced in bacteria, Acta Biochemica Polonica 61:3, Sep. 8, 2014, pp. 561-572.
Avian Influenza in: OIE Manual of Diagnostic Tests and Vaccines for Terrestrial Animals, 2012: 436-454.
Aguilar-Yáñez, et al., An influenza A/H1N1/2009 hemagglutinin vaccine produced in *Escherichia coli*, PLoS One 5:7, 2010, 1-14.
Biesova, et al., Preparation, characterization, and immunogenicity in mice of a recombinant influenza H5 hemagglutinin vaccine against the avian H5N1 A/Vietnam/1203/2004 influenza virus. Vaccine. 2009; 27:6234-8.
Bommakanti, et al., Design of an HA2-based *Escherichia coli* expressed influenza immunogen that protects mice from pathogenic challenge. Proc Natl Acad Sci U S A. 2010; 107:13701-6.
Bommakanti, et al., Design of *Escherichia coli*-expressed stalk domain immunogens of H1N1 hemagglutinin that protect mice from lethal challenge. J Virol. 2012; 86:13434-44.
Bosch, et al., Recombinant soluble, multimeric HA and NA exhibit distinctive types of protection against pandemic swine-origin 2009 A(H1N1) influenza virus infection in ferrets. J Virol. 2010; 84:10366-74.
Bradford MM. A rapid and sensitive method for the quantitation of microgram quantities of protein utilizing the principle of protein-dye binding. Anal Biochem. 1976; 72:248-54.
Chiu, et al., Immunological study of HA1 domain of hemagglutinin of influenza H5N1 virus. Biochem Biophys Res Commun. 2009; 383:27-31.
Chung, et al., A rapid and convenient method for preparation and storage of competent bacterial cells. Nucleic Acids Res. 1988; 16:3580.
DuBois, et al., The receptor-binding domain of influenza virus hemagglutinin produced in *Escherichia coli* folds into its native, immunogenic structure. J Virol. 2011; 85:865-72.
Ekiert, et al., Antibody recognition of a highly conserved influenza virus epitope. Science. 2009; 324:246-51.
Gromadzka, et al., Detection of changes in avian influenza genome fragments by multitemperature single-strand conformational polymorphism. Mol Cell Probes. 2008; 22:301-4.

Hong, et al., Antibody recognition of the pandemic H1N1 Influenza virus hemagglutinin receptor binding site. J Virol. 2013; 87:12471-80.
Horthongkham, et al., Specific antibody response of mice after immunization with COS-7 cell derived avian influenza virus (H5N1) recombinant proteins. J Immune Based Ther Vaccines. 2007; 5:10, 1-5.
Jegerlehner, et al., Bacterially produced recombinant influenza vaccines based on virus-like particles. PLoS One. 2013; 8:e78947, 1-12.
Jeon, et al., Immunization with influenza virus hemagglutinin globular region containing the receptor-binding pocket. Viral Immunol. 2002; 15:165-76.
Khurana, et al., Vaccines with MF59 adjuvant expand the antibody repertoire to target protective sites of pandemic avian H5N1 influenza virus. Sci Transl Med. 2010; 2:15ra5, 1-7.
Khurana, et al., Properly folded bacterially expressed H1N1 hemagglutinin globular head and ectodomain vaccines protect ferrets against H1N1 pandemic influenza virus. PLoS One. 2010; 5:7, 1-11.
Khurana, et al., Recombinant HA1 produced in *E. coli* forms functional oligomers and generates strain-specific SRID potency antibodies for pandemic influenza vaccines. Vaccine. 2011; 29:5657-65.
Khurana, et al., Bacterial HA1 vaccine against pandemic H5N1 influenza virus: evidence of oligomerization, hemagglutination, and cross-protective immunity in ferrets. J Virol. 2011; 85:1246-56.
Koenen, et al., Immunological differences between layer- and broiler-type chickens. Vet Immunol Immunopathol. 2002; 89:47-56.
Laemmli UK. Cleavage of structural proteins during the assembly of the head of bacteriophage T4. Nature. 1970; 227:680-5.
Liu, et al., Flagellin-HA vaccines protect ferrets and mice against H5N1 highly pathogenic avian influenza virus (HPAIV) infections. Vaccine. 2012; 30:6833-8.
Liu, et al., Immunogenicity and efficacy of flagellin-fused vaccine candidates targeting 2009 pandemic H1N1 influenza inmice. PLoS One. 2011; 6:6, 1-9.
Loeffen, et al., Vaccination with a soluble recombinant hemagglutinin trimer protects pigs against a challenge with pandemic (H1N1) 2009 influenza virus. Vaccine. 2011; 29:1545-50.
Minta Z. 2008 HPAI-PLAN Instrukcje przeprowadzania laboratoryjnych badań diagnostycznych w kierunku grypy ptaków, 1-9.
Okuno, et al., A common neutralizing epitope conserved between the hemagglutinins of influenza A virus H1 and H2 strains. J Virol. 1993; 67:2552-8.
Sagawa, et al., The immunological activity of a deletion mutant of influenza virus haemagglutinin lacking the globular region. J Gen Virol. 1996; 77:1483-7.
Sánchez-Arreola, et al., A baseline process for the production, recovery, and purification of bacterial influenza vaccine candidates. Biotechnol Prog. 2013; 29:896-908.
Shen, et al., Comparing the antibody responses against recombinant hemagglutinin proteins of avian influenza A (H5N1) virus expressed in insect cells and bacteria. J Med Virol. 2008; 80:1972-83.
Skibinski, et al., Enhanced neutralizing antibody titers and Th1 polarization from a novel *Escherichia coli* derived pandemic influenza vaccine. PLoS One. 2013; 8:10, 1-11.
Song, et al., Efficacious recombinant influenza vaccines produced by high yield bacterial expression: a solution to global pandemic and seasonal needs. PLoS One. 2008; 3:5, 1-8.
Song, et al., Superior efficacy of a recombinant flagellin:H5N1 HA globular head vaccine is determined by the placement of the globular head within flagellin. Vaccine. 2009; 27:5875-84.
Spackman, et al., Development of a real-time reverse transcriptase PCR assay for type A influenza virus and the avian H5 and H7 hemagglutinin subtypes. J Clin Microbiol. 2002; 40: 3256-60.
Steel, et al., Influenza virus vaccine based on the conserved hemagglutinin stalk domain. MBio. 2010; 1(1), 1-9.
Suarez DL. Overview of avian influenza DIVA test strategies. Biologicals. 2005; 33:221-6.
Sui, et al., Structural and functional bases for broad-spectrum neutralization of avian and human influenza A viruses. Nat Struct Mol Biol. 2009; 16:265-73.

(56) References Cited

OTHER PUBLICATIONS

Taylor, et al., Development of VAX128, a recombinant hemagglutinin (HA) influenza-flagellin fusion vaccine with improved safety and immune response. Vaccine. 2012 30:5761-9.

Taylor, et al., Induction of a potent immune response in the elderly using the TLR-5 agonist, flagellin, with a recombinant hemagglutinin influenza-flagellin fusion vaccine (VAX125, STF2.HA1 SI). Vaccine. 2011 29: 4897-902.

Treanor, et al., Safety and immunogenicity of a recombinant hemagglutinin influenza-flagellin fusion vaccine (VAX125) in healthy young adults. Vaccine. 2010; 28:8268-74.

van den Berg, et al., Influenza vaccines and vaccination strategies in birds. Comp Immunol MicrobiolInfect Dis. 2008; 31:121-65.

Verma, et al., Oligomeric recombinant H5 HA1 vaccine produced in bacteria protects ferrets from homologous and heterologous wild-type H5N1 influenza challenge and controls viral loads better than subunit H5N1 vaccine by eliciting high-affinity antibodies. J Virol. 2012; 86:12283-93.

Wei, et al., Comparative efficacy of neutralizing antibodies elicited by recombinant hemagglutinin proteins from avian H5N1 influenza virus. J Virol. 2008; 82:6200-8.

Weldon, et al., Compans RW. Enhanced immunogenicity of stabilized trimeric soluble influenza hemagglutinin. PLoS One. 2010; 5:e12466, 1-8.

Wiley, et al., Structural identification of the antibody-binding sites of Hong Kong influenza haemagglutinin and their involvement in antigenic variation. Nature. 1981; 289:373-8.

Wilson, et al., Structural basis of immune recognition of influenza virus hemagglutinin. Annu Rev Immunol. 1990; 8:737-71.

Xie, et al., Preparation and immune activity analysis of H5N1 subtype avian influenza virus recombinant protein-based vaccine. Poult Sci. 2009; 88:1608-15.

Xuan, et al., Structural vaccinology: structure-based design of influenza A virus hemagglutinin subtype-specific subunit vaccines. Protein Cell. 2011; 2:997-1005.

\* cited by examiner

5'ATCTGTCAAAATGGAGAAAATAGTGCTTCTTTTTGCAATAGTCAGTCTTGTTAAAA
GTGATCAGATTTGCATTGGTTACCATGCAAACAACTCGACAGAGCAGGTTGACACA
ATAATGGAAAAGAACGTCACTGTTACACACGCCCAAGACATACTGGAAAAGACACA
CAACGGGAAGCTCTGCGATCTAGATGGAGTGAAGCCTCTAATTTTAAGAGATTGTA
GTGTAGCTGGATGGCTCCTCGGGAACCCAATGTGTGACGAATTCCTCAATGTGCC
GGAATGGTCTTACATAGTGGAGAAGATCAATCCAGCCAATGACCTCTGTTACCCAG
GGAATTTCAACGACTATGAAGAACTGAAACACCTATTGAGCAGAATAAACCATTTTG
AGAAAATTCAGATCATCCCCAAAAGTTCTTGGTCAGATCATGAAGCCTCATCAGGG
GTGAGCTCAGCATGTCCATACCAGGGAAGGTCCTCCTTTTTAGAAATGTGGTATG
GCTTATCAAAAGGACAATGCATACCCAACAATAAAGAGAAGCTACAATAATACCAA
CCAAGAAGATCTTTTGGTACTGTGGGGATTCACCATCCAAATGATGCGGCAGAG
CAGACAAGGCTCTATCAAAACCCAACCACCTATATTTCCGTTGGGACATCAACACT
AAACCAGAGATTGGTACCAAAAATAGCTACTAGATCCAAGGTAAACGGGCAAAGTG
GAAGGATGGAGTTCTTTTGGACAATTTTAAAACCGAATGATGCAATAAACTTTGAGA
GTAATGGAAATTTCATTGCTCCAGAAAATGCATACAAAATTGTCAAGAAGGGGAC
TCAACAATTATGAAAAGTGAATTGGAATATGGTAACTGCAACACCAAGTGTCAAACT
CCAATAGGGGCGATAAACTCTAGTATGCCATTCCACAACATCCACCCTCTCACCAT
CGGGGAATGCCCCAAATATGTGAAATCAAACAGATTAGTCCTTGCGACTGGGCTCA
GAAATAGCCCTCAAGGAGAGAAGAAGAAAAAGAGAGGACTATTTGGAGCTAT
AGCAGGTTTTATAGAGGGAGGATGGCAGGGAATGGTAGATGGTTGGTATGGGTAC
CACCATAGCAACGAGCAGGGGAGTGGGTACGCTGCAGACAAAGAATCCACTCAAA
AGGCAATAGATGGAGTCACCAATAAGGTCAACTCGATCATTAACAAAATGAACACT
CAGTTTGAGGCCGTTGGAAGGGAATTTAATAACTTAGAAAGGAGAATAGAAAATTT
AAACAAGAAGATGGAAGACGGATTCCTAGATGTCTGGACTTATAATGCTGAACTTC
TGGTTCTCATGGAAAATGAGAGAACTCTAGACTTTCATGACTCAAATGTCAAGAAC
CTTTACGACAAGGTCCGACTACAGCTTAGGGATAATGCAAAGGAGCTTGGTAACG
GTTGTTTCGAGTTCTATCACAGATGTGATAATGAATGCATGGAAAGTGTAAGAAAC
GGAACGTATGACTACCCGCAGTATTCAGAAGAAGCAAGATTAAAAGAGAGGAAAT
AAGTGGAGTAAAATTGGAATCAATAGGAACCTACCAAATACTGTCAATTTATTCAAC
AGTGGCGAGCTCCCTAGCACTGGCAATCATGGTGGCTGGTCTATCTTTATGGATGT
GCTCCAATGGATCGTTACAATGCAGAATTTGCATTTAAATTTGTGAGTTCAGAGTC3'

FIG. 1

5'atggatcagatttgcattggttaccatgcaaacaactcgacagagcaggttgacacaataatggaaaagaacgtcact
gttacacacgcccaagacatactggaaaagacacacaacgggaagctctgcgatctagatggagtgaagcctctgatt
ctgcgcgattgtagtgtagctggatggctcctcgggaacccaatgtgtgacgaattcctcaatgtgccggaatggtcttaca
tagtggagaagatcaatccagccaatgaccctgttacccagggaatttcaacgactatgaagaactgaaacacctattg
agcagaataaaccattttgagaaaattcagatcatccccaaaagttcttggtcagatcatgaagcctcatcaggggtgagc
tcagcatgtccataccagggaaggtcctcctttttcgcaatgtggtatggcttatcaaaaaggacaatgcatacccaacaa
taaagagaagctacaataataccaaccaagaagatcttttggtactgtgggggattcaccatccaaatgatgcggcagag
cagacaaggctctatcaaaacccaaccacctatatttccgttgggacatcaacactaaaccagagattggtaccaaaaat
agctactagatccaaggtaaacgggcaaagtggaaggatggagttcttttggacaattttaaaaccgaatgatgcaataa
actttgagagtaatggaaatttcattgctccagaaaatgcatacaaaattgtcaagaaaggggactcaacaattatgaaaa
gtgaattggaatatggtaactgcaacaccaagtgtcaaactccaataggggcgataaactctagtatgccattccacaac
atccaccctctcaccatcggggaatgccccaaatatgtgaaatcaaacagattagtccttgcgactgggctcagaaatag
ccctcaaggagagcgccgccgcaaaaagagagggactgtttggagctatagcaggttttatagagggaggatggcag
ggaatggtagatggttggtatgggtaccaccatagcaacgagcaggggagtgggtacgctgcagacaaagaatccact
caaaaggcaatagatggagtcaccaataaggtcaactcgatcattaacaaaatgaacactcagtttgaggccgttggaa
gggaatttaataacttagaaaggagaatagaaaatttaaacaagaagatggaagacggattcctagatgtctggacttat
aatgctgaacttctggttctcatggaaaatgagagaactctagactttcatgactcaaatgtcaagaaccttacgacaaggt
ccgactacagcttagggataatgcaaaggagcttggtaacggttgtttcgagttctatcacagatgtgataatgaatgcatg
gaaagtgtaagaaacggaacgtatgactacccgcagtattcagaagaagcaagattaaaacgcgaggaaataagtg
gagtataa3'

FIG. 3

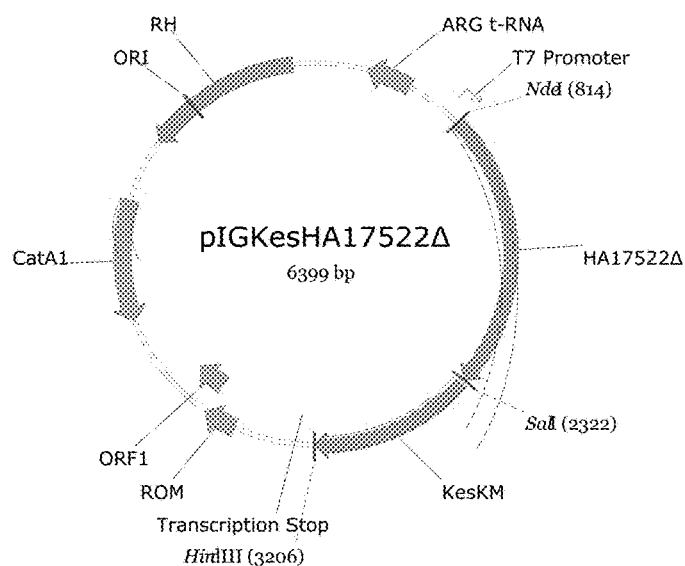

FIG. 4

DQICIGYHANNSTEQVDTIMEKNVTVTHAQDILEKTH
NGKLCDLDGVKPLILRDCSVAGWLLGNPMCDEFLNV
PEWSYIVEKINPANDLCYPGNFNDYEELKHLLSRINH
FEKIQIIPKSSWSDHEASSGVSSACPYQGRSSFFRNV
VWLIKKDNAYPTIKRSYNNTNQEDLLVLWGIHHPNDA
AEQTRLYQNPTTYISVGTSTLNQRLVPKIATRSKVNG
QSGRMEFFWTILKPNDAINFESNGNFIAPENAYKIVK
KGDSTIMKSELEYGNCNTKCQTPIGAINSSMPFHNIH
PLTIGECPKYVKSNRLVLATGLRNSPQGE RRRK KRG L
FGAIAGFIEGGWQGMVDGWYGYHHSNEQGSGYAADK
ESTQKAIDGVTNKVNSIINKMNTQFEAVGREFNNLER
RIENLNKKMEDGFLDVWTYNAELLVLMENERTLDFHD
SNVKNLYDKVRLQLRDNAKELGNGCFEFYHRCDNEC
MESVRNGTYDYPQYSEEARLKREEISGV (SEQ ID NO: 1)

FIG. 5A

DQICIGYHANNSTEQVDTIMEKNVTVTHAQDILEKTH
NGKLCDLDGVKPLILRDCSVAGWLLGNPMCDEFLNV
PEWSYIVEKINPANDLCYPGNFNDYEELKHLLSRINH
FEKIQIIPKSSWSDHEASSGVSSACPYQGRSSFFRNV
VWLIKKDNAYPTIKRSYNNTNQEDLLVLWGIHHPNDA
AEQTRLYQNPTTYISVGTSTLNQRLVPKIATRSKVNG
QSGRMEFFWTILKPNDAINFESNGNFIAPENAYKIVK
KGDSTIMKSELEYGNCNTKCQTPIGAINSSMPFHNIH
PLTIGECPKYVKSNRLVLATGLRNSPQGE        GL
FGAIAGFIEGGWQGMVDGWYGYHHSNEQGSGYAADK
ESTQKAIDGVTNKVNSIINKMNTQFEAVGREFNNLER
RIENLNKKMEDGFLDVWTYNAELLVLMENERTLDFHD
SNVKNLYDKVRLQLRDNAKELGNGCFEFYHRCDNEC
MESVRNGTYDYPQYSEEARLKREEISGV (SEQ ID NO: 2)

FIG. 5B

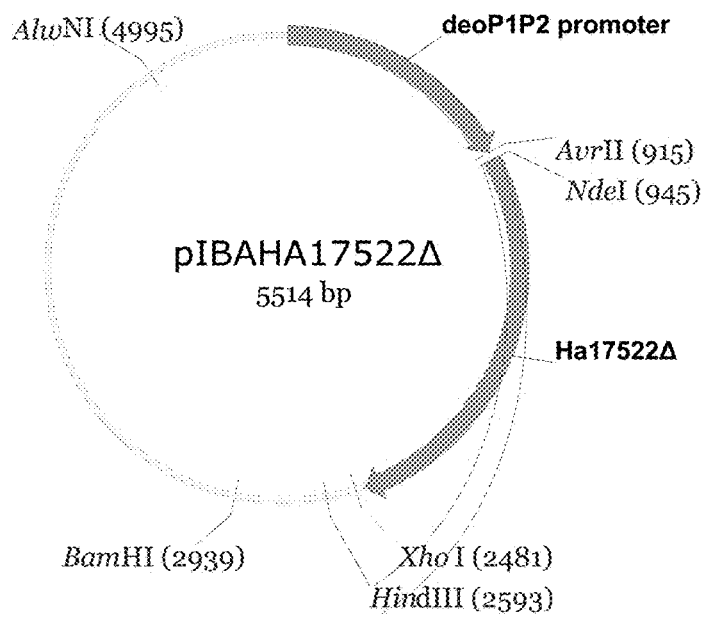
FIG. 9
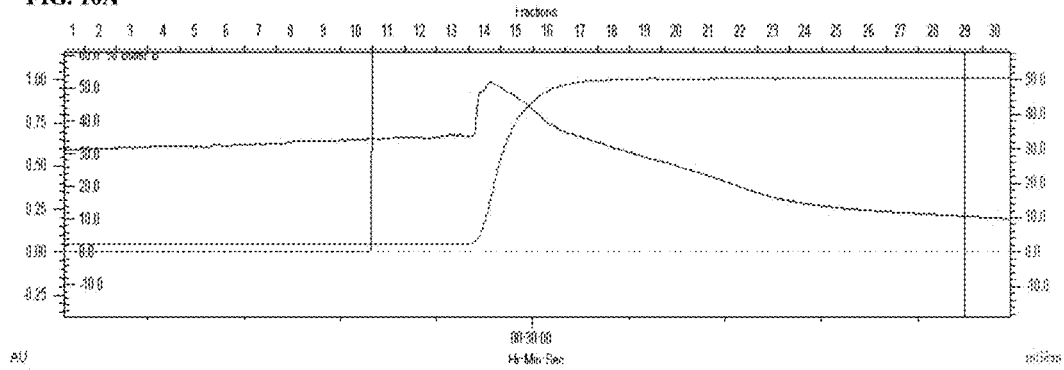
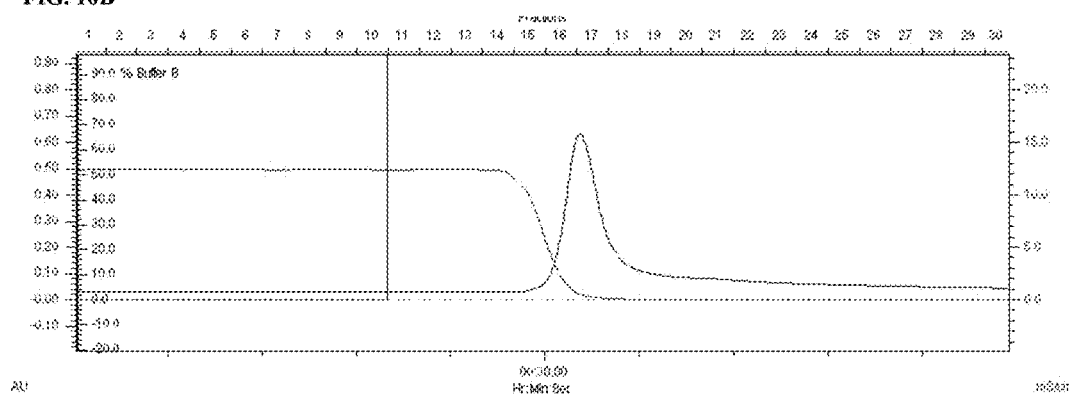
FIGS. 10A-10B

SEQUENCE LISTING

```
<160> NUMBER OF SEQ ID NOS: 12

<210> SEQ ID NO 1
<211> LENGTH: 506
<212> TYPE: PRT
<213> ORGANISM: Influenza virus

<400> SEQUENCE: 1

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Ile Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Arg Ser Ser Phe Phe
    130                 135                 140

Arg Asn Val Val Trp Leu Ile Lys Lys Asp Asn Ala Tyr Pro Thr Ile
145                 150                 155                 160

Lys Arg Ser Tyr Asn Asn Thr Asn Gln Glu Asp Leu Leu Val Leu Trp
                165                 170                 175
```

Gly Ile His His Pro Asn Asp Ala Ala Glu Gln Thr Arg Leu Tyr Gln
                180                 185                 190

Asn Pro Thr Thr Tyr Ile Ser Val Gly Thr Ser Thr Leu Asn Gln Arg
            195                 200                 205

Leu Val Pro Lys Ile Ala Thr Arg Ser Lys Val Asn Gly Gln Ser Gly
        210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Asn Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Ile Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Gly Glu Arg Arg Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
370                 375                 380

Ile Ile Asn Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
450                 455                 460

Asn Gly Cys Phe Glu Phe Tyr His Arg Cys Asp Asn Glu Cys Met Glu
465                 470                 475                 480

Ser Val Arg Asn Gly Thr Tyr Asp Tyr Pro Gln Tyr Ser Glu Glu Ala
                485                 490                 495

Arg Leu Lys Arg Glu Glu Ile Ser Gly Val
            500                 505

<210> SEQ ID NO 2
<211> LENGTH: 500
<212> TYPE: PRT
<213> ORGANISM: Influenza virus

<400> SEQUENCE: 2

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

```
Pro Leu Ile Leu Arg Asp Cys Ser Val Ala Gly Trp Leu Leu Gly Asn
 50                  55                  60

Pro Met Cys Asp Glu Phe Leu Asn Val Pro Glu Trp Ser Tyr Ile Val
 65                  70                  75                  80

Glu Lys Ile Asn Pro Ala Asn Asp Leu Cys Tyr Pro Gly Asn Phe Asn
                 85                  90                  95

Asp Tyr Glu Glu Leu Lys His Leu Leu Ser Arg Ile Asn His Phe Glu
            100                 105                 110

Lys Ile Gln Ile Ile Pro Lys Ser Trp Ser Asp His Glu Ala Ser
        115                 120                 125

Ser Gly Val Ser Ser Ala Cys Pro Tyr Gln Gly Arg Ser Ser Phe Phe
130                 135                 140

Arg Asn Val Val Trp Leu Ile Lys Lys Asp Asn Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
            195                 200                 205

Leu Val Pro Lys Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Asn Ala Tyr Lys Ile
                245                 250                 255

Val Lys Lys Gly Asp Ser Thr Ile Met Lys Ser Glu Leu Glu Tyr Gly
                260                 265                 270

Asn Cys Asn Thr Lys Cys Gln Thr Pro Ile Gly Ala Ile Asn Ser Ser
            275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Gly Glu Gly Leu Phe Gly Ala Ile Ala Gly Phe Ile Glu Gly
                325                 330                 335

Gly Trp Gln Gly Met Val Asp Gly Trp Tyr Gly Tyr His His Ser Asn
            340                 345                 350

Glu Gln Gly Ser Gly Tyr Ala Ala Asp Lys Glu Ser Thr Gln Lys Ala
            355                 360                 365

Ile Asp Gly Val Thr Asn Lys Val Asn Ser Ile Ile Asn Lys Met Asn
        370                 375                 380

Thr Gln Phe Glu Ala Val Gly Arg Glu Phe Asn Asn Leu Glu Arg Arg
385                 390                 395                 400

Ile Glu Asn Leu Asn Lys Lys Met Glu Asp Gly Phe Leu Asp Val Trp
                405                 410                 415

Thr Tyr Asn Ala Glu Leu Leu Val Leu Met Glu Asn Glu Arg Thr Leu
            420                 425                 430

Asp Phe His Asp Ser Asn Val Lys Asn Leu Tyr Asp Lys Val Arg Leu
        435                 440                 445

Gln Leu Arg Asp Asn Ala Lys Glu Leu Gly Asn Gly Cys Phe Glu Phe
450                 455                 460
```

```
Tyr His Arg Cys Asp Asn Glu Cys Met Glu Ser Val Arg Asn Gly Thr
465                 470                 475                 480

Tyr Asp Tyr Pro Gln Tyr Ser Glu Glu Ala Arg Leu Lys Arg Glu Glu
            485                 490                 495

Ile Ser Gly Val
            500

<210> SEQ ID NO 3
<211> LENGTH: 1735
<212> TYPE: DNA
<213> ORGANISM: Influenza virus

<400> SEQUENCE: 3
atctgtcaaa atggagaaaa tagtgcttct ttttgcaata gtcagtcttg ttaaaagtga      60
tcagatttgc attggttacc atgcaaacaa ctcgacagag caggttgaca caataatgga     120
aaagaacgtc actgttacac acgcccaaga catactggaa aagacacaca cgggaagct     180 ctgcgatcta gatggagtga agcctctaat tttaagagat tgtagtgtag ctggatggct     240
cctcgggaac ccaatgtgtg acgaattcct caatgtgccg aatggtcttt acatagtgga     300
gaagatcaat ccagccaatg acctctgtta cccagggaat ttcaacgact atgaagaact     360
gaaacaccta ttgagcagaa taaaccattt tgagaaaatt cagatcatcc ccaaaagttc     420
ttggtcagat catgaagcct catcaggggt gagctcagca tgtccatacc agggaaggtc     480 ctccttttt agaaatgtgg tatggcttat caaaaaggac aatgcatacc caacaataaa     540
gagaagctac aataatacca accaagaaga tcttttggta ctgtggggga ttcaccatcc     600
aaatgatgcg gcagagcaga caaggctcta tcaaaaccca accacctata tttccgttgg     660
gacatcaaca ctaaaccaga gattggtacc aaaaatagct actagatcca aggtaaacgg     720
gcaaagtgga aggatggagt tcttttggac aattttaaaa ccgaatgatg caataaactt     780
tgagagtaat ggaaatttca ttgctccaga aaatgcatac aaaattgtca agaaagggga     840
ctcaacaatt atgaaaagtg aattggaata tggtaactgc aacaccaagt gtcaaactcc     900
aataggggcg ataaactcta gtatgccatt ccacaacatc caccctctca ccatcgggga     960
atgccccaaa tatgtgaaat caaacagatt agtccttgcg actgggctca gaaatagccc    1020
tcaaggagag agaagaagaa aaagagagg actatttgga gctatagcag gttttataga    1080
gggaggatgg caggga atgg tagatggttg gtatgggtac caccatagca acgagcaggg    1140
gagtgggtac gctgcagaca agaatccac tcaaaaggca atagatggag tcaccaataa    1200
ggtcaactcg atcattaaca aatgaacac tcagtttgag gccgttggaa gggaatttaa    1260
taacttagaa aggagaatag aaaatttaaa caagaagatg aagacggat tcctagatgt    1320 ctggacttat aatgctgaac ttctggttct catggaaaat gagagaactc tagactttca    1380
tgactcaaat gtcaagaacc tttacgacaa ggtccgacta cagcttaggg ataatgcaaa    1440
ggagcttggt aacggttgtt tcgagttcta tcacagatgt gataatgaat gcatggaaag    1500
tgtaagaaac ggaacgtatg actacccgca gtattcagaa gaagcaagat taaaaagaga    1560
ggaaataagt ggagtaaat tggaatcaat aggaacctac aaatactgt caatttattc    1620 aacagtggcg agctccctag cactggcaat catggtggct ggtctatctt tatggatgtg    1680
ctccaatgga tcgttacaat gcagaatttg catttaaatt tgtgagttca gagtc         1735
```

<210> SEQ ID NO 4
<211> LENGTH: 1524
<212> TYPE: DNA
<213> ORGANISM: Influenza virus

<400> SEQUENCE: 4

| | | |
|---|---|---|
| atggatcaga tttgcattgg ttaccatgca aacaactcga cagagcaggt tgacacaata | 60 |
| atggaaaaga acgtcactgt tacacacgcc caagacatac tggaaaagac acacaacggg | 120 |
| aagctctgcg atctagatgg agtgaagcct ctgattctgc gcgattgtag tgtagctgga | 180 |
| tggctcctcg ggaacccaat gtgtgacgaa ttcctcaatg tgccggaatg gtcttacata | 240 |
| gtggagaaga tcaatccagc caatgacctc tgttacccag ggaatttcaa cgactatgaa | 300 |
| gaactgaaac acctattgag cagaataaac catttgaga aaattcagat catccccaaa | 360 |
| agttcttggt cagatcatga agcctcatca ggggtgagct cagcatgtcc ataccaggga | 420 |
| aggtcctcct tttttcgcaa tgtggtatgg cttatcaaaa aggacaatgc atacccaaca | 480 |
| ataaagagaa gctacaataa taccaaccaa gaagatcttt tggtactgtg ggggattcac | 540 |
| catccaaatg atgcggcaga gcagacaagg ctctatcaaa acccaaccac ctatatttcc | 600 |
| gttgggacat caacactaaa ccagagattg gtaccaaaaa tagctactag atccaaggta | 660 |
| aacgggcaaa gtggaaggat ggagttcttt tggacaattt taaaaccgaa tgatgcaata | 720 |
| aactttgaga gtaatggaaa tttcattgct ccagaaaatg catacaaaat tgtcaagaaa | 780 |
| ggggactcaa caattatgaa aagtgaattg gaatatggta actgcaacac caagtgtcaa | 840 |
| actccaatag gggcgataaa ctctagtatg ccattccaca catccacccc tctcaccatc | 900 |
| ggggaatgcc ccaaatatgt gaaatcaaac agattagtcc ttgcgactgg gctcagaaat | 960 |
| agccctcaag gagagcgccg ccgcaaaaag agaggactgt ttggagctat agcaggtttt | 1020 |
| atagagggag gatggcaggg aatggtagat ggttggtatg ggtaccacca tagcaacgag | 1080 |
| caggggagtg gtacgctgc agacaaagaa tccactcaaa aggcaataga tggagtcacc | 1140 |
| aataaggtca actcgatcat taacaaaatg aacactcagt ttgaggccgt tggaagggaa | 1200 |
| tttaataact agaaaggag aatagaaaat ttaaacaaga gatgaagag cggattccta | 1260 |
| gatgtctgga cttataatgc tgaacttctg gttctcatgg aaaatgagag aactctagac | 1320 |
| tttcatgact caaatgtcaa gaacctttac gacaaggtcc gactacagct tagggataat | 1380 |
| gcaaaggagc ttggtaacgg ttgtttcgag ttctatcaca gatgtgataa tgaatgcatg | 1440 |
| gaaagtgtaa gaaacggaac gtatgactac ccgcagtatt cagaagaagc aagattaaaa | 1500 |
| cgcgaggaaa taagtggagt ataa | 1524 |

<210> SEQ ID NO 5
<211> LENGTH: 7
<212> TYPE: PRT
<213> ORGANISM: Artificial Sequence
<220> FEATURE:
<223> OTHER INFORMATION: Peptide Flexible Linker

<400> SEQUENCE: 5

Ser Gly Ser Gly Ser Gly Ser
1               5

<210> SEQ ID NO 6
<211> LENGTH: 10
<212> TYPE: PRT
<213> ORGANISM: Artificial Sequence

```
<220> FEATURE:
<223> OTHER INFORMATION: cleavage site for trypsin and subtilisin
      protease family

<400> SEQUENCE: 6

Gln Gly Glu Arg Arg Arg Lys Lys Arg Gly
1               5                   10

<210> SEQ ID NO 7
<211> LENGTH: 6
<212> TYPE: PRT
<213> ORGANISM: Artificial Sequence
<220> FEATURE:
<223> OTHER INFORMATION: basic amino acids in the 341-346 aa region of
      the HA antigen

<400> SEQUENCE: 7

Arg Arg Arg Lys Lys Arg
1               5

<210> SEQ ID NO 8
<211> LENGTH: 37
<212> TYPE: DNA
<213> ORGANISM: Artificial Sequence
<220> FEATURE:
<223> OTHER INFORMATION: forward PCR amplification primer for
      hemagglutinin coding gene

<400> SEQUENCE: 8
gaggggatcc atatggatca gatttgcatt ggttacc                          37

<210> SEQ ID NO 9
<211> LENGTH: 34
<212> TYPE: DNA
<213> ORGANISM: Artificial Sequence
<220> FEATURE:
<223> OTHER INFORMATION: Reverse PCR amplification primer for
      hemagglutinin coding gene

<400> SEQUENCE: 9
ggccctcgag ttatactcca cttatttcct cgcg                             34

<210> SEQ ID NO 10
<211> LENGTH: 24
<212> TYPE: DNA
<213> ORGANISM: Artificial Sequence
<220> FEATURE:
<223> OTHER INFORMATION: Primer for mRT-PCR for viral titer

<400> SEQUENCE: 10
agatgagtct tctaaccgag gtcg                                        24

<210> SEQ ID NO 11
<211> LENGTH: 23
<212> TYPE: DNA
<213> ORGANISM: Artificial Sequence
<220> FEATURE:
<223> OTHER INFORMATION: Primer for mRT-PCR for viral titer

<400> SEQUENCE: 11
tgcaaaaaca tcttcaagtc tct                                         23

<210> SEQ ID NO 12
<211> LENGTH: 20
<212> TYPE: DNA
<213> ORGANISM: Artificial Sequence
```

```
<220> FEATURE:
<223> OTHER INFORMATION: probe for mRT-PCR for viral titer the 5' end
      was FAM modified, 3' end was TAMRA modified
<220> FEATURE:
<221> NAME/KEY: misc_feature
<222> LOCATION: (1)..(1)
<223> OTHER INFORMATION: FAM modification
<220> FEATURE:
<221> NAME/KEY: misc_feature
<222> LOCATION: (20)..(20)
<223> OTHER INFORMATION: TAMRA modification

<400> SEQUENCE: 12
tcaggccccc tcaaagccga                                                   20
```

INFLUENZA VIRUS HEMAGGLUTININ PROTEIN AS A VACCINE ANTIGEN

CROSS-REFERENCE TO RELATED APPLICATIONS

This application is the 35 U.S.C. § 371 national stage application of PCT Application No. PCT/PL2015/050025, filed on Jun. 24, 2015, which claims the benefit of and priority to co-pending Polish Application No. P.408649, filed on Jun. 24, 2014, the content of which is hereby incorporated by reference in its entirety.

SEQUENCE LISTING

This application contains a sequence listing filed in electronic form as an ASCII.txt file entitled 922301-1020_ST25.txt, created on Jan. 9, 2019. The content of the sequence listing is incorporated herein in its entirety.

The object of the invention is the influenza virus (IV) hemagglutinin (HA) protein as a vaccine antigen against influenza viruses, in particular the H5 hemagglutinin protein of a highly pathogenic avian influenza virus (HPAIV) H5N1 strain, a composition comprising the said hemagglutinin protein applicable in the development of vaccines against influenza virus, an antibody binding to the said protein and a method of obtaining the hemagglutinin protein.

Solving the spatial structure of various HA serotypes, the development of in silico drug design methods, biotechnology and protein engineering have opened new prospects for anti-influenza vaccines produced in a bacterial expression system. The current work on obtaining such a vaccine is focused on HA proteins based on the HA-1 subunit, the HA-2 subunit, the ectodomain and the polypeptides containing repeated sequences of a single epitope (single-epitope vaccines) or several epitopes (multi-epitope vaccines) of the influenza virus proteins, including HA.

The proteins comprising the HA-1 subunit and fragments thereof are intended to provide immunity against influenza viruses of a particular HA serotype. Longer HA fragments, despite having conserved HA-2 subunit neutralizing epitopes (Ekiert D C et al. 2009, Okuno Y et al. 1993, Sui J et al. 2009), are also considered to be the so-called serotype-specific vaccines. Presumably, the globular domain inhibits stalk region recognition by immune cells either by masking it or through immunodominance (Steel J et al. 2010). As a result, vaccines comprising e.g. the AIV strain of H5 serotype elicits protective immune response against H5 viral infections, while either providing no immunity against other virus serotypes or a very low one (van den Berg et al. 2008). Due to the high variability of HA dominant antigenic sites, induction of cross-immunity is problematic also in relation to vaccine HA antigenic variants of related influenza virus strains. In the case of AIV H5N1, weak cross-reactivity is observed between antibodies induced against clade 1 viruses and clade 2 viruses, despite their considerable similarity (Khurana S et al. 2011b).

Studies on broadening of cross-immunity induced by subunit vaccines are focused on antigen properties and adjuvants. Comparative studies on the ability of various HA forms to induce protective immune response demonstrate that a significant role in this regard may be played by protein oligomerization (Khurana S et al. 2011b, Verma S et al. 2012). Attempts at generating universal vaccines are realized through designs of immunogens deprived of the globular domain, referred to as stalk domain-based HA proteins (Bommakanti G et al. 2010, 2012, Sagawa H et al. 1996, Steel J et al., 2010).

The possibility of enhancing the range of immune response by developing an efficacious immunogenic composition is indicated by studies of Khurana S et al. (2010a), who demonstrated, using MF59 in an H5N1-inactivated vaccine, an advantageous effect of an adjuvant on binding of induced antibodies to conformational epitopes of the HA-1 subunit, correlating with broadening of cross-neutralization between clades and the expected improved in vivo protection.

HA-1 Subunit-Based Proteins

Overexpression in *E. coli* was used to produce the HPAIV H5N1 HA fragment comprising a signal sequence and a HA-1 subunit with (Chiu F F et al. 2009) and without basic amino acids of the cleavage site between the HA-1 and HA-2 subunits (Shen S et al. 2008).

Shorter HA-1 subunit fragments expressed in bacteria together with a signal sequence: 1-330 aa, 1-320 aa of the H1N1pdm09 and H5N1 viruses and the 1-320 aa H5 HA fragment of three strains belonging to the 1, 2.1 and 2.2 clades of the H5N1 virus were obtained by Khurana S et al. (2010b, 2011a, 2011b) and Verma S et al. (2012).

According to other designs, fragments of the HA-1 subunit: 57-264 aa, 57-272 aa, 50-280 aa of H1 HA from the H1N1pdm09 influenza virus (Xuan C et al. 2011) and the 91-261 aa H3 HA fragment of the H3N2 influenza virus (Jeon S H and Arnon R 2002), comprising mainly the protein globular domain (gH), were produced in a bacterial expression system. The 63-286 aa H1 HA fragment of the H1N1pdm09 virus was expressed in *E. coli* in the form of monomers—mHA$_{63-286}$ (Aguilar-Yáñez J M et al. 2010, DuBois R M et al. 2011, Sánchez-Arreola P et al. 2013), as well as dimers—dHA$_{63-286}$, in which the HA proteins are linked by a sequence of 10 amino acid residues (Sánchez-Arreola P et al. 2013).

Proteins of various lengths based on the H1 HA globular domain of the H1N1/PR8 influenza virus (101-276 aa, 53-324 aa, 62-284 aa) were also obtained, two of which (53-324 aa, 62-284 aa) were linked to the C-terminus of type 2 flagellin of the *Salmonella typhimurium* strain (STF2) through the SGSGSGS (SEQ ID NO: 5) flexible linker (Song L et al., 2008). STF2 is a type 5 Toll-like receptor (TLR 5) ligand and according to the current state of knowledge, linking it to the HA protein should enhance the antigen ability to trigger immune response. Fusion proteins of STF with HA fragments of the H1N1/SI (Song L et al. 2008), H1N1pdm09 (Liu G et al. 2011) and H5N1 viruses (Song L et al. 2009) were obtained based on the same principle as the STF2:HA (62-284 aa) antigen of the H1N1/PR8 virus. Based on the H5 and H1pdm09 HA sequences the other formats of STF:HA protein than C-terminal ones were produced, differing in the number of HA molecules and their placement in fusion proteins (Liu G et al. 2011, 2012, Song L et al. 2009). The R0 and R3 constructs were generated by replacing the flagellin DO and D3 domains, respectively, with the HA protein, while the R3.2×HA construct was obtained by fusing one HA molecule to the flagellin C-terminus and the other in the site of the D3 domain. Certain formats of the STF2:HA fusion protein were used as immunogenic components of the VAX125 vaccine against seasonal influenza virus H1N1/SI (Treanor J J et al. 2010, Taylor D N et al. 2011) and three variants of the VAX128 vaccine against pandemic influenza virus N1N1pdm09 (Taylor D N et al., 2012). Vaccine compositions based on solutions utilizing HA fusion protein linked to flagellin were disclosed in documents EP 2 476 432, WO2009128950, WO2014035989.

Eleven HA proteins based on the H1 HA globular domain (gH) of the H1N1/PR8 virus were designed and produced, forming four (group A), two (group B) or one (group C) disulfide bond(s) (Jegerlehner A et al. 2013). Group A and B proteins were fused in vitro to virus-like particles (VLPs) derived from the Qβ bacteriophage. By structural alignment to the prototype HA fragment (gH1_A_PR8) gH proteins of the following viruses were obtained: H1N1pdm09, H5N1, H1N1, H3N2 and type B influenza virus, and were subsequently linked to Qβ-VLPs (Jegerlehner A et al. 2013, Skibinski D A et al. 2013).

The HA-1 subunit and its fragments were expressed in *E. coli* in inclusion bodies as insoluble proteins, therefore obtaining an antigen intended for vaccination required solubilization of the proteins and HA refolding. With various procedures for obtaining protein, strong dependence of effectiveness and efficiency of the H5 HA HA-1 subunit refolding on the applied method was definitely shown (Chiu F F et al. 2009). In the case of the HA globular domain it was further shown that the effectiveness and efficiency of protein refolding is largely dependent on the fragment of the HA-1 subunit, which is selected to produce the vaccine antigen (Jegerlehner A et al. 2013, Song L et al. 2008, Xuan C et al. 2011), thus confirming the importance of secondary structures formed by peptides adjacent to the globular domain (Song L et al., 2008) and disulfide bonds (Jegerlehner A et al., 2013) for proper protein folding.

Purified and refolded the HA-1 subunit fragments (1-330 aa, 1-320 aa) of the H1N1pdm09 and H5N1 viruses, produced in a bacterial expression system, in contrast to the shorter H5 HA fragment (28-320 aa), were mostly present in the form of trimers and oligomers (Khurana S et al. 2010b, 2011a, 2011b, Verma S et al. 2012). It has been shown that the HA-1 subunit oligomerization is mediated by the conserved amino acids in the protein signal sequence (Khurana S et al., 2011b) and that the 1-320 aa fragment of H5 and H1 HAs forms more stable oligomers than the 1-330 aa fragment (Khurana S et al., 2011a, 2011b). The HA protein oligomers, composed of trimers, agglutinated erythrocytes and bound to fetuin, which indicates the capacity of these proteins to bind to receptors containing sialic acid residues (Khurana S et al., 2010b, 2011b). As a result of purification and refolding of structurally corresponding HA-1 subunit fragments from a bacterial expression system, correctly folded fragments of hemagglutinins: H1pdm09, H5, H7 and H3, have been produced with high yields (Khurana S et al. 2011a, 2011b, Verma S et al. 2012). The obtained proteins comprised a large fraction of oligomers (≥70%) in the form of rosette structures composed of trimers, similar to those formed by native HA isolated from influenza viruses. In contrast, the refolded and purified HA-1 subunit fragments, smaller than the ones obtained by Khurana S et al. (2010b, 2011a, 2011b,) and Verma S et al. (2012), expressed in bacteria without the signal sequence, did not form oligomers and were present as monomers containing mainly the globular domain with correct conformation (Aguilar-Yáñez J M et al. 2010, DuBois R M et al. 2011, Jegerlehner A et al. 2013, Liu G et al. 2011, 2012, Skibinski D A et al. 2013, Song L et al. 2008, 2009, Xuan C et al. 2011) or formed dimers mediated by a peptide linker (Sánchez-Arreola P et al. 2013). The correctly folded proteins based on the HA globular domain exhibited erythrocyte agglutination activity, characteristic of oligomeric HA forms, after linking to Qβ-VLPs (Jegerlehner A et al. 2013).

Studies on the structure and/or antigenicity of the purified and refolded HA HA-1 subunit or its fragments have shown that the proteins produced in a bacterial expression system have well-preserved neutralizing conformational epitopes, essential for the stimulation of immune response (Aguilar-Yáñez J M et al. 2010, Chiu F F et al. 2009, DuBois R M et al. 2011, Hong et al. 2013, Khurana S et al. 2010b, 2011b, Sánchez-Arreola P et al. 2013, Song L et al. 2008, Verma S et al. 2012, Xuan C et al. 2011). Comparative studies on various STF:HA fusion protein constructs have shown that antigenicity and activity of TLR5 depend on the site of the HA protein and flagellin linkage (Liu G et al. 2011, 2012, Song L et al. 2009).

In tests with influenza viruses homologous to the vaccine antigen it has been shown that sera of animals parenterally vaccinated with HA: 1-330 aa, 1-320 aa (Khurana S et al. 2010b, 2011a), 57-264 aa (Xuan C et al. 2011), 63-286 aa (Aguilar-Yáñez J M et al. 2010) of the H1N1pdm09 viruses and 1-320 aa of the H5N1 virus (Khurana S et al. 2011b, Verma S et al. 2012), as well as STF2:HA of the H1N1/SI virus (Song L et al. 2008) inhibit hemagglutination and/or neutralize the viruses in vitro. A varied capacity to induce HI antibodies in animals has been documented for the C-terminal, R0, R3, R3×2HA formats of STF2:HA proteins (Liu G et al. 2011, 2012, Song et al. 2009). Immunization studies in a mouse model have shown that the gH proteins conjugated to Qβ-VLPs elicit significantly higher titers of native HA-specific antibodies, HI antibodies and neutralizing antibodies in comparison to their non-conjugated counterparts, and that they induce a strong Th1 response (Jegerlehner A et al. 2013, Skibinski D A et al. 2013).

In the case of vaccinations with the HA protein (1-320 aa) of H5N1 viruses, the neutralizing activity of sera has also been shown against H5N1 viruses belonging to other clades than that, from which the vaccine antigen was derived (Khurana S et al. 2011a, 2011b). Comparative studies of the antisera induced by vaccination with the oligomeric (1-320 aa) and monomeric (28-320 aa) HA protein of the H5N1 virus have shown that the induction of high titer of neutralizing antibodies with a broad range of cross-reactivity is associated with oligomerization of the vaccine antigen (Khurana S et al. 2011b). The importance of HA protein oligomerization for immune response quality has been confirmed in immunization studies carried out with oligomeric and monomeric fractions of the 1-320 aa H5 HA protein (Verma S et al. 2012).

The ability to block membrane fusion, which correlates with the neutralizing activity of HA pseudotyped lentiviral particles, has been shown for sera of rabbits vaccinated with the HA protein (1-340 aa) of the H5N1 virus (Shen S et al. 2008). Immunization studies in mice with a HA-1 subunit fragment (91-261 aa) of the H3N2 virus have shown that the vaccine is capable of inducing IgG antibodies in serum on parenteral administration, but also IgG antibodies in sera and IgA in lungs on intranasal administration (Jeon S H and Amon R. 2002). The induced antibodies recognized HA in intact particles of the H3N2, H1N1 and H2N2 viruses. Vaccinations of mice with the HA protein (91-261 aa) have shown that the protein induces both humoral and cellular response against influenza virus.

The final criteria in the assessment of vaccination efficacy with purified and refolded HA proteins based on the HA-1 subunit from a bacterial expression system are the results of studies on infection of vaccinated animals with influenza viruses under experimental conditions (challenge). The capacity of the vaccines to induce immunity against H1N1pdm09 virus has been assessed in the ferret (Aguilar- Yáñez J M et al. 2010, Khurana S et al. 2010b, Skibinski D A et al. 2013) and mouse models (Xuan C et al. 2011, Skibinski D A et al. 2013) using viruses homologous to the vaccine antigen to infect the animals. It has been shown that parenteral vaccination of animals with the HA proteins: 1-330 aa (Khurana S et al. 2010b), 57-264 aa (Xuan C et al. 2011), 63-286 (Aguilar-Yáñez J M et al. 2010) and the gH1pdm09-Qβ-VLPs (Skibinski D A et al. 2013) elicits protective immunity against influenza virus infection. Protective activity of the vaccinations was manifested in that challenged animals did not get sick from flu or the course of the disease was milder than in non-vaccinated animals. Efficacy of immunization with STF2:H1pdm09 fusion proteins was studied in a lethal challenge experiment using the H1N1pdm09 infectious virus adapted to mice (Liu G et al. 2011). All tested fusion protein formats at doses of 3 μg and 0.3 μs conferred protection of animals against infection. Using 0.03 μg-doses the relative efficacy of three vaccine formats was found to be: R3.2×H1>R3>C-terminal. In some challenge experiments it has been shown that vaccination induces a substantial reduction in infectious virus loads in the respiratory tract of animals (Liu G et al. 2011, Khurana S et al. 2010b, Skibinski D A et al. 2013).

Similar to the vaccines against H1N1pdm09, HA proteins based on the HA-1 subunit of HPAIV H5N1 produced in a bacterial expression system have been studied for their efficacy in challenge experiments. It has been shown that the H5 HA (1-320 aa) protein, when correctly folded and forming functional oligomers, in contrast to the monomeric fraction of the 1-320 aa protein and the monomeric 28-320 aa protein, elicits protective immune response in ferrets against HPAIV H5N1 when used in parenteral immunization (Khurana S et al. 2011b, Verma S et al. 2012). After challenge with a homologous virus the survival rate of animals vaccinated with a largely oligomeric antigen or an exclusively oligomeric one was 100%, while after challenge with a heterologous one it was 80% and 100%, respectively. In ferrets, which survived the experimental infection, reduced infectious virus loads were also found in the upper respiratory tract. Studies on the capacity of STF2:H5 proteins to induce protective immune response have shown that vaccination with the C-terminal, R3, R3.2×H5 protein formats effectively protects the animals against infection with homologous H5N1 viruses, in contrast to immunization with the R0 format of fusion protein (Liu G et al. 2012, Song L et al. 2009). It has been further shown that the high survival rate of the vaccinated animals is accompanied by reduced virus loads in tissues and that the best vaccine antigen is the R3.2×HA format of STF2:H5 protein, effectively protecting animals against infection even when administered at sub-microgram doses.

Vaccines based on the HA-1 subunit of H3 and H1 HAs, produced in a bacterial expression system, have been tested in challenge experiments with infectious viruses: H3N2 and H1N1, respectively. In an experimental infection with the H3N2 virus it has been shown that intranasal administration of the HA (91-261 aa) protein induces 80% protection against infection in mice, measured by the number of animals, in which viruses applied in the challenge infection were detected in lungs (Jeon S H and Arnon R 2002). The prototype vaccine against influenza—STF2:H1_PR8 (62-284 aa) in the C-terminal configuration, administered parenterally, completely protected mice against lethal infection with the H1N1/PR8 influenza virus adapted to mice (Song L et al. 2008). Challenge experiments with vaccines containing type A and B gH proteins based on the H1 HA sequence of H1N1/PR8 virus have shown that these proteins fully protect mice against lethal infection with influenza viruses only after linking to QB-VLPs (Jegerlehner A et al. 2013). Additionally, it has been shown that vaccines based on QB-VLPs as carriers for H1N1/PR8 and H1N1pdm09 gH proteins provide a broad cross-immunity within the serotype and are affective even at sub-microgram doses.

HA-2 Subunit Based Proteins

By overexpressing in *E. coli*, a fragment of HA-2 subunit ectodomain (347-522 aa according to full-length HA numbering) of the H5N1 influenza virus was produced and purified by electroelution following denaturing polyacrylamide gel electrophoresis (SDS-PAGE), yielding at least partially denatured protein (Shen S et al. 2008). Sera of HA-2 protein vaccinated rabbits did not recognize HA surface-expressed on mammalian cells, did not block membrane fusion and did not neutralize pseudotyped lentiviral HA particles in vitro, whereas sera of animals immunized with the HA-1 (1-340 aa) protein, purified in the same manner as the HA-2 protein, bound to native HA and exhibited both activities.

The concept to apply proteins containing mainly the HA-2 subunit as vaccine antigens is realized by producing HA deprived of the globular domain, in which the HA-1 subunit fragments are retained, so that the produced protein maintains pre-fusion conformation and stalk region integrity (Steel J et al. 2010). Such HA proteins were produced in mammalian cells (Sagawa H et al. 1996, Steel J et al. 2010). Stalk domain-based immunogens, denoted as HA6 and H1HA0HA6, varying in linkage of the HA-2 subunit fragment with the HA-1 subunit fragments into one polypeptide chain, were produced in a bacterial expression system (Bommakanti G et al. 2010, 2012). Mutations stabilizing the HA-2 subunit pre-fusion conformation were introduced in both constructs. Stalk domain-based immunogens were produced using HA sequences of the H3N2, H1N1 and H1N1pdm09 viruses, while in certain proteins additional disulfide bond mutations or sequence-related mutations were introduced. The desired pre-fusion conformation of immunogens was confirmed in biophysical studies and antigenicity tests. In contrast to the HA0HA6-type protein forming random aggregates, H1HA6-type proteins were mostly present in the form of trimers. Conventional tests showed no neutralizing activity of the antisera obtained using stalk domain immunogens. In contrast, binding tests with rHA from heterologous viruses and competitive experiments with broadly neutralizing monoclonal antibodies showed the capacity of the proteins to induce cross-reacting antibodies. Vaccinations with H6- and/or H1HA0HA-type immunogens with sequences derived from HAs of various H1N1, H1N1pdm09 and H3N2 virus strains conferred full protection of mice against infection with homologous viruses, high survival rates (80-90%) of animals after challenge with heterologous viruses, whereas they did not provide heteroserotypic immunity.

HA Ectodomain Based Proteins

The full-length H5 HA ectodomain of HPAIV H5N1 without a signal sequence was produced in a bacterial expression system, preserving basic amino acids at the cleavage site (Biesova Z et al. 2009). The obtained ~60 kDa protein was recognized in Western blot by ferret antiserum antibodies against a homologous H5N1 virus. Mice immunization studies have demonstrated immunogenicity of the obtained protein and HI activity of the induced antibodies at a level meeting the FDA guidelines for vaccines against endemic and pandemic influenza. The H1 HA ectodomain fragment of the H1N1pdm09 virus was also expressed with the signal sequence in a bacterial expression system (Khurana S et al. 2010b). Purified and refolded protein (1-480 aa) comprising correctly folded monomers did not exhibit the oligomeric HA function (fetuin binding, erythrocyte agglutination). The correct conformation of the obtained HA ectodomain fragment, demonstrated using circular dichroism spectroscopy, as well as the presence of essential neutralizing conformational epitopes were confirmed by binding assays with antisera against the H1N1 virus and adsorption of neutralizing activity from these sera. Immunization studies in rabbits and ferrets with HA (1-480 aa) have shown that the protein is strongly immunogenic and the induced antibodies neutralize a homologous virus in vitro and inhibit its hemagglutinating activity. In a challenge experiment it was observed that vaccination with HA (1-480 aa) elicits protective immunity in ferrets against infection with a homologous influenza virus, manifested in that the animals exhibited substantially milder disease symptoms (temporary rise in temperature without weight loss) than non-vaccinated animals.

The H5 HA protein of HPAIV H5N1 with molecular weight of ~63 kDa was produced in the *E. coli* LMG strain (Horthongkham N et al. 2007). Mice immunized with purified rH5 responded with the production of antibodies recognizing the antigen used for vaccination and neutralizing the heterologous H5N1 virus in vitro. The H5 HA protein of HPAIV H5N1 was produced in *E. coli* BL21(DE3), expressed as a soluble fusion protein with the msyB chaperone with molecular weight of ~97 kDa (Xie Q M et al. 2009). The obtained msyB:HA protein was recognized in Western blot analysis by the H5N1-positive chicken sera. Monoclonal antibodies, obtained using the msyB:HA protein for mice immunization, detected AIV with high sensitivity, indicating the preservation of native HA epitopes in the recombinant protein. Vaccination of chickens with high msyB:HA doses induced HI antibody production in those animals, as well as conferred protection against HPAIV H5N1 infection under experimental conditions (survival rate—100%, moderate disease symptoms).

HA Purification and Refolding

The main challenge in work on obtaining HA in a bacterial expression system is the method of refolding, which would provide an antigen resembling viral HA, despite the fact that HA may be efficiently produced in bacterial cells as a non-glycosylated protein, additionally deprived of regions involved in higher order structure formation of the protein during virus propagation. The HA native structure of the vaccine antigen needs to be preserved, as majority of neutralizing epitopes are conformational antigenic sites (Wiley D C et al. 1981). Published results of the studies on HA proteins produced in a eukaryotic expression system demonstrate that, apart from the correct conformation of HA monomer, the protein oligomerization status also has a significant impact on the level and quality of immune response. In contrast to monomers, rHA trimers and oligomers of H5N1 virus from mammalian and baculovirus expression systems were effective in inducing high levels of neutralizing antibodies in mice (Wei C J et al. 2008). It was also shown that the HA protein of H3N2 virus, produced in a baculovirus expression system with a trimer-stabilizing modification, has a significantly stronger capacity to induce virus specific antibodies and HI antibodies in mice when compared to the unmodified protein form, which correlates with increased immunity against infection with a homologous influenza virus under experimental conditions (Weldon W C et al. 2010). Probably the monomeric form of antigen is less immunogenic than the trimer/oligomer forms of the same protein (Wei C J et al. 2008), but the oligomerization status may also influence the repertoire of induced antibodies (Wei C J et al. 2008, Weldon W C et al. 2010, Wilson I A and Cox N J 1990). In order to obtain soluble HA forming stable oligomeric structures, the proteins constituting the antigen ectodomain, produced in mammalian or insect cells, are expressed together with intentionally added foreign trimerizing sequences (Bosch B J et al. 2009, Loeffen W L et al. 2011, Wei C J et al. 2008, Weldon W C et al. 2010).

A majority of the HA proteins described above, i.e. the HA-1 subunit and its fragments, the ectodomain fragment and the full-length ectodomain, were expressed in *E. coli* in inclusion bodies as insoluble proteins with an affinity label, typically 6×His, exceptionally with another label, e.g. GST (Shen S et al. 2008), or without an affinity label (Liu G et al. 2011, 2012, Song L et al. 2008, 2009, Xuan C et al. 2011). The STF2:HA proteins were expressed as soluble and/or insoluble proteins (Liu G et al. 2011, 2012, Song L et al. 2008, 2009). By the attachment of a signal sequence for periplasmic expression to the N-terminus, in addition to the affinity label (6×His), a HA-1 subunit fragment expressible in soluble form was also obtained (Aguilar-Yáñez J M et al. 2010). However, the yield of this protein was 2 orders of magnitude lower than that of its refolded counterpart expressed in inclusion bodies. The HA protein of 63 kDa (Horthongkham N et al. 2007) and the 97-kDa msyB:HA fusion protein (Xie Q M et al. 2009) were expressed in *E. coli* with a histidine tag as soluble protein. The HA proteins contained in inclusion bodies, after they had been solubilized in standard denaturing buffers, were refolded either through slow or rapid dilution or on a column with a metal affinity chromatography bed. To ensure effective HA protein refolding, either L-arginine or L-arginine and oxidized/reduced glutathione were used in some refolding procedures. Fusion proteins with a histidine tag were purified by metal affinity chromatography. Proteins expressed with no affinity label were purified by standard chromatography procedures (Liu G et al. 2011, 2012, Song L et al. 2008, 2009, Xuan C et al. 2011). The process utilizing *E. coli* to produce a vaccine comprising the H1 hemagglutinin globular domain of the H1N1pdm09 virus was demonstrated by Sánchez-Arreola P et al. in their recent publication (2013).

To summarize, studies conducted to date on obtaining the HA antigen in a bacterial expression system focused primarily on proteins expressed in inclusion bodies, in particular those containing the HA-1 subunit or its fragments and intended for production of a serotype-specific vaccine (Aguilar-Yáñez J M et al. 2010, Chiu F F et al. 2009, DuBois R M et al. 2011, Jegerlehner A et al. 2013, Jeon S H i Arnon R 2002, Khurana S et al. 2010b, 2011a, 2011b, Liu G et al. 2011, 2012, Sánchez-Arreola P et al. 2013, Shen S et al. 2008, Skibinski D A et al. 2013, Song L et al. 2008, 2009, Verma S et al. 2012, Xuan C et al. 2011). In this way the HA proteins of serotypes: H1, H3, H5, H7 of pandemic, seasonal or prototype type A influenza viruses have been obtained. For most proteins based on the HA-1 subunit of HA conformational integrity has been documented by spectroscopy and/or reactivity assays with neutralizing antibodies. The capacity of the produced proteins to induce functional anti-HA antibodies has been shown in hemagglutination inhibition assays and in vitro influenza virus neutralization tests, while in challenge experiments they were shown to elicit protective immune response against influenza. This group of proteins is represented by the influenza vaccines tested in clinical trials and based on patented technologies: TLR (VaxInnate) and Qβ-VLPs (Cytos Biotechnology).

Another well-characterized bacterial HA protein is an HA ectodomain fragment expressed with a signal sequence (Khurana S et al. 2010b). The 1-480 aa protein was shown to possess the correct conformation, essential neutralizing conformational epitopes, the capacity to induce antibodies neutralizing a homologous virus in vitro and inhibiting its hemagglutinating activity, correlating with protection against influenza under experimental infection conditions. Properties of the full-length HA ectodomain synthesized without a signal sequence have not been fully documented (Biesova Z et al. 2009). The capacity of the protein to induce HI antibodies has been shown, although its potential to induce protective immune response by evaluating morbidity and survival rates of vaccinated animals after infection with influenza viruses has not been confirmed. Among the HA proteins expressed in bacteria in a soluble form (Horthongkham N et al. 2007, Xie Q M et al. 2009), the capacity to provide protective immune response in a challenge experiment has been shown only for the fusion protein with the msyB chaperone (Xie Q M et al. 2009).

Experiments with HA expression in bacterial cells have shown that the HA proteins of various lengths expressed in bacterial cells as soluble proteins or in the form of inclusion bodies may be valuable immunogens. The rHA-*E. coli* proteins may fold into correct conformation, despite not being glycosylated and even when they do not comprise regions involved in the formation of the protein native structure at viral infection, such as hydrophobic regions, i.e. the signal sequence and/or transmembrane domain. In the case of antigens with the dominant globular domain, the length of peptide fragments adjacent to the globular domain were shown to be crucial for its correct folding (Jegerlehner A et al. 2013, Song L et al. 2008, Xuan C et al. 2011). The rHA-*E. coli* proteins may also form functional oligomers, which is essential to induce protective immune response and has been demonstrated in studies on rHAs from both eukaryotic (Wei C J et al. 2008, Weldon W C et al. 2010) and prokaryotic expression systems (Khurana S et al. 2011b, Verma S et al. 2012).

Among the HA proteins produced in bacterial cells, also those with confirmed correct tertiary structure, the formation of functional oligomers has only been documented for specific HA-1 subunit fragments expressed with a signal sequence (Khurana S et al. 2010b, 2011a, 2011b, Verma S et al. 2012). Native HA oligomers induce high levels of neutralizing antibodies owing to the presence of trimer-dependent epitopes (Wilson I A, Cox N J 1990) and presumably also by limiting the accessibility of certain epitopes, e.g. those present on the interface between monomers (Wei C J et al. 2008, Weldon W C et al. 2010). Fragments of the HA-1 subunit of HA expressed without a signal sequence (Aguilar-Yáñez J M et al. 2010, DuBois R M et al. 2011, Jegerlehner A et al. 2013, Liu G et al. 2011, 2012, Skibinski D A et al. 2013, Song L et al. 2008, 2009, Xuan C et al. 2011), as well as the 1-480 aa fragment of ectodomain synthesized with a signal sequence (Khurana S et al. 2010b) were found in the form of monomers. The oligomerization capacity of other HA fragments produced in bacteria has not been studied. A change in the presentation of HA proteins based on the globular domain of HA was provided by the formation of HA dimers ($dHA_{63-286}$) involving a peptide linker (Sánchez-Arreola P et al. 2013) or using Qβ-VLPs as an antigen carrier (Jegerlehner A et al. 2013, Skibinski D A et al. 2013). Results of $dHA_{63-286}$ immunogenicity studies have not been published yet. The advantageous effect of conjugating gH proteins with Qβ-VLPs on the quality of immune response has been well documented.

Studies on production of HA proteins in bacterial inclusion bodies show that the basic requirement for obtaining an antigen with a correct conformation, capable of forming oligomeric structures, is to identify the protein fragment to be expressed, purified and refolded. The precise determination of the HA sequence for the production of vaccine antigen, particularly in the case of short protein fragments, often requires HA crystallographic screening and in silico analysis of its structure. Such analyses have been conducted in the course of projects, in which the globular domain was the dominant HA fragment in the vaccine (Aguilar-Yáñez J M et al. 2010, DuBois R M et al. 2011, Jegerlehner A et al. 2013, Song L et al. 2008, Xuan C et al. 2011). An essential requirement for the production of a valuable antigen is also to develop an effective refolding method, which has been clearly shown in comparative studies on antigen refolding using different procedures (Chiu F F et al. 2009). Most HA proteins overexpressed in bacterial cells were expressed with an affinity label and purified by metal affinity chromatography, which poses a problem of the final product quality associated with the presence of even trace amounts of metals.

Despite intensive research aiming at obtaining subunit vaccines against influenza, based on HA produced by genetic engineering, we still need to find an effective vaccine antigen as well as a technology facilitating efficient production of the vaccine antigen within a relatively short time, which would be an alternative for a lengthy procedure of conventional vaccine production.

The availability of such a technology is particularly significant in the case of influenza pandemic threat. The HPAIV H5N1 continues to be a current epidemiological problem with a pandemic potential, in view of the threat that the virus will acquire the capacity of direct transmission between humans. The emerging disease outbreaks among birds, often reaching the epizootic scale, cause high mortality among animals and require poultry culling, bringing heavy losses to the poultry industry. Furthermore, there is a continuous risk of reassortment of the circulating AI viruses with mammalian viruses, giving rise to new viral strains posing a threat to human and animal health.

Thus the aim of the invention is to provide a solution responding to the need for an inexpensive, safe vaccine against influenza, quickly and efficiently produced, particularly when facing a threat of pandemic or zoonosis, utilizing the potential of a bacterial expression system, verified in production of biopharmaceuticals, to produce a vaccine antigen.

The object of the invention is an isolated and purified influenza virus (IV) hemagglutinin (HA) polypeptide, consisting of a HA-1 subunit, forming the viral HA globular domain with a binding site to the host cells receptors and involved in the formation of the native HA stalk domain, and a HA-2 subunit fragment with an N-terminal fusion peptide, forming the native HA stalk domain, while the polypeptide is deprived of sequences present in the precursor (HA0) and/or mature viral HA form: the N-terminal signal peptide and the C-terminal protein region downstream of the bromelain cleavage site, in which the transmembrane and cytoplasmic domains are present.

Preferably, the influenza virus is HPAIV H5N1.

Preferably, the influenza virus is the HPAIV H5N1 A/swan/Poland/305-135V08/2006 strain (EpiFlu Access no. EPI156789).

Preferably, the polypeptide is comprised of HA 17-522 aa consisting of the HA-1 (17-340 aa) subunit and a portion of the HA-2 subunit (347-522 aa) with the N-terminal fusion peptide and a retained C-terminal bromelain cleavage site (521-522 aa).

Preferably, the polypeptide consists of an amino acid sequence, structurally corresponding to the HA 17-522 aa sequence of the H5N1 strain of avian influenza virus (AIV) A/swan/Poland/305-135V08/2006 (EpiFluDatabase Accession No. EPI156789).

Preferably, the polypeptide comprises a deletion of basic amino acids: lysine (K) and arginine (R) from the cleavage site between the protein HA-1 and HA-2 subunits (ΔRRRKKR, Δ341-346 aa).

Preferably, the polypeptide has the SEQ ID NO: 1 amino acid sequence or an amino acid sequence corresponding to SEQ ID NO: 1.

Preferably, the polypeptide has the SEQ ID NO: 2 amino acid sequence or an amino acid sequence corresponding to SEQ ID NO: 2.

Preferably, the polypeptide is produced in a prokaryotic expression system.

Preferably, the polypeptide is produced in *E. coli*.

Preferably, the polypeptide is expressed in the form of inclusion bodies.

A further object of the invention is a composition comprising a carrier and the said polypeptide in an effective amount to elicit immune response and/or treat an influenza virus infection.

Preferably, the carrier is an adjuvant stimulating humoral and/or cellular response, selected from the group comprising mineral salts, oil emulsions, mycobacterial products, saponins, synthetic products and cytokines.

Preferably, the adjuvant is aluminium hydroxide, chitosan salts, MF59, AS03, ISCOMATRIX or PROTASAN™ UP G 113 (NovaMatrix/FMC Corp.).

Preferably, the composition is administered subcutaneously, intradermally, intramuscularly or mucosally, including intranasally, via the gastrointestinal tract, and in the case of bird immunization also conjunctivally, naso-conjunctivally, in ovo.

A further object of the invention is the composition as defined above for prophylactic vaccination of humans or for immunization of birds against influenza virus, particularly of laying hens in commercial flocks and breeding flocks of laying hens and broilers.

Preferably, the influenza virus is the HPAIV H5N1 avian influenza strain.

Another object of the invention is an antibody specifically binding to the polypeptide, as defined above.

A further object of the invention is the method of obtaining a polypeptide inducing functional antibodies against influenza virus (IV) hemagglutinin (HA), comprising:

a) isolation of a polypeptide from the naturally occurring influenza virus (IV) hemagglutinin (HA) protein, consisting of:
  i. an HA-1 subunit, forming the viral HA globular domain with a protein binding site to the host cells receptors and involved in the formation of the native HA stalk domain, and
  ii. an HA-2 subunit fragment with the N-terminal fusion peptide, forming the native HA stalk domain, while the polypeptide is deprived of sequences present in the precursor (HA0) and/or mature viral HA form: the N-terminal signal peptide and the C-terminal protein region downstream of the bromelain cleavage site, in which the transmembrane and cytoplasmic domains are present.

b) transformation of prokaryotic cells with an expression vector comprising a nucleic acid encoding the polypeptide of a);

c) culture of transformed prokaryotic cells producing the polypeptide of a);

d) isolation and solubilization of inclusion bodies;

e) refolding and purification of the said produced polypeptide.

Preferably, the influenza virus is HPAIV H5N1.

Preferably, the polypeptide is HA 17-522 aa, consisting of the HA-1 (17-340 aa) subunit and a fragment of the HA-2 subunit (347-522 aa) with the N-terminal fusion peptide and a retained C-terminal bromelain cleavage site (521-522 aa).

Preferably, the polypeptide consists of an amino acid sequence structurally corresponding to the HA 17-522 aa sequence from the H5N1 strain of the avian influenza virus (AIV) A/swan/Poland/305-135V08/2006 (EpiFluDatabase Accession No. EPI156789).

Preferably, the polypeptide comprises a deletion of basic amino acids: lysine (K) and arginine (R) from the cleavage site between the protein HA-1 and HA-2 subunits (ΔRRRKKR, Δ341-346 aa).

Preferably, the polypeptide has the SEQ ID NO: 1 amino acid sequence.

Preferably, the polypeptide has the SEQ ID NO: 2 amino acid sequence.

Preferably, the prokaryotic cells are bacterial cells, particularly *E. coli*.

Preferably, the isolated inclusion bodies are solubilized in the DRCI buffer (50 mM TrisHCl, pH 8.0; 8 M urea; 10 mM beta-mercaptoethanol; 0.01% Triton X-100).

Preferably, the polypeptide solution obtained as a result of inclusion bodies solubilization is purified on a DEAE Sepharose Fast Flow bed column (Amersham Pharmacia Biotech AB).

Preferably, the polypeptide is refolded by dilution in BR buffer (40 mM Tris-HCl pH 8.0; 100 mM NaCl).

Preferably, after refolding the polypeptide is purified on a Phenyl Sepharose 6 Fast Flow High Sub column (Amersham Pharmacia Biotech AB).

The influenza virus (IV) hemagglutinin (HA) protein according to the invention is a part of naturally occurring hemagglutinins of various serotypes and antigenic variants and constitutes a fragment of the protein ectodomain, containing sequences which in the native protein form epitopes for neutralizing antibodies, acting via two different mechanisms of infection inhibition, described for IV.

In one embodiment, the HA protein according to the invention is HPAIV H5N1 H5 HA. However, this does not impose limitations for the serotype or strain of the virus that the vaccine containing the HA protein according to the invention may target. The protein according to the invention may be isolated from all HA serotypes and antigenic variants, or combine HA fragments of different serotypes or antigenic variants, e.g. as a consensus sequence.

The presence of a HA-1 subunit and a HA-2 subunit fragment in the HA protein according to the invention results in the antigen containing sequences that in the native protein form epitopes for neutralizing antibodies that act via two mechanisms of infection inhibition, described for influenza viruses, i.e. blocking the binding of influenza viruses to host cells (HA-1), and inhibiting the fusion of the virus lipid envelope with the endosomal membrane of host cells (HA-2), and thus the penetration of pathogens into host cells. Retaining in the HA protein, according to the invention, of a long fragment of the HA-2 subunit, which is involved in formation of oligomeric structures during viral HA synthesis, creates advantageous conditions for optimal protein refolding.

The HA protein according to the invention has properties distinguishing it from other bacterial proteins—the HA sequence to be expressed was obtained by removing immunologically inert protein regions: the signal sequence, the transmembrane domain and the cytoplasmic domain, as well as the C-terminal protein ectodomain fragment downstream of the bromelain cleavage site, and in the case of highly pathogenic (HP) IV strains (HP HPAIV) also the basic amino acids from the cleavage site between the protein HA-1 and HA-2 subunits.

Removal of the HA hydrophobic regions, i.e. the signal peptide and the transmembrane domain, enables efficient HA expression in bacterial cells and is additionally justified by the fact that the signal peptide is not found in the mature HA protein and the removed fragments are not essential for antigenicity and immunogenicity of the protein. Since the protein does not contain a majority of native HA hydrophobic sequences, it is readily soluble in aqueous solutions and may be efficiently expressed in prokaryotic cells.

The HA protein of the HPAIV strains does not contain a sequence rich in basic amino acids: lysine (K) and arginine (R), susceptible to digestion by proteolytic enzymes of the trypsin and subtilisin family, which prevents cleavage and degradation to subunits during the production process.

The influenza virus HA protein, in a particular embodiment of the invention, is the HPAIV H5N1 H5 HA protein obtained by overexpression in E. coli in the form of inclusion bodies and constitutes an H5 HA ectodomain fragment (17-522 aa), soluble in aqueous solutions, deprived of a cleavage site susceptible to digestion by proteolytic enzymes (ΔRRRKKR). The H5 HA (17-522 aa) protein substantially corresponds to the HA particles released from influenza viruses using bromelain—BHA (bromelain-released hemagglutinin).

The HPAIV H5N1 H5 HA protein was produced based on the sequence of the Polish virus isolate: A/swan/Poland/305-135V08/2006(H5N1) (EpiFluDatabase Accession No. EPI156789). The Polish AIV isolate protein regions were identified by comparing its amino acid sequence with the HA sequence of the A/Hong Kong/156/97(H5N1) strain (GenBank Accession No. AAC32088). Individual HPAIV A/swan/Poland/305-135V08/2006(H5N1) HA regions are formed by the following amino acid sequences:
the signal region—1-16 aa;
the HA-1 subunit—17 . . . 345;
the HA-2 subunit—347 . . . 568;
the transmembrane domain—532 . . . 552;
the cytoplasmic domain—553 . . . 568.
the cleavage site for trypsin and subtilisin protease family, rich in basic amino acids—QGERRRKKRG (SEQ ID NO: 6)—338 . . . 347 aa;
the bromelain cleavage site—G-521 . . . V-522.

In the case of H5 HA of the Polish HPAIV isolate, the BHA molecule is formed by the 17-521 amino acids of the viral HA. Isolated BHA molecules constitute a non-infectious immunogen capable of inducing immune response, still utilized to produce reference antisera for single radial immunodiffusion (SRID) assay to determine vaccine potency against influenza (Khurana S et al. 2011a). Determination of the HA protein sequence according to the invention, for different type A influenza virus protein variants and serotypes for the vaccine antigen production, requires identification of the site where HA is cleaved from viral particles by bromelain, and protein crystallographic studies and their in silico structure analysis are not required.

Sequences structurally corresponding to the amino acid sequence of the selected HA polypeptide contain higher order homologous protein structures and as a result also the HA protein characteristic regions with specific properties and functions. Structurally corresponding sequences do not necessarily correspond to the linear amino acid sequence, thus amino acid numbering of the structurally corresponding protein fragments may differ.

For instance, the amino acid sequence structurally corresponding to the 17-522 aa HA sequence of the avian influenza virus (AIV) A/swan/Poland/305-135V08/2006 H5N1 strain consists of a HA-1 subunit, forming the viral HA globular domain with the binding site to the host cells receptors and is involved in the formation of the native HA stalk domain, and a HA-2 subunit fragment with the N-terminal fusion peptide, forming the native HA stalk domain, while the polypeptide is deprived of sequences present in the precursor (HA0) and/or mature viral HA form, i.e. the N-terminal signal peptide and the C-terminal protein region downstream of the bromelain cleavage site, in which the transmembrane and cytoplasmic domains are found.

To date the HA protein according to the invention has not been produced in a bacterial expression system, nor it has been studied and described as an effective antigen for vaccines against influenza, in particular against HPAIV H5N1.

In the preferred variants for the production of proteins according to the invention the pIGKesHA17522Δ, pDBHa17522Δ vectors are used, containing the HA17522Δ gene encoding the HA 17-522 aa protein of the HPAIV H5N1 A/swan/Poland/305-135V08/2006 strain (EpiFluDatabase Accession No. EPI156789) with deletion of lysine (K) and arginine (R) residues from the cleavage site (ΔRRRKKR, Δ341-346 aa), optimized for expression in E. coli and providing a high level of the antigen expression. Bacterial strains transformed with the aforementioned vectors are E. coli BL21(DE3) and E. coli Z 0526, respectively.

Purified and refolded HA (17-522 aa, ΔRRRKKR (SEQ ID NO: 2) protein from the HPAIV H5N1 strain, obtained by overexpression in bacteria E. coli in inclusion bodies—rH5-E. coli exhibits key properties of the vaccine HA, as it retains the neutralizing epitopes, recognized by antibodies specific towards the H5 serotype of HA and by hemagglutination inhibiting (HI) antibodies and is present, at least partly, in the form of oligomers.

In contrast to the 1-480 aa ectodomain found in the form of monomers, the rH5-E. coli forms functional oligomers in the absence of foreign trimerizing sequences, possibly mediated by the HA-2 subunit fragment. The HA protein oligomerization has an advantageous effect on immune response quality, while it also reduces the effective antigen dose and hence lowers the unit cost of the influenza vaccine.

The obtained rH5-E. coli protein induces in chickens the production of IgY antibodies, specific towards H5 HA, the antibodies active in the FLUAc H5 (IDVet) assay and inhibiting hemagglutination by the homologous HPAIV H5N1 and the heterologous LPAIV H5N2. The administration of HA as a vaccine antigen enables detection of infected birds within the population of vaccinated birds using differentiating serological tests, detecting antibodies against AIV proteins other than the antigen used for immunization of animals. Providing the potential for DIVA (differentiation of infected from vaccinated animals) is the basic requirement for vaccination against avian flu (Suarez D L 2005).

The vaccine against influenza contains the HA protein according to the invention, an adjuvant or adjuvants approved in human and animal immunization specific to the route of administration, as well as other components, e.g. conventional components of pharmaceutical formulations.

The vaccine contains hemagglutinin of a specific serotype and antigen variant (monovalent vaccine), or hemagglutinins of different serotypes or antigen variants (polyvalent vaccine), or HA with a sequence of different antigen variants of a specific serotype (serotype-specific vaccine with increased protectivity against viruses of various clades), or HA with a sequence of various serotypes, eg. a consensus (universal) vaccine.

The vaccine may comprise the above-mentioned HA proteins physically associated with peptides or polypeptides, including a label, a peptide with a protease cleavage site, a trimerizing sequence, immunomodulators or other antigens.

In a preferred embodiment of the invention, the vaccine against influenza contains the rH5-*E. coli* protein, aluminium hydroxide as an adjuvant, and elicits production of antibodies specific to H5 HA in subcutaneously vaccinated chickens, including functional antibodies active in the FLUAc H5 (IDVet) assay and in HI tests with homologous HPAIV H5N1 and heterologous LPAIV H5N2, as well as provides protection against infection with influenza viruses and reduces virus shedding in the experimental infection tests.

In a preferred embodiment of the invention, the vaccine contains the rH5-*E. coli* protein and PROTASAN™ UP G 113 (NovaMatrix/FMC Corp.) as an adjuvant, and exhibits the capacity to enhance production of antibodies specific to H5 HA when administered intranasally to chickens primed by subcutaneous administration of rH5-*E. coli* with aluminium hydroxide as an adjuvant, including functional antibodies active in the FLUAc H5 (IDVet) assay and in the HI test with heterologous LPAIV H5N2.

In the method of HA protein production according to the invention, the antigen is expressed in inclusion bodies of bacteria transformed using expression vectors, in which the protein coding sequence is optimized for a bacterial expression system. In the method of HA protein production according to the invention, a highly efficient and effective refolding method was applied without the use of amino acids: L-arginine, reduced and oxidized glutathione, frequently contained in buffers for bacterial rHA refolding, thus lowering the cost of vaccine HA production. In contrast to most bacterial rHAs, which are purified using metal affinity chromatography, standard chromatography methods are used in the method of HA production according to the invention. Accordingly, the presence of metal ions in the final product, produced by the method according to the invention, is not subject to assessment and quality evaluations may be performed using the procedures developed for biopharmaceuticals, commonly produced in a bacterial expression system.

The essence of the invention is also a method of eliciting protective immune response. The method of eliciting immune response comprises vaccinations using the HA protein obtained by the method according to the invention, by parenteral administration of the antigen, including subcutaneous, intradermal, intramuscular or mucosal, including intranasal, via the gastrointestinal tract, and in the case of bird immunization also conjunctivally, naso-conjunctivally, in ovo or any other method approved in bird vaccination; performed employing identical or different administration routes for the vaccine antigen in a given vaccination cycle; by administrating the antigen with adjuvants approved in human and animal immunization and specific to the route of administration; through mucosa in mass vaccinations. The immunization regimen for humans or a particular animal species using the protein obtained by the method of the invention is optimized towards increased efficacy, the range of the induced cross-immunity and reduction of the effective dosage. Optimization of the immunization regimen involves: the level and number of doses, the type of adjuvant used and the route of administration as well as the interval between the doses. The method of eliciting immune response induces production of antibodies against HA, including functional antibodies, such as serotype-specific neutralizing antibodies, antibodies inhibiting hemagglutination by influenza viruses, antibodies neutralizing influenza viruses in vitro, provides protection against influenza, reduces virus shedding and viral transmission to humans or animals susceptible to IV infection.

In the example solutions the method of eliciting immune response comprises subcutaneous immunization of broiler-type chickens with two 25 μg-doses of the rH5-*E. coli* protein with aluminium hydroxide as an adjuvant, at an interval of 4 weeks, as substantially more effective in inducing IgY antibodies specific to H5 HA, antibodies active in HI tests with the homologous HPAIV H5N1 and the heterologous LPAIV H5N2, while in the case of induction of antibodies active in the FLUAc H5 (IDVet) assay as the only effective one in comparison to immunization at a 2-week interval.

The subcutaneous immunization of broiler-type chickens repeated using 25 μg of the rH5-*E. coli* protein with aluminium hydroxide as an adjuvant, at an interval of 4 weeks, elicits production of IgY antibodies specific to H5 HA, antibodies active in the FLUAc H5 (IDVet) assay and in HI tests with the homologous HPAIV H5N1 and the heterologous LPAIV H5N2 (titer ≥1:8) in 100%, 37.5%, 75% and 62.5% animals, respectively.

The subcutaneous immunization of laying-type chickens with the rH5-*E. coli* protein at doses of 5, 10, 15 and 25 μg with aluminium hydroxide as an adjuvant, repeated twice at an interval of 4 or 6 weeks, elicits production of IgY antibodies specific to H5 HA, antibodies active in the FLUAc H5 (IDVet) assay and in the HI test with the heterologous LPAIV H5N2 (protection titer ≥1:16) in 100%, 74%±16.5 and 85%±14 animals, respectively.

Intranasal administration of a booster dose of the vaccine containing 20 μg of rH5-*E. coli* and PROTASAN™ UP G113 (NovaMatrix/FMC Corp.) as an adjuvant, 4 weeks after subcutaneous immunization using 25 μg of rH5-*E. coli* with aluminium hydroxide, enhances production of IgY antibodies against H5 HA, in 10 out of 15 vaccinated animals, and in some of them also of functional antibodies against H5 HA: active in the FLUAc H5 (IDVet) assay and in the HI test with the heterologous LPAIV H5N2.

BRIEF DESCRIPTION OF FIGURES AND TABLES

FIG. 1 shows the nucleotide sequence of hemagglutinin from avian influenza virus A/swan/Poland/305-135V08/2006(H5N1)

FIG. 2 shows a map of the pIGCmT7Kes plasmid, where ARG t-RNA—arginine tRNA gene for the AGA and AGG codons; ORI—replication origin; CatA1—chloramphenicol acetyltransferase encoding gene, T7 promoter—promoter from T7 phage, Transcription stop—termination of transcription from the T7 phage promoter; Stop+Term+APH—nucleotide fragment of a cassette, where Stop—translation stop codon; Term—tryptophan terminator sequence; APH—modified sequence encoding aminoglycoside 3'-phosphotransferase.

FIG. 3 shows the HA17522 coding sequence, inserted into pIGCmT7Kes in sites resulting from NdeI and XhoI restriction enzymes digestion. Altered codons marked in bold, deleted sequence HAΔ underlined, sequence fragments: atg—start codon, taa—stop codon marked in bold.

FIG. 4 shows pIGKesHA17522Δ with a cloned HA17522Δ insert

FIG. 5A shows the recombinant HA17522 (rH5) amino acid sequence (SEQ ID NO: 1). Amino acids deleted from the HA17522 sequence to obtain HA17522Δ are underlined.

FIG. 5B the HA17522 ΔRRRKKR sequence (SEQ ID NO: 2).

Figure 6:
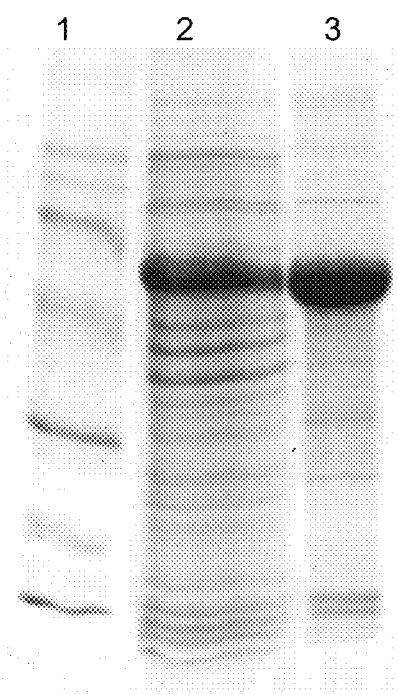

FIG. 6 shows electrophoretic separation of isolated inclusion bodies containing rH5 (17-522 aa, ΔRRRKKR (SEQ ID NO: 2)) from *E. coli* B121(DE3) strain. Lanes: 1) protein mass standard LMW 14.4 kDa, 20.1 kDa, 30.0 kDa, 43.0 kDa, 67.0 kDa, 94.0 kDa, 2) lysate of bacterial cells expressing rH5-*E. coli* (17-522 aa, ΔRRRKKR), 3) preparation of inclusion bodies containing rH5-*E. coli* (17-522 aa, ΔRRRKKR (SEQ ID NO: 2)).

Figure 7:
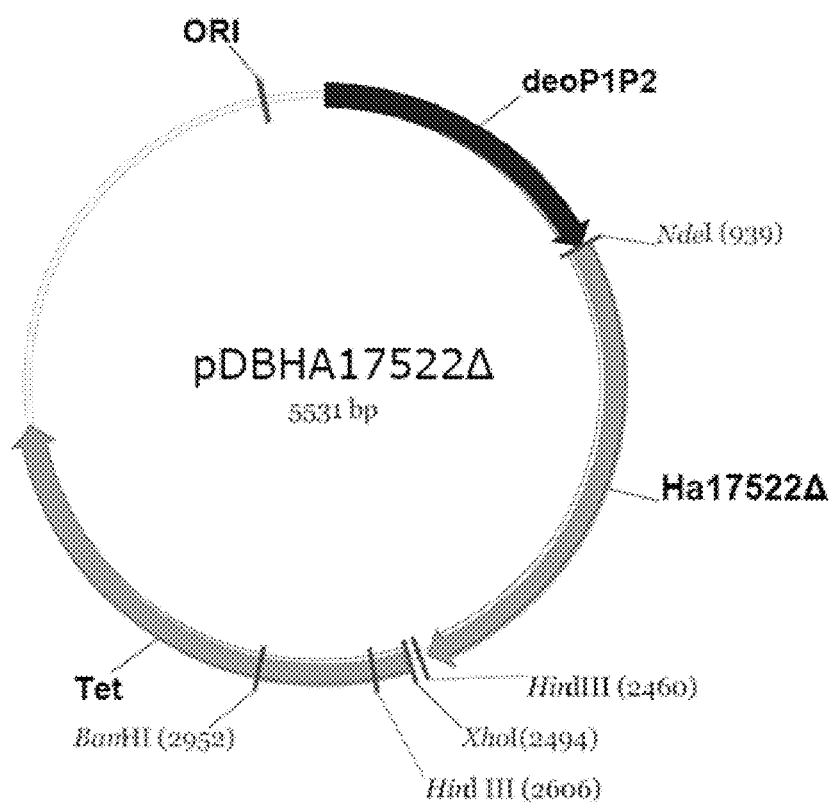

FIG. 7 shows the pDBHa17522Δ vector with a cloned HA17522Δ insert

Figure 8:
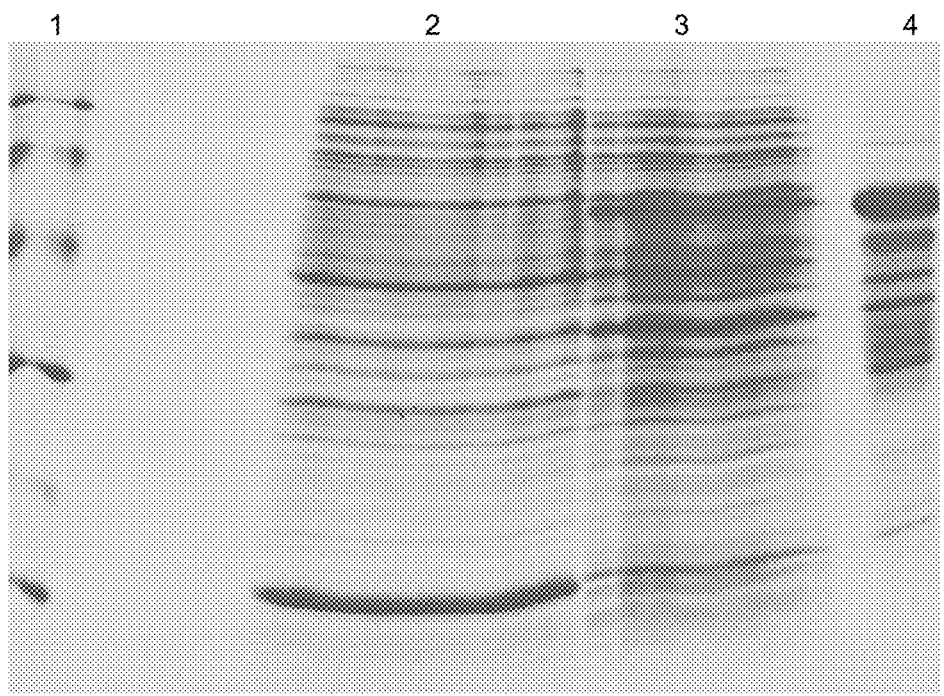

FIG. 8 shows electrophoretic separation of isolated inclusion bodies containing rH5 (17-522 aa, ΔRRRKKR (SEQ ID NO: 2)) from *E. coli* Z0526. Lanes: 1) protein mass standard LMW 14.4 kDa, 20.1 kDa, 30.0 kDa, 43.0 kDa, 67.0 kDa, 94.0 kDa, 2) supernatant after centrifugation of isolated inclusion bodies, 3) lysate of bacterial cells expressing rH5-*E. coli* (17-522 aa, ΔRRRKKR (SEQ ID NO: 2)), 3) preparation of inclusion bodies containing rH5-*E. coli* (17-522 aa, ΔRRRKKR (SEQ ID NO: 2)).

FIG. 9 shows pIBAHa17522Δ with a cloned HA17522Δ insert

FIG. 10A-10B shows chromatographic images from successive steps of rH5-*E. coli* protein purification: FIG. 10a—separation on the DEAE Sepharose FF column, b—separation on the Phenyl Sepharose FF column. AU—UV measurement unit, nS/cm—conductivity unit.

Figure 11:
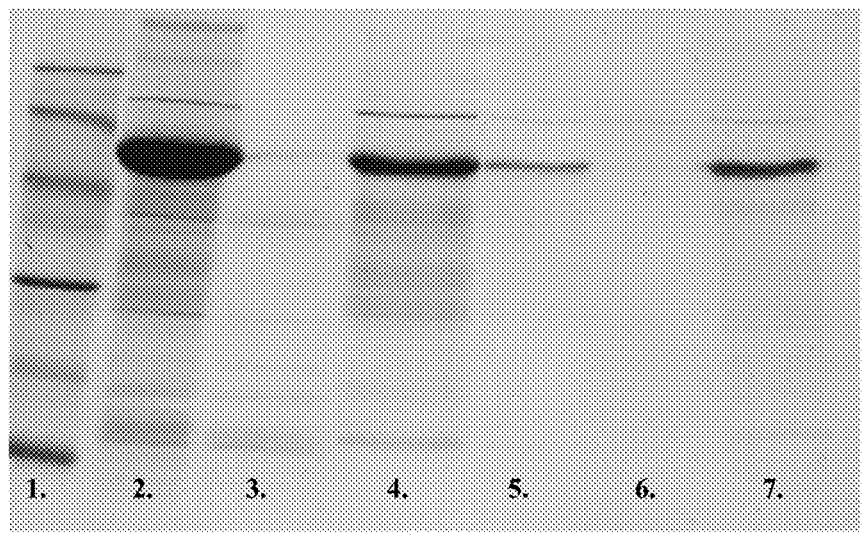

FIG. 11 shows an electropherogram from successive steps of rH5-*E. coli* protein purification, where the numbers used indicate: 1—LMW standard (successive bands with masses of: 94 kDa; 67 kDa; 43 kDa; 30 kDa; 20.1 kDa; 14.4 kDa); 2—inclusion bodies solubilized in DRCI buffer; 3—proteins not bound to the DEAE Sepharose Fast Flow bed; 4—proteins eluted from the DEAE Sepharose Fast Flow bed; 5—proteins after refolding by dilution; 6—proteins not bound to the Phenyl Sepharose Fast Flow bed; 7—proteins eluted from the Phenyl Sepharose Fast Flow bed.

Figure 12:
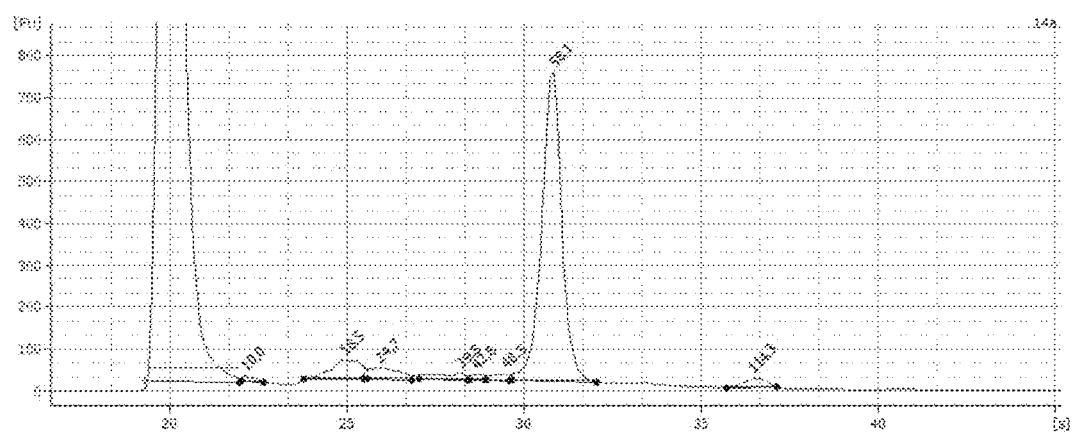

FIG. 12 shows an example electropherogram from the analysis of final rH5-*E. coli* preparation on the Agilent 2100 Bioanalyzer using High Sensitivity Protein 250 kit chips, where FU—denotes fluorescence level; s—denotes migration time; the first peak with a high fluorescence level originates from the lower internal marker; numbers above peaks indicate protein mass in kDa determined accurate to +/−10%.

Figure 13:
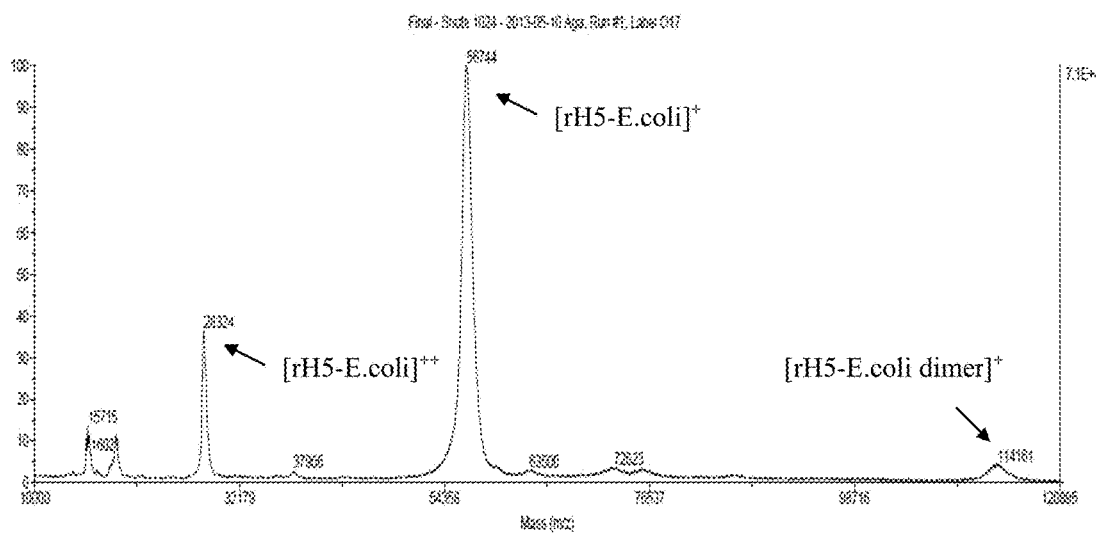

FIG. 13 shows a mass spectrum of an example rH5-*E. coli* preparation.

Figure 14:
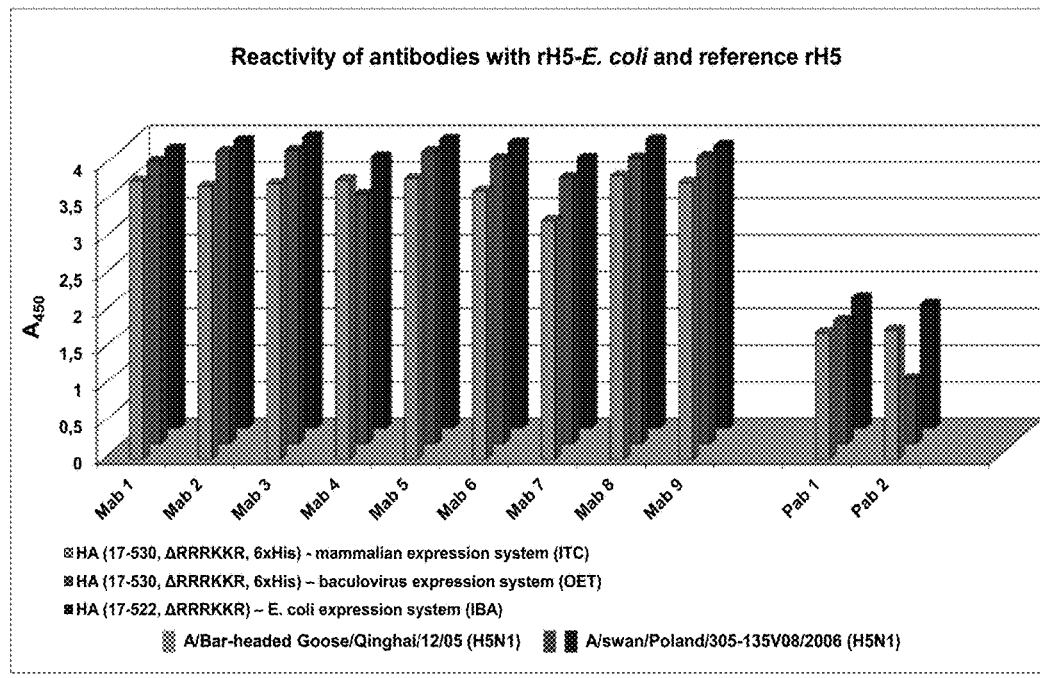

FIG. 14 shows results of immunoreactivity assays of monoclonal (Mab) and polyclonal (Pab) antibodies against HA with rH5-*E. coli*. The HA proteins (17-530 aa, ΔRRRKKR, 6×His), produced on the basis of HA sequence from the A/swan/Poland/305-135V08/2006(H5N1) strain in a baculovirus expression system (Oxford Expression Technologies) and from the A/Bar-headed Goose/Qinghai/12/05 (H5N1) strain in a mammalian expression system (Immune Technology Corp.), were reference antigens. Commercially available Mabs (1, 2, 6, 7, 9, Acris Antibodies; Mab 3, ABR/Thermo Scientific; Mab 4, 5, 8, USBiological) and Pabs against the HA-1 (Pab 1) or HA-2 subunit (Pab 2) of HA (Immune Technology Corp.) were used in the assay. Analyses were conducted by ELISA on MediSorp plates (NUNC).

Figure 15:
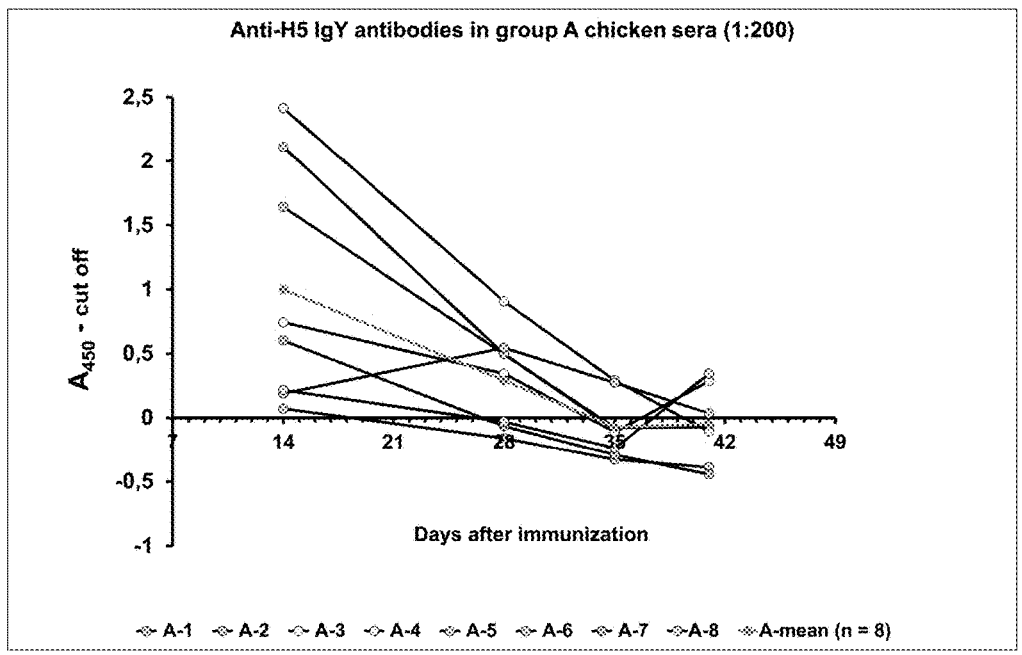
Figure 31:
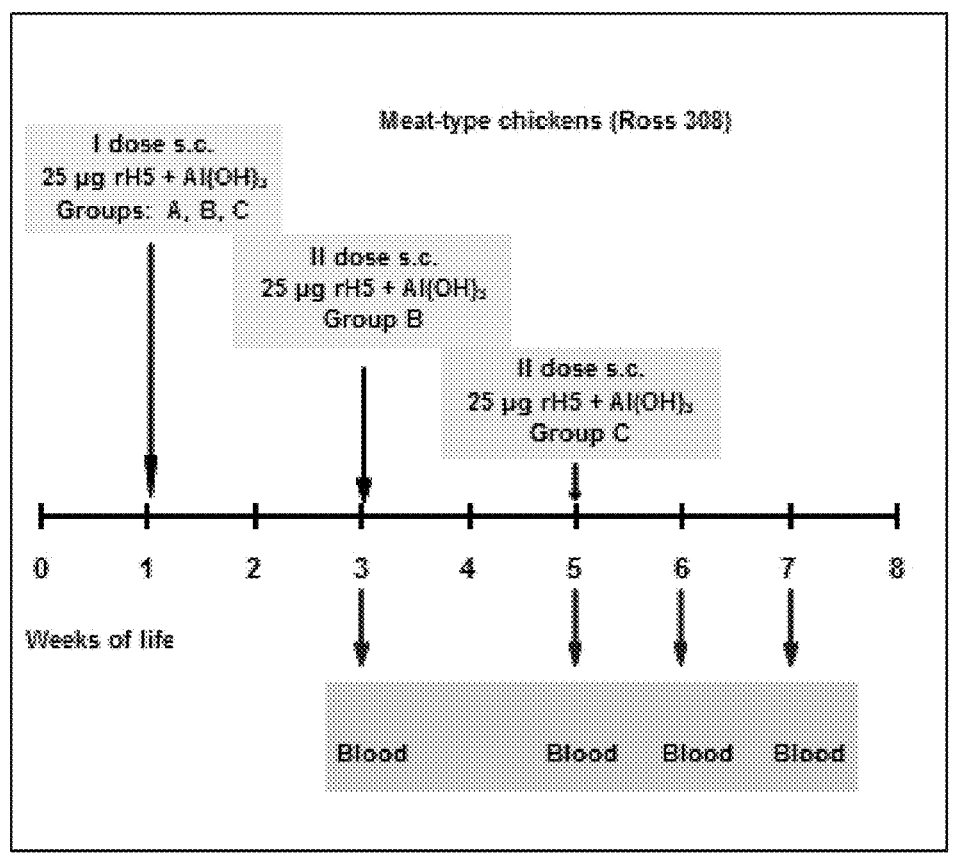

FIG. 15 shows results of the indirect ELISA (H5-ELISA) detecting IgY antibodies against H5 in chicken serum, obtained for individual animals vaccinated subcutaneously using one 25 μg-dose of rH5-*E. coli* with aluminium hydroxide as an adjuvant. Results for the vaccinated group (A) are shown as signal values ($A_{450}$) exceeding cut off values ($A_{450}$—cut off). The analyses were conducted in broiler-type chickens. Vaccinations and sample collection from the experimental (group A) and control animals (group K) were performed according to regimen A (FIG. 31).

Figure 16:
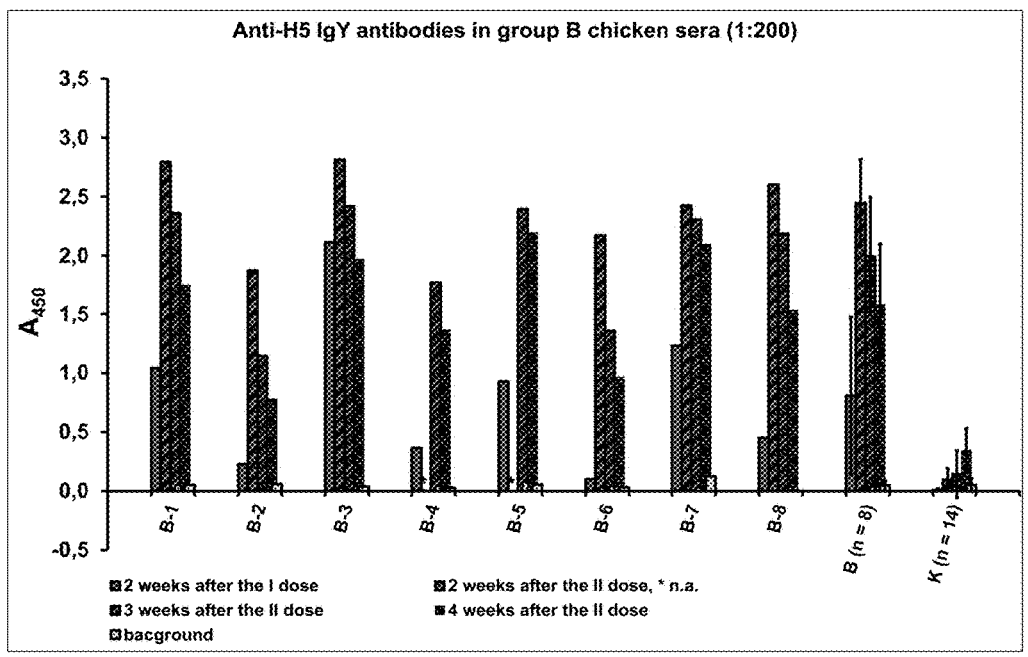

FIG. 16 shows results of the indirect ELISA (H5-ELISA) detecting IgY antibodies against H5 in chicken sera, obtained for individual animals vaccinated twice, subcutaneously at a 2-week interval with a 25 μg-dose of rH5-*E. coli* and aluminium hydroxide as an adjuvant. Results for the vaccinated (B) and the control (K) groups are shown as mean $A_{450}$±SD. Studies were conducted in broiler-type chickens. Vaccinations and sample collection from experimental (group B) and control (group K) animals were performed according to regimen A (FIG. 31).

Figure 17:
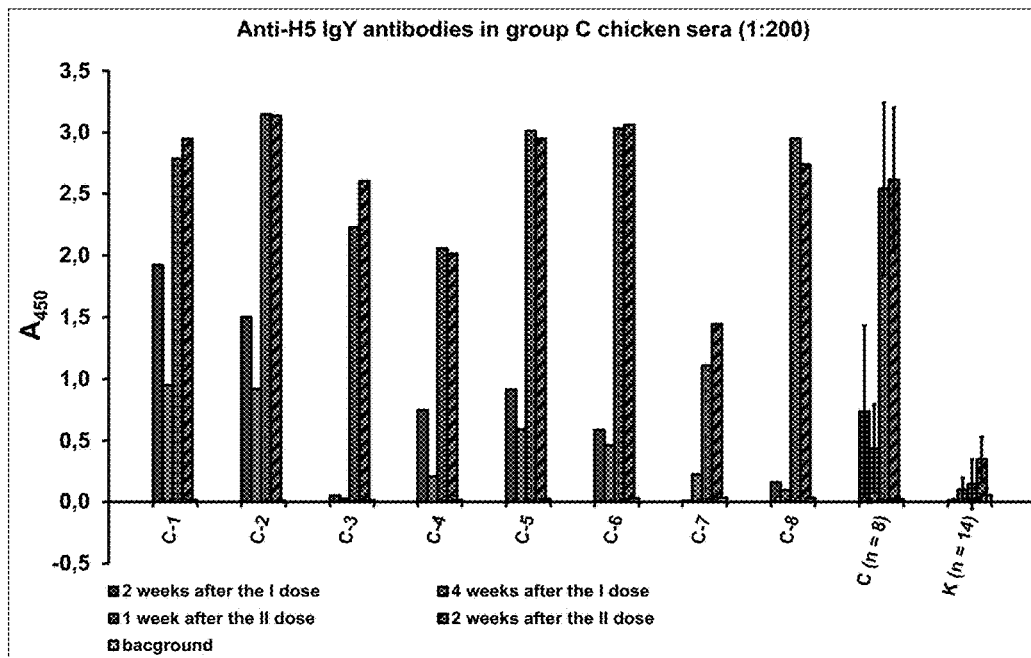

FIG. 17 shows results of the indirect ELISA (H5-ELISA) detecting IgY antibodies against H5 in chicken sera, obtained from individual animals vaccinated twice, subcutaneously at a 4-week interval using a 25 μg-dose of rH5-*E. coli* with aluminium hydroxide as an adjuvant. Results for the vaccinated (C) and the control (K) groups are shown as mean $A_{450}$±SD. Studies were conducted in broiler-type chickens. Vaccinations and sample collection from experimental (group C) and control (group K) animals were performed according to regimen A (FIG. 31).

Figure 18:
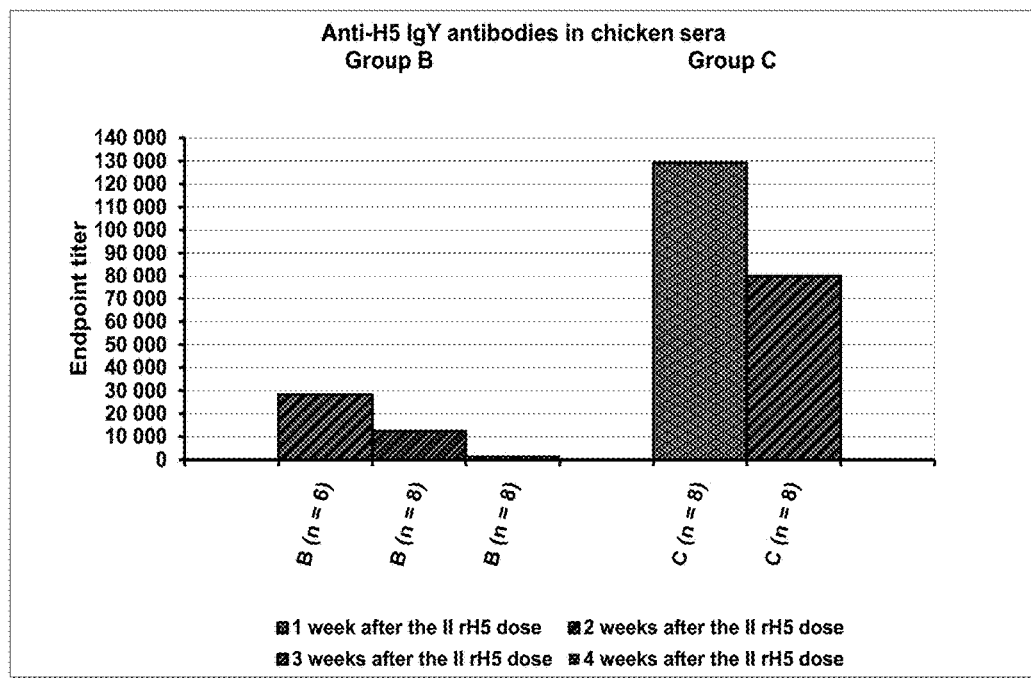

FIG. 18 shows results of endpoint titer determination for IgY antibodies against H5 in sera of chickens vaccinated with rH5-*E. coli* subcutaneously twice at a 2-week (group B) or a 4-week interval (group C) with 25 μg of the antigen per dose and aluminium hydroxide as an adjuvant. Sera obtained from blood collected 2, 3 or 4 weeks (group B), or 1 or 2 weeks (group C) after booster dose administration, as well as those prepared in parallel in the control group (group K) were combined and titrated using the indirect ELISA (H5-ELISA). Studies were conducted in broiler-type chickens. Vaccinations and sample collection from experimental (groups: B, C) and control animals (group K) were performed according to regimen A (FIG. 31).

Figure 19:
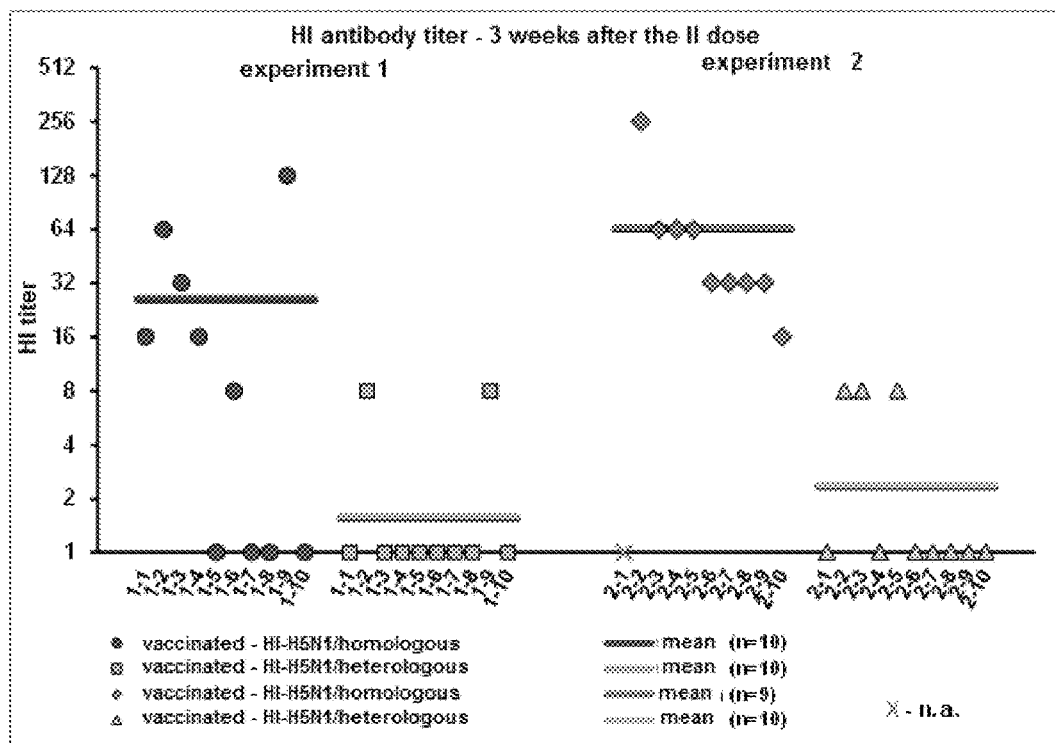

FIG. 19 shows results of HI tests obtained for laying-type SPF chickens in a challenge experiment. Animals were immunized subcutaneously twice at a 4- or 4½-week interval with 25 μg of rH5-*E. coli* and aluminium hydroxide as an adjuvant, according to regimens B and C. Serum samples collected 3 weeks after administering the booster dose of the antigen, i.e. directly before homologous (experiment 1) or heterologous (experiment 2) HPAIV H5N1 infection, were analyzed. The HI tests were conducted at HIU 1:8 with homologous and heterologous HPAIV H5N1 as antigens, described in line-up B. Results of analyses with two HI tests are demonstrated as the HI antibody titer in serum of individual animals and as a mean HI antibody titer in each of studied groups. The titer value <1:8 is marked as the 1.0 value on the chart.

Figure 20:
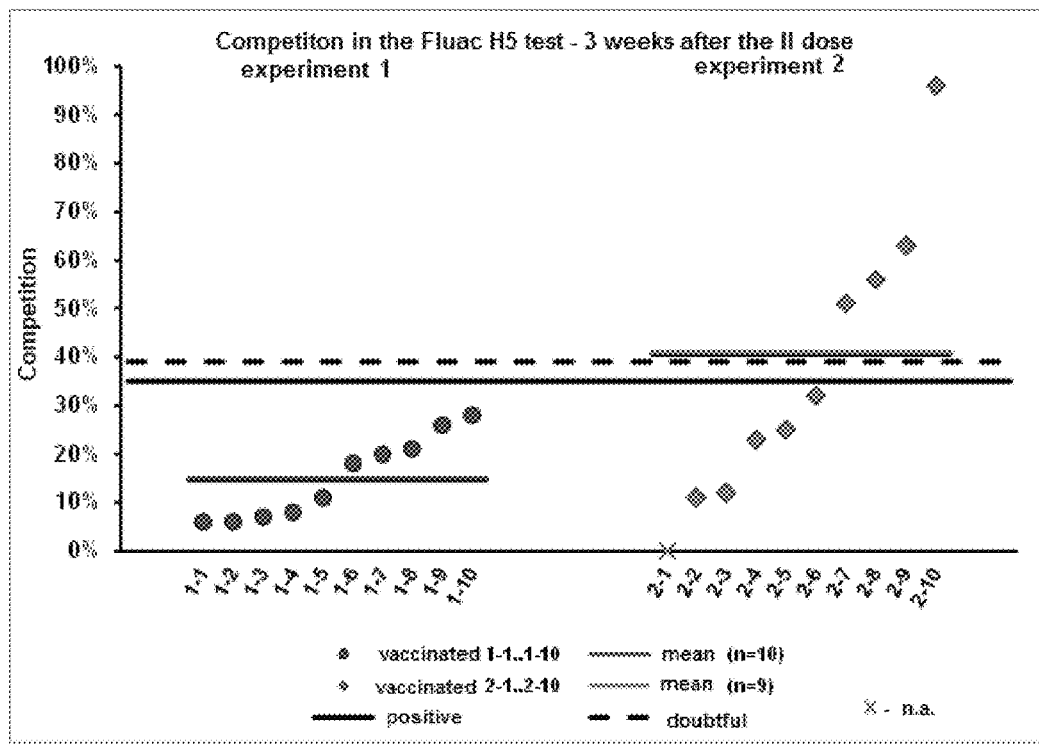

FIG. 20 shows results of the FLUAc H5 (IDVet) test for detection of antibodies against H5 in bird sera, obtained for laying-type SPF chickens in a challenge experiment. Animals were immunized subcutaneously twice at a 4- or 4½-weeks interval with 25 μg of rH5-*E. coli* and aluminium hydroxide as an adjuvant, according to regimens B and C. Serum samples collected 3 weeks after administering the booster dose of the antigen, i.e. directly before homologous (experiment 1) or heterologous (experiment 2) HPAIV H5N1 infection, were analyzed. Results of analyses are presented as the competition value for serum samples of individual animals expressed as % and as a mean % competition value for serum from each of the studied groups.

Figures 21A, 21B:
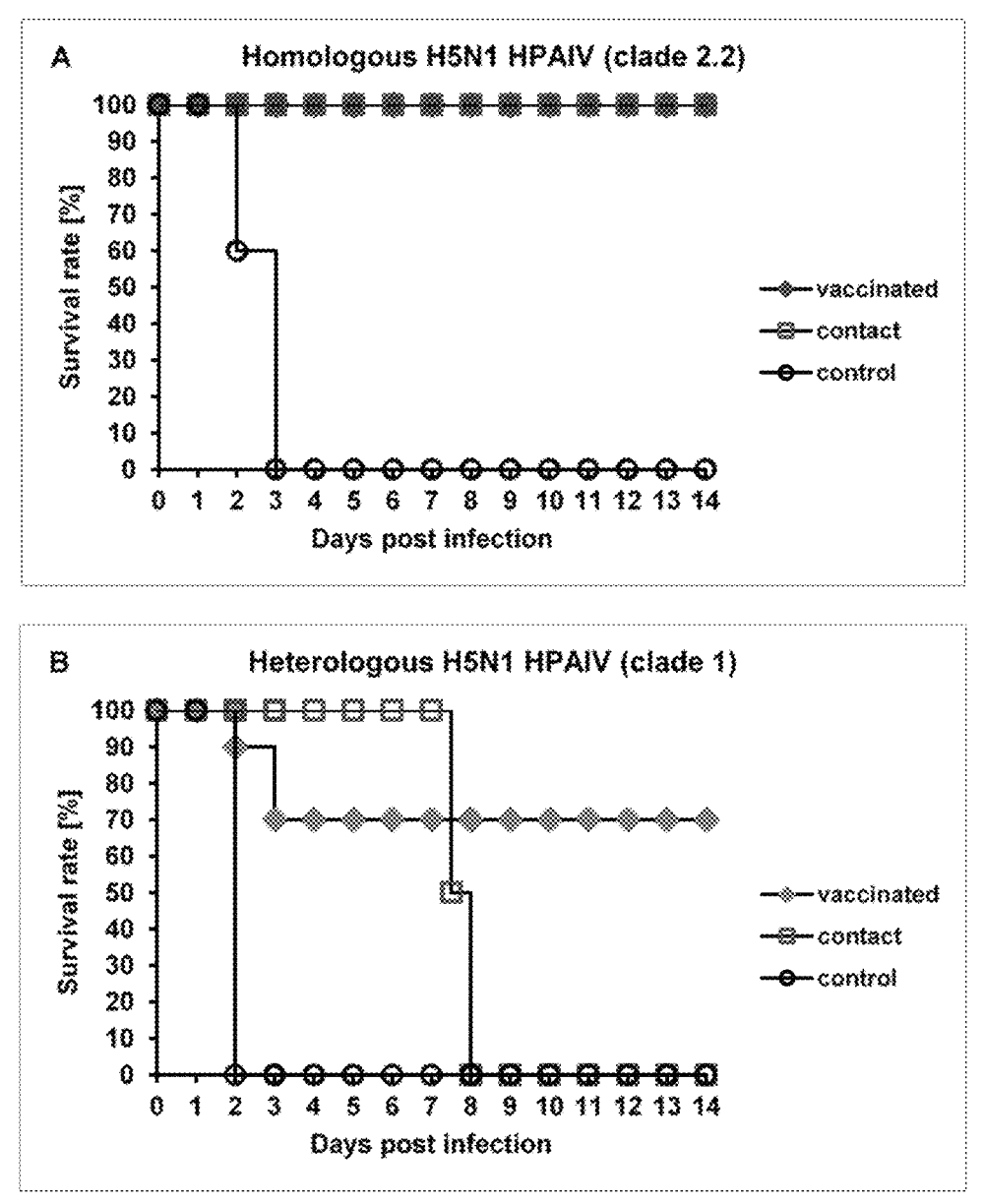

FIGS. 21A-21B shows results of an experimental infection of vaccinated and control chickens with the following HPAI H5N1 viruses: A—homologous from clade 2.2, B—heterologous from clade 1. Laying-type SPF chickens were immunized subcutaneously twice at a 4- or 4½-weeks interval with 25 µg of rH5-*E. coli* and aluminium hydroxide as an adjuvant. The infection was performed 3 weeks after the second immunization by intranasal/conjunctival (i.n./ i.o.) administration of the virus at a dose of $10^6$ $EID_{50}$. Chicken vaccinations and infection with HPAIV H5N1 were conducted according to regimens B and C. Data are presented as % survival rate for the chickens in the vaccinated (10 animals), contact (2 animals) and the control (5 animals) groups.

Figure 22:
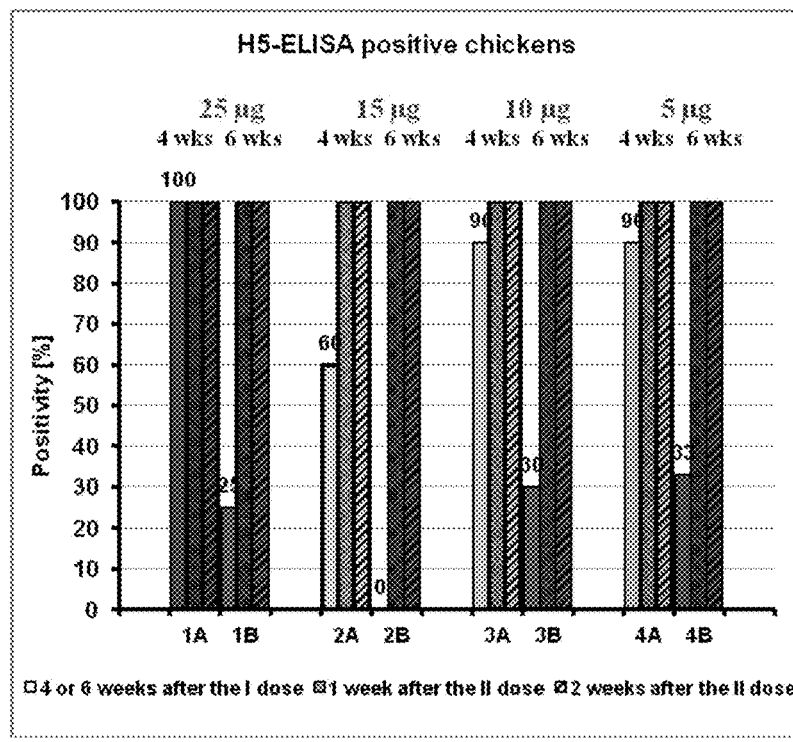
Figure 34:
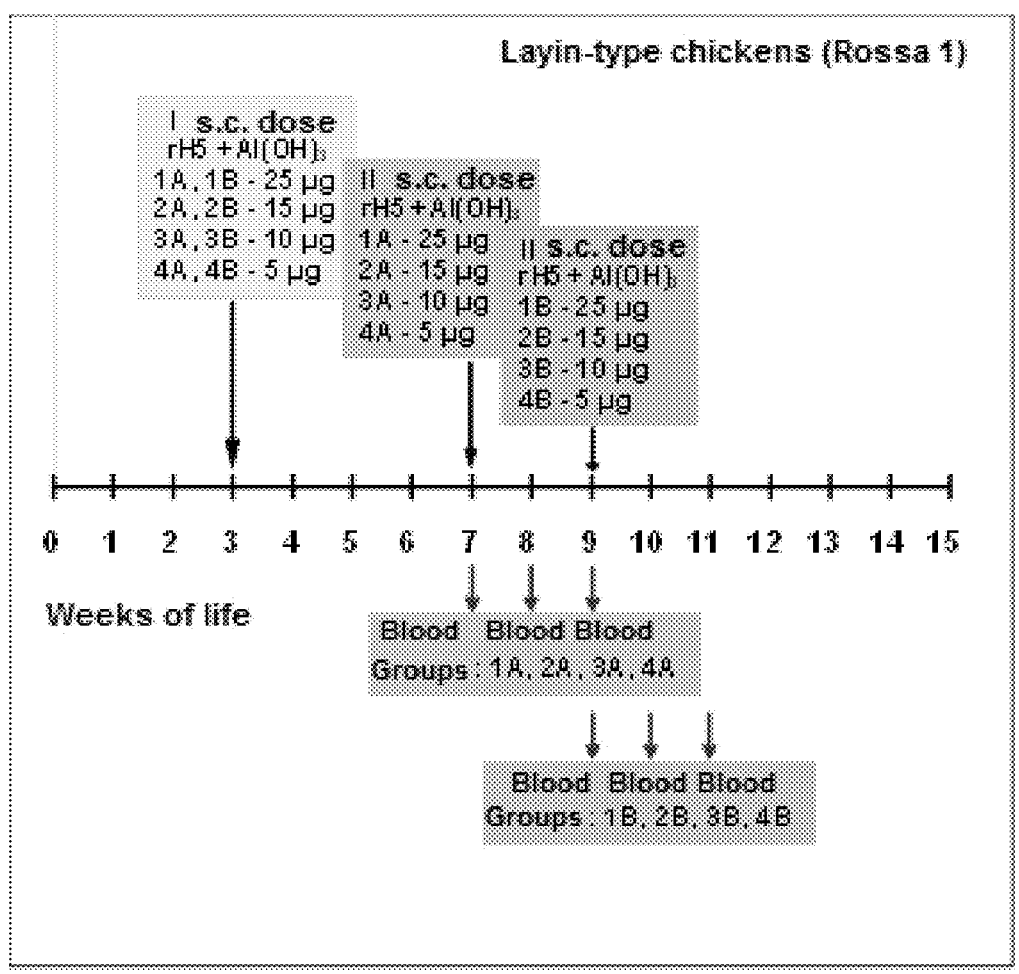

FIG. 22 shows results of indirect ELISA-H5 ELISA for detection of IgY antibodies against H5 in chicken sera obtained from animals vaccinated with rH5-*E. coli* subcutaneously twice at a 4-week interval (groups: 1A, 2A, 3A, 4A) or a 6-week interval (groups: 1B, 2B, 3B, 4B) with 25 µg (groups: 1A, 1B), 15 µg (groups: 2A, 2B), 10 µg (groups: 3A, 3B) or 5 µg (groups: 4A, 4B) of antigen per dose and aluminium hydroxide as an adjuvant. Results are shown as seropositivity level in each group at a specific stage of the experiment, determined in 1:200 diluted sera and expressed in %. Studies were conducted in laying-type chickens. Vaccinations and sample collection from experimental (groups: 1A-4A, 1B-4B) and control animals (group K) were conducted according to regimen D (FIG. 34).

Figure 23:
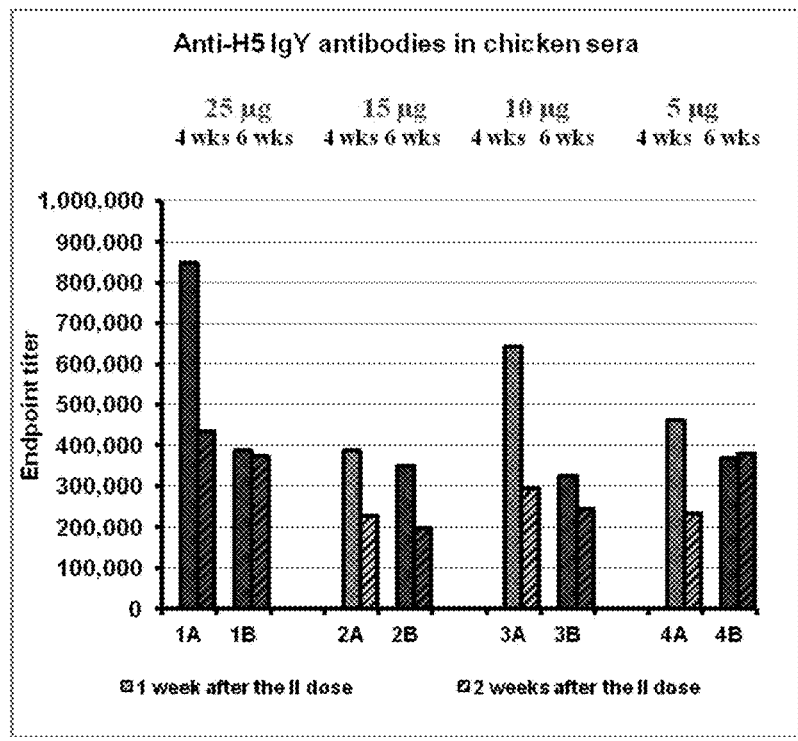

FIG. 23 shows results of the endpoint determination for IgY antibodies against H5 in sera of chickens vaccinated with rH5-*E. coli* subcutaneously twice at a 4-week (groups: 1A, 2A, 3A, 4A) or a 6-week interval (groups: 1B, 2B, 3B, 4B) using 25 µg (groups: 1A, 1B), 15 µg (groups: 2A, 2B), 10 µg (groups: 3A, 3B) or 5 µg (groups: 4A, 4B) of antigen per dose and aluminium hydroxide as an adjuvant. Sera obtained from blood collected 1 and 2 weeks after booster dose administration and sera prepared in parallel from the control group (K) were combined and titrated using the indirect ELISA (H5-ELISA). Studies were conducted in laying-type chickens. Vaccinations and sample collection from experimental (groups: 1A-4A, 1B-4B) and control (group K) animals were conducted according to regimen D (FIG. 34).

Figure 24:
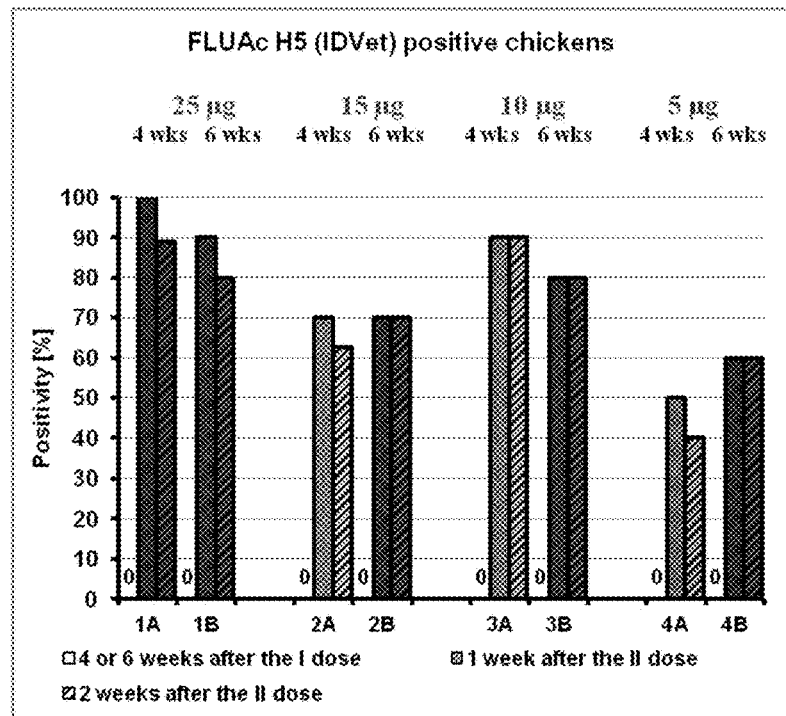

FIG. 24 shows results of the competitive ELISA-FLUAc H5 (IDVet) assay for detection of antibodies against H5 in bird sera from chickens vaccinated with rH5-*E. coli* subcutaneously twice at a 4-week (groups: 1A, 2A, 3A, 4A) or a 6-week interval (groups: 1B, 2B, 3B, 4B) with 25 µg (groups: 1A, 1B), 15 µg (groups: 2A, 2B), 10 µg (groups: 3A, 3B) or 5 µg (groups: 4A, 4B) of antigen per dose and aluminium hydroxide as an adjuvant. Results are presented as the share of seropositive chickens in each of the studied groups at a specific stage of the experiment, expressed in %. The studies were conducted in laying-type chickens. Vaccinations and sample collection from experimental (groups: 1A-4A, 1B-4B) and control (group K) animals were conducted according to regimen D (FIG. 34).

Figure 25:
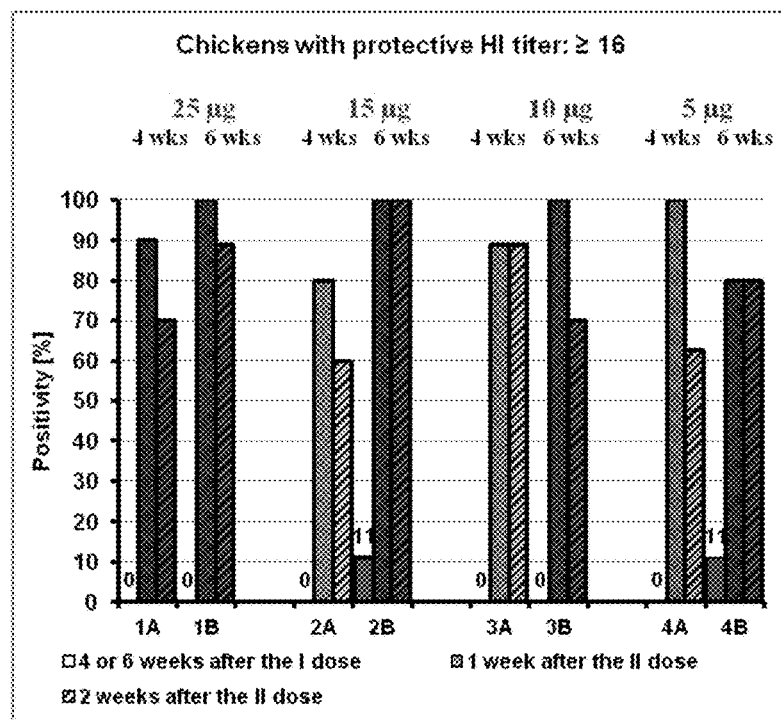

FIG. 25 shows results of the HI test, obtained for chickens vaccinated with rH5-*E. coli* subcutaneously twice at a 4-week (groups: 1A, 2A, 3A, 4A) or a 6-week interval (groups: 1B, 2B, 3B, 4B) with 25 µg (groups: 1A, 1B), 15 µg (groups: 2A, 2B), 10 µg (groups: 3A, 3B) or 5 µg (groups: 4A, 4B) of antigen per dose and aluminium hydroxide as an adjuvant. The test was conducted at HIU 1:8 with LPAIV H5N2 as a heterologous antigen, described in line-up A. The results are given as the share of seropositive chickens in each of the studied groups at a specific stage of the experiment, expressed in %. The studies were conducted in laying-type chickens. Vaccinations and sample collection from experimental (groups: 1A-4A, 1B-4B) and control (group K) animals were conducted according to regimen D (FIG. 34).

Figure 26:
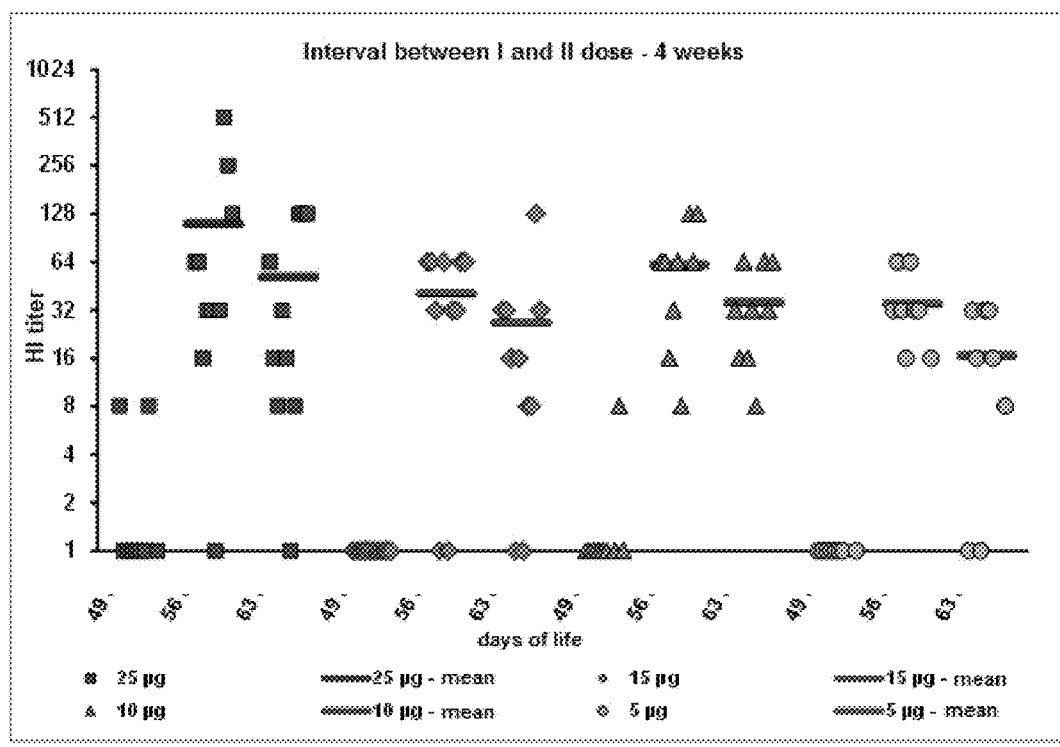

FIG. 26 shows results of the HI test, obtained for chickens vaccinated with rH5-*E. coli* subcutaneously twice at a 4-week interval (groups: 1A, 2A, 3A, 4A) with 25 µg (group 1A), 15 µg (group 2A), 10 µg (group 3A), or 5 µg (group 4A), of antigen per dose and aluminium hydroxide as an adjuvant. The test was conducted at HIU 1:8 with LPAIV H5N2 as a heterologous antigen, described in line-up A. Results of serum analyses, prepared 4 weeks after administration of priming dose and 1 and 2 weeks after the booster antigen dose, at days 49, 56 and 63 of chicken life are presented as HI antibody titer in serum of individual animals and as a mean HI antibody titer in each of the studied groups. The titer value <1:8 is marked as the 1.0 value on the chart. The studies were conducted in laying-type chickens. Vaccinations and sample collection from experimental (groups: 1A-4A) and control (group K) animals were conducted according to regimen D (FIG. 34).

Figure 27:
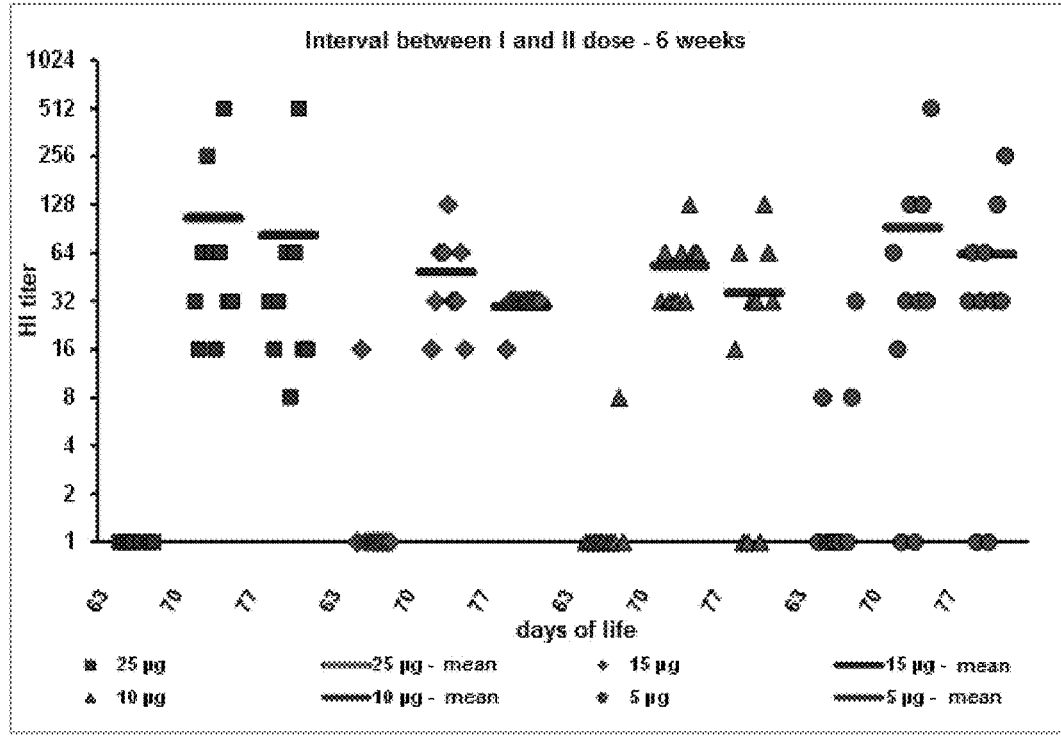

FIG. 27 shows results of the HI test, obtained for chickens vaccinated with rH5-*E. coli* subcutaneously twice at a 6-week interval (groups: 1B, 2B, 3B, 4B) using 25 µg (group 1B), 15 µg (group 2B), 10 µg (group 3B), or 5 µg (group 4B), of antigen per dose and aluminium hydroxide as an adjuvant. The test was conducted at HIU 1:8 with LPAIV H5N2 as a heterologous antigen, described in line-up A. Results of analyses of sera prepared 6 weeks after administration of priming and 1 and 2 weeks after the booster antigen dose, at days 63, 70 and 77 of chicken life are demonstrated as HI antibody titer in sera of individual animals and as a mean HI antibody titer in each studied groups. The titer value <1:8 is marked as the 1.0 value on the chart. The studies were conducted in laying-type chickens. Vaccinations and sample collection from experimental (groups: 1B-4B) and control (group K) animals were conducted according to regimen D (FIG. 34).

Figure 28:
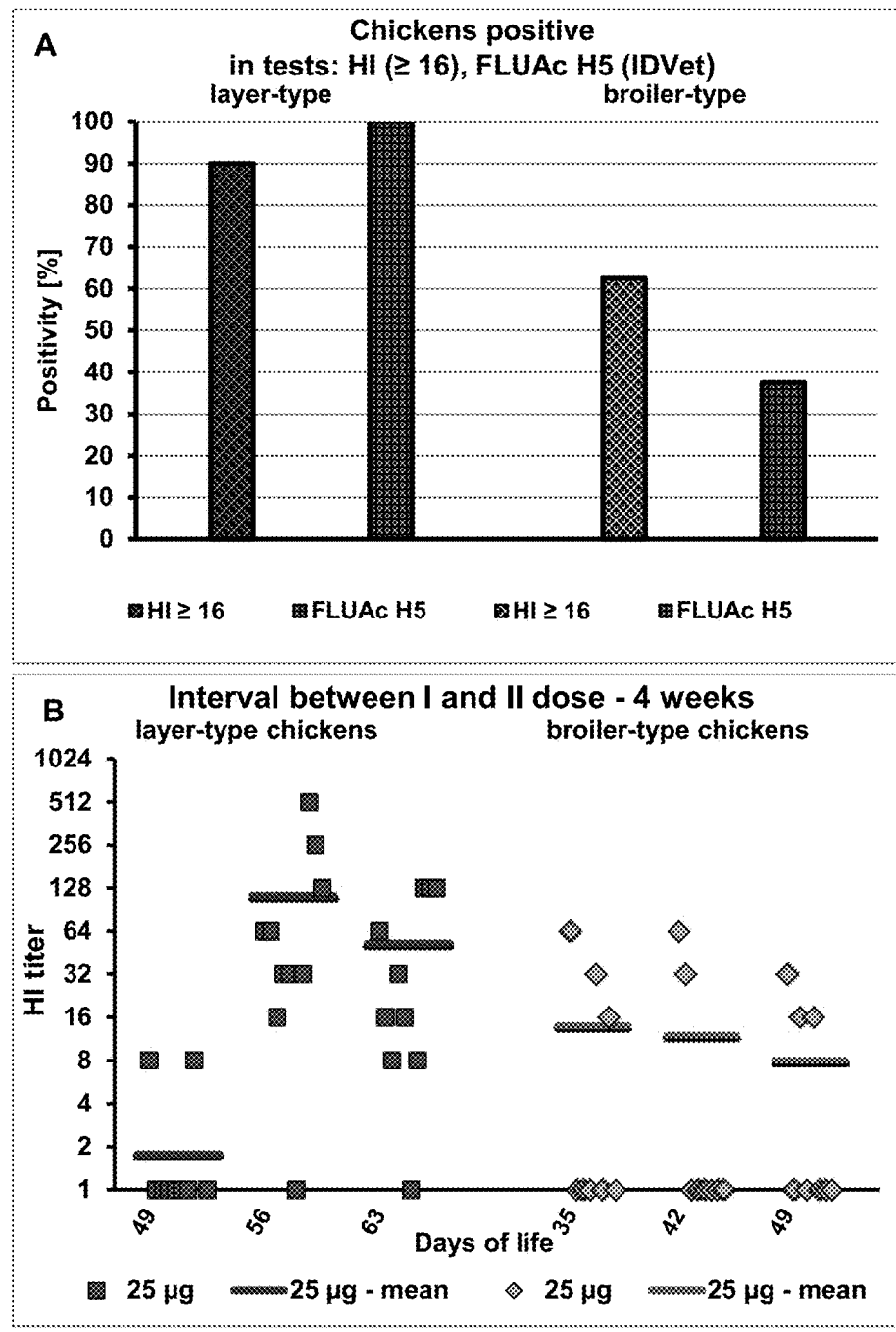

FIG. 28 shows results of assays analyzing functional antibodies against H5 HA: the HI test and the competitive ELISA-FLUAc H5 (IDVet), obtained for laying-type and broiler-type chickens vaccinated with rH5-*E. coli* subcutaneously twice at a 4-week interval with 25 µg of antigen and aluminium hydroxide as an adjuvant. The HI test was conducted at HIU: 1:8 with LPAIV H5N2 as a heterologous antigen, described in line-up A. A—results of analyses of sera with HI-H5N2 and FLUAc H5 tests are shown as the share of chickens with protective HI titer (≥1:16) and chickens seropositive in the FLUAc H5 assay in each studied group, expressed in %. B—results of serum analyses with the HI-H5N2 test are shown as the HI antibody titer in sera of individual animals determined in samples collected 4 weeks after administering priming and 1 and 2 weeks after booster antigen dose, at days 49, 56 and 63 of laying-type chicken life and at days 35, 42 and 49 of broiler-type chicken life and as a mean HI antibody titer in each studied group. The titer value <1:8 is marked as the 1.0 value on the chart. Vaccinations and sample collection from laying-type chickens were conducted according to group 1A schedule, shown in regimen D (FIG. 34), and from broiler-type chickens according to group C schedule, shown in regimen A (FIG. 31).

Figure 29:
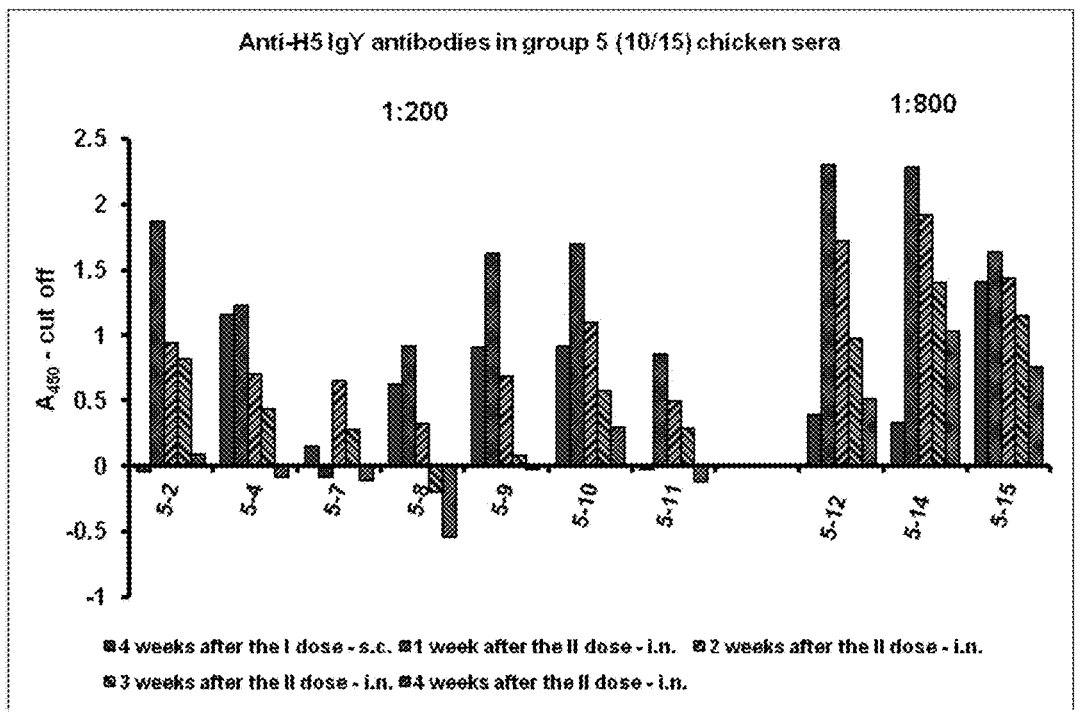
Figure 35:
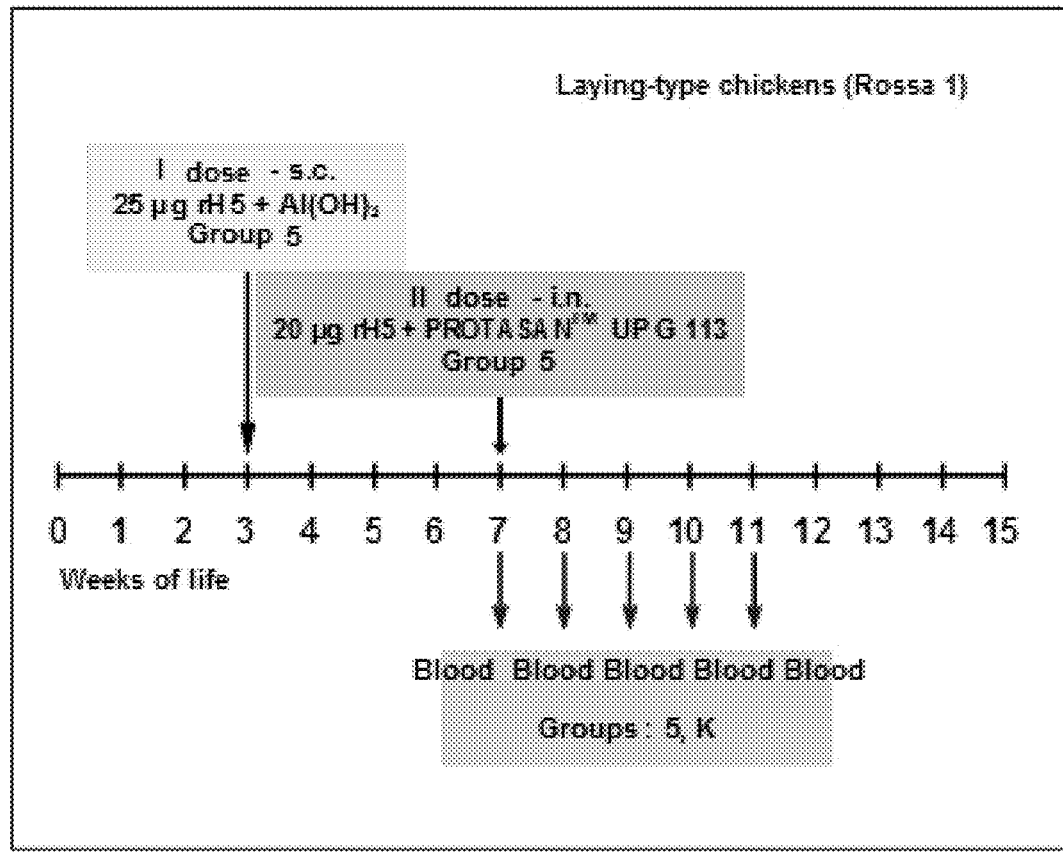

FIG. 29 shows results of the indirect ELISA detecting IgY antibodies against H5 in chicken serum (H5-ELISA), obtained for individual animals vaccinated twice with rH5-*E. coli* at a 4-week interval by administering a priming dose (25 μg with aluminium hydroxide) subcutaneously and a booster dose (20 μg with PROTASAN™ UP G 113) intranasally. Results are shown as signal values ($A_{450}$) exceeding cut off values ($A_{450}$—cut off) obtained for 10 of 15 vaccinated chickens that responded to intranasal immunization. Studies were conducted in laying-type chickens. Vaccinations and sample collection from experimental (group no. 5) and control (group K) animals were performed according to regimen E (FIG. 35).

Figure 30:
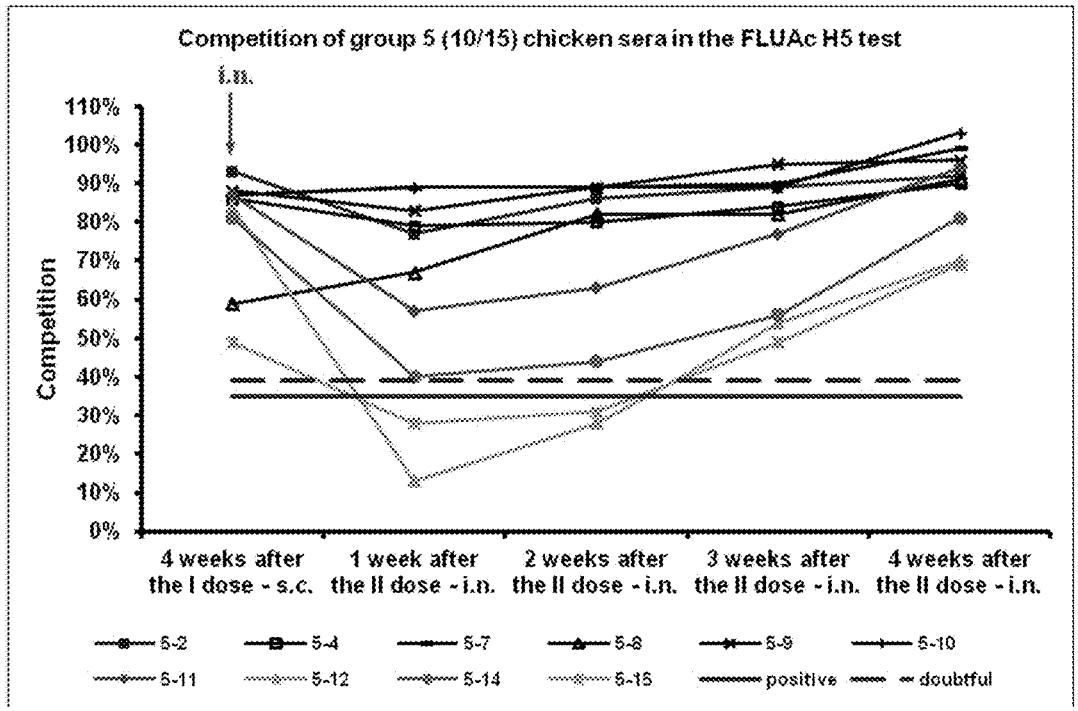

FIG. 30 shows results of the competitive ELISA-FLUAc H5 (IDVet) assay for detection of antibodies against H5 in bird sera, obtained for individual animals vaccinated twice with rH5-*E. coli* at a 4-week interval by administering a priming dose (25 μg with aluminium hydroxide) subcutaneously and a booster dose (20 μg with PROTASAN' UP G 113) intranasally. Data from the analysis of sera are shown for chickens that based on the indirect H5-ELISA results responded to intranasal immunization (10/15). Studies were conducted in laying-type chickens. Vaccinations and sample collection from experimental (group no. 5) and control (group K) animals were performed according to regimen E (FIG. 35).

FIG. 31 shows Regimen A for chicken immunization with rH5-*E. coli* and sample collection for serological analyses.

Figure 32:
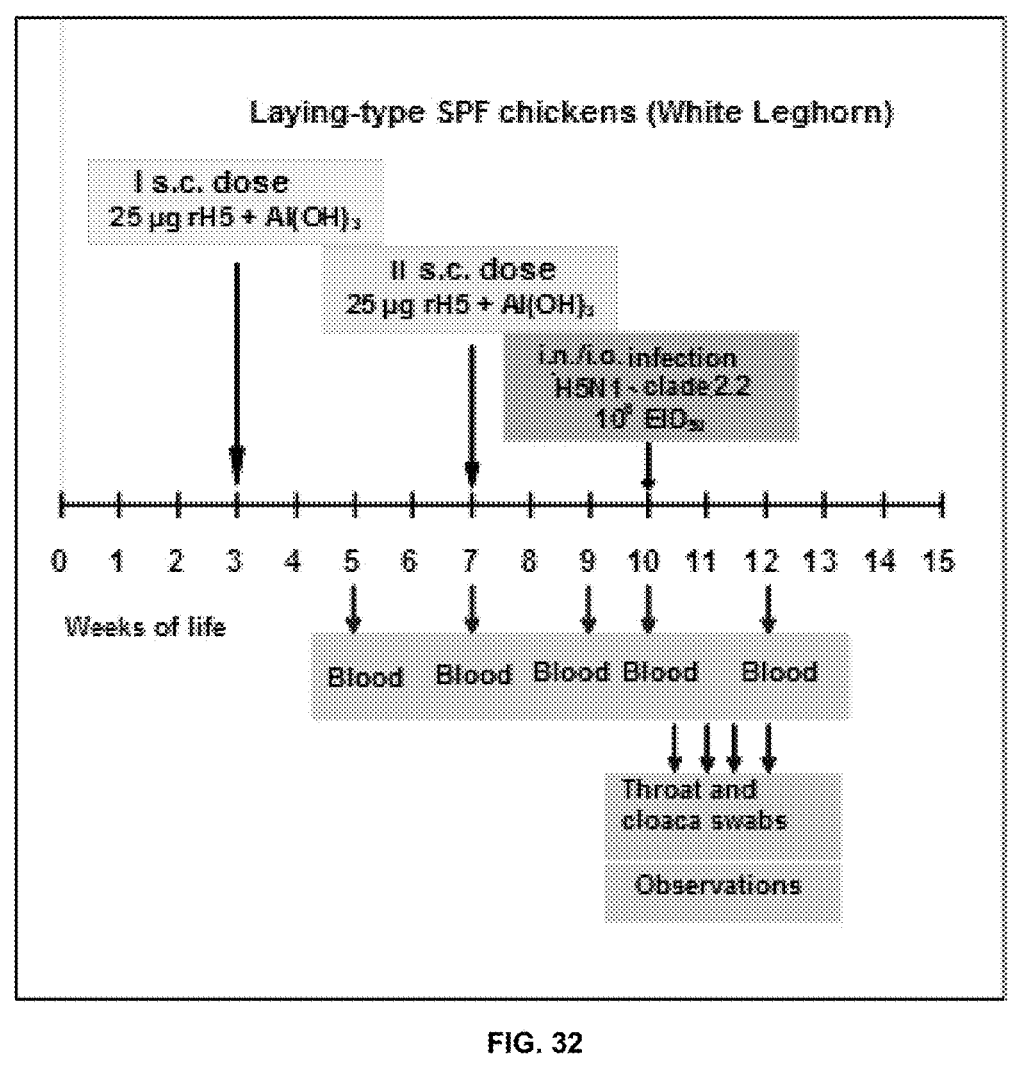

FIG. 32 shows Regimen B of chicken immunization with rH5-*E. coli*, experimental infection with homologous HPAIV H5N1 and sample collection for analyses.

Figure 33:
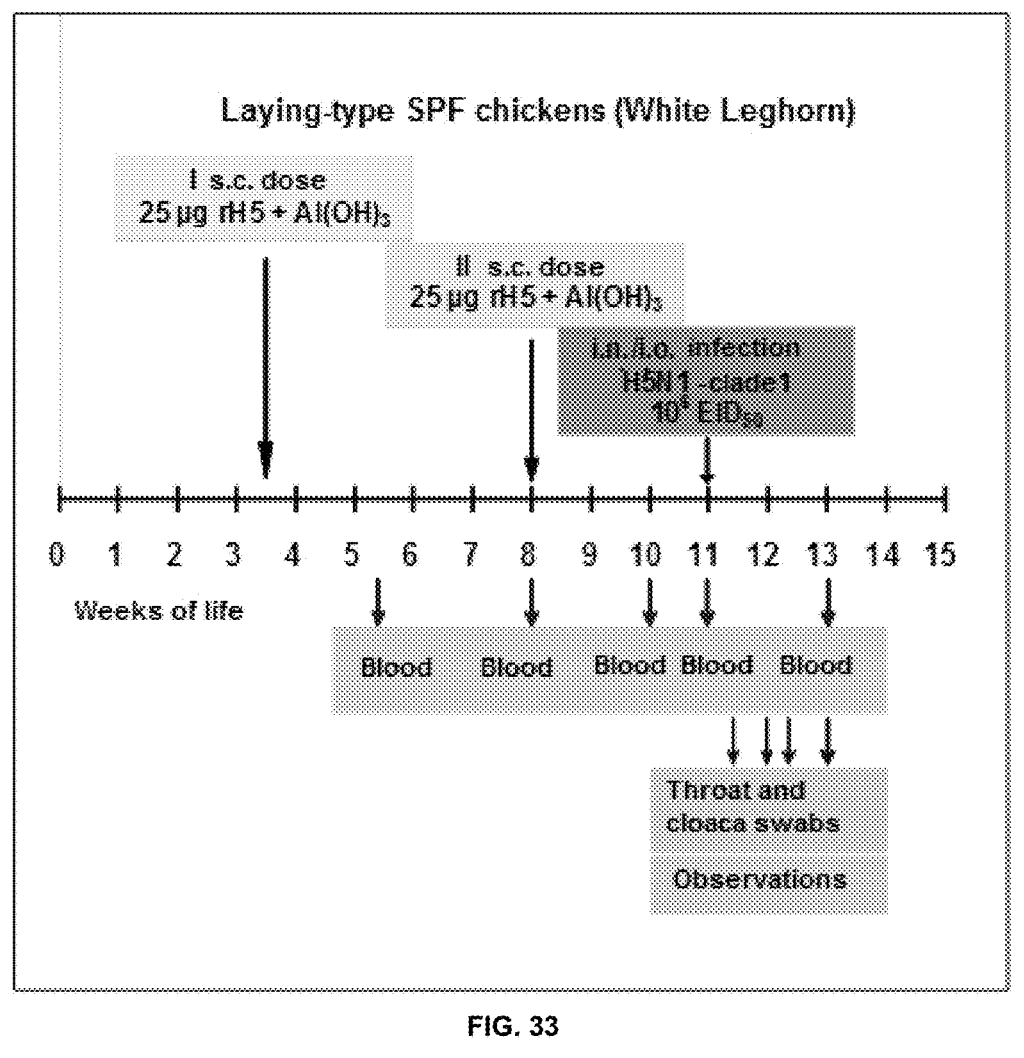

FIG. 33 shows Regimen C of chicken immunization with rH5-*E. coli*, experimental infection with heterologous HPAIV H5N1 and sample collection for analyses.

FIG. 34 shows Regimen D for chicken immunization with rH5-*E. coli* and sample collection for serological studies.

FIG. 35 shows Regimen E for chicken immunization with rH5-*E. coli* and collection of samples for serological studies.

Tab. 1 shows a quantitative analysis of the composition of one of the rH5-*E. coli* preparations. Results for hemagglutinin monomer and dimer are marked in bold.

Tab. 2 shows results of immunoreactivity assays of monoclonal (Mab) and polyclonal (Pab) antibodies against HA with rH5 of different H5 serotype AIV strains. HA proteins were obtained in the baculovirus (Oxford Expression Technologies) or mammalian (Immune Technology Corp.) expression systems. Hemagglutinin homology was determined for full-length protein (1-568 aa) and the HA-1 subunit (17-340 aa) in relation to HA from the A/swan/Poland/305-135V08/2006(H5N1) strain. Commercially available Mabs (Acris Antibodies, ABR/Thermo Scientific, USBiological) and Pabs (Immune Technology Corp.) were used in the assay. Analyses were conducted by ELISA on Ni-NTA plates (Qiagen).

Tab. 3 shows results of the hemagglutination assay (HA) conducted with chicken erythrocytes for an example rH5-*E. coli* preparation. The reduced rH5-*E.coli* protein was the negative control for the HA assay for hemagglutinin from a bacterial expression system. The HA protein (17-530 aa, ΔRRRKKR, 6xHis), produced on the basis of the HA sequence from the A/swan/Poland/305-135V08/2006 (H5N1) strain in the baculovius expression system (Oxford Expression Technologies)—rH5-BEVS (OET) and the A/Bar-headed Goose/Qinghai/12/05 (H5N1) strain in a mammalian expression system (Immune Technology Corp.)—mammalian rH5 (ITC), were reference antigens.

Tab. 4.1 shows results of the competitive ELISA-FLUAc H5 (IDVet) assay for detection of antibodies against H5 in bird sera, collected from chickens vaccinated subcutaneously with one 25 μg-dose of rH5-*E. coli* and aluminium hydroxide as an adjuvant. Serum samples that contained the highest levels of IgT antibodies against H5 in individual chickens, as shown in the H5-ELISA, were used for analysis and were prepared from blood collected 2(*), 4() or 5(*) weeks after immunization. Studies were conducted in broiler-type chickens. Vaccinations and sample collection from the animals were performed according to group A schedule, shown in regimen A (FIG. 31).

Tab. 4.2 shows results of the competitive ELISA-FLUAc H5 (IDVet) assay for detection of antibodies against H5 in bird sera, collected from chickens vaccinated twince subcutaneously at a 2-week interval with 25 μg of rH5-*E. coli* and aluminum hydroxide as an adjuvant. Studies were conducted in broiler-type chickens. Vaccinations and sample collection from animals were performed according to group B schedule, shown in regimen A (FIG. 31).

Tab. 4.3 shows results of the competitive ELISA-FLUAc H5 (IDVet) assay for detection of antibodies against H5 in bird sera, collected from chickens vaccinated twice subcutaneously at a 4-week interval with 25 μg of rH5-*E. coli* and aluminum hydroxide as an adjuvant. Studies were conducted in broiler-type chickens. Vaccinations and sample collection from animals were performed according to group C schedule, shown in regimen A (FIG. 31).

Tab. 5.1 shows results of HI tests obtained for chickens vaccinated subcutaneously with one 25 μg-dose of rH5-*E. coli* and aluminum hydroxide as an adjuvant. Tests were conducted at HIU=1:8 with homologous HPAIV H5N1 and heterologous LPAIV H5N2 as antigens, described in line-up A. Studies were conducted in broiler-type chickens. Vaccinations and sample collection from animals were performed according to group A schedule, shown in regimen A (FIG. 31).

Tab. 5.2 shows results of HI tests obtained for chickens vaccinated twice subcutaneously at a 2-week interval with 25 μg of rH5-*E. coli* and aluminium hydroxide as an adjuvant. Tests were conducted at HIU=1:8, using homologous HPAIV H5N1 and heterologous LPAIV H5N2 as antigens, described in line-up A. Studies were conducted in broiler-type chickens. Vaccinations and sample collection from animals were performed according to group B schedule, shown in regimen A (FIG. 31).

Tab. 5.3 shows results of HI tests obtained for chickens vaccinated twice subcutaneously at a 4-week interval with 25 μg of rH5-*E. coli* and aluminium hydroxide as an adjuvant. Tests were conducted at HIU=1:8 with homologous HPAIV H5N1 and heterologous LPAIV H5N2 as antigens, described in line-up A. Studies were conducted in broiler-type chickens. Vaccinations and sample collection from animals were performed according to group C schedule, showin in regimen A (FIG. 31).

Tab. 6 shows results of immunization studies in broiler-type chickens, obtained using an indirect and competitive ELISAs for detection of antibodies against H5 in chickens sera (H5-ELISA; FLUAc H5, IDEVet) and HI tests with AI viruses described in line-up A: homologous HPAIV H5N1 and heterologous LPAIV H5N2. Animals were administered subcutaneously one (group A) or two 25 μg-doses (groups: B, C) of rH5-*E. coli* with aluminum hydroxide as an adjuvant. Booster vaccination in group B was administered 2 weeks after and in group C—4 weeks after the priming vaccination. Vaccinations and sample collection from animals were performed accoridng to schedules for groups A, B and C, shown in regimen A (FIG. 31). The table includes results of analyses of available serum samples from all blood collections in groups A, B, and C (), or from blood collected from group A animals, which contained the highest levels IgY antibodies against H5 in individual chickens and were prepared 2, 4 or 5 weeks after immunization (*).

Tab. 7 shows results of the IDEXX AI MultiS-Screen (Idexx Laboratories) assay for detection of antibodies against AI viruses in bird sera from laying-type SPF chickens in a challenge experiment. Animals were immunized subcutaneously twice at a 4- or 4 1/2-weeks interval using 25 µg of rH5-*E. coli* and aluminium hydroxide as an adjuvant. The infection was performed by intranasal/conjunctival (i.n./i.o.) administration of the virus at a dose of $10^6$ $EID_{50}$. Chicken vaccinations and infection were conducted according to regimens B and C. Serum samples collected 3 weeks after administering the booster dose of the antigen, i.e. directly before infection and 2 weeks after infection with clade 2.2 homologous (experiment 1) or clade 1 heterologous (experiment 2) HPAIV H5N1, were analyzed. Chickens that died 3, 2, 8, 7-8 dpi are indicated as a, b, c, d, respectively. Chickens exhibiting less or more severe disease symptons are indicated*, ** respectively.

Tab. 8 shows results of real time RT-qPCR analyses of throat (T) and cloacal (C) swabs collected from laying-type SPF chickens vaccinated with rH5-*E. coli* and infected with HPAIV H5N1 and from contact chickens. Chickens were immunized subcutaneously twice at a 4- or 4 1/2-weeks interval with 25 µg of rH5-*E. coli* and aluminum hydroxide an an adjuvant. The infection was performed 3 weeks after the second immunization by intransally/conjunctivally (i.n./i.o.) admininstering the clade 2.2 homologous or clade 1 heterologous HPAIV H5N1 viruses at a dose of $10^6$ $EID_{50}$. Chicken vaccinations and infection were conducted according to regimens B and C. Swabs were collected from animals that survived the infection 3, 7, 10 and 14 days post infection (dpi). Swabs from chickens that died at 3,2,8,7-8 dpi, indicated as a, b, c, d, respectively, were collected *post mortem* (*pm*). Chickens exhibiting less or more severe disease symptoms are indicated *, ** respectively. The amount of viral RNA is expressed in PCR units $EID_{50}/ml$ and shown as $log_{10}EID_{50}/ml$.

Tab. 9 shows results of the competitive ELISA-FLUAc H5 (IDVet) test for detection of antibodies against H5 in bird sera and the H1 test at HIU=1:8 with heterologous LPAIV H5N2, described in line-up A, obtained in chicken immunization trials. Animals were vaccinated with rH5-*E. coli* subcutaneously twice at a 4-week (groups: 1A, 2A, 3A, 4A) or a 6-week interval (groups: 1B, 2B, 3B, 4B) with 25 µg (groups: 1A, 1B), 15 µg (groups: 2A, 2B), 10 µg (groups: 3A, 3B) or 5 µg (groups 4A, 4B) of antigen per dose and aluminum hydroxide as an adjuvant. Results are shown as mean percentage of chickens seropositive in the FLUAc H5 assay and exhibiting a protective HI antibody titer (≥1:16) 1 and 2 weeks after the second administration of 25, 15, 10 or 5 µg of rH5-*E. coli* (n=4) and all administered antigen doses (n=16). The studies were conducted in laving-type chickens. Vaccinations and sample collection from experimental (groups: 1A-4A, 1B-4B) and control (group K) animals were conducted according to regimen D (FIG. 34).

Tab. 10 shows results of the HI test, obtained from chickens vaccinated twice with rH5-*E. coli* at a 4-week interval by administering a priming dose (25 µg with aluminum hydroxide) subcutaneously and a booster dose (20 µg with PROTASAN™ UP G 113) intranasally. Analyses were conducted at HIU=1:8 with LPAIV H5N2 as a heterologous antigen, described in line-up A. Data from the analysis of sera are shown for chickens that, according to the indirect H5-ELISA responded to intranasal immunization (10/15). Studies were conducted in laving-type chickens. Vaccinations and sample collection from experimental (group No. 5) and control (group K) animals were performed according to regimen E (FIG. 35).

The invention is presented in the following embodiments.

EXAMPLE 1 PRODUCTION OF THE HEMAGGLUTININ FRAGMENT (17-522 AA, ΔRRRKKR (SEQ ID NO: 2)) FROM HIGHLY PATHOGENIC AVIAN INFLUENZA VIRUS (HPAIV) H5N1 IN *ESCHERICHIA COLI* BL21(DE3) CELLS

A fragment of the HA 17-522 aa coding sequence was obtained with a deletion of the HA0 cleavage site between the HA-1 and HA-2 subunits (ΔRRRKKR). The sequence encodes the HA-1 subunit and a fragment of the HA-2 subunit and is deprived of the RRRKKR (SEQ ID NO: 7) basic amino acids in the 341-346 aa region of the HA antigen.

The cDNA fragment containing the full-length reading frame for hemagglutinin was prepared by reverse transcription and subsequent amplification (RT-PCR) on the RNA template from the Polish influenza virus strain from 2006 (A/swan/Poland/305-135V08/2006; EpiFlu Database; access number EPI156789; gisaid.org) (Gromadzka et al., 2008) Based on the obtained nucleotide sequence (FIG. 1) the hemagglutinin protein amino acid sequence was established. A construct was prepared comprising a cloned hemagglutinin coding sequence fragment. It became the starting point for the preparation of a modified hemagglutinin coding sequence. The modified sequence comprises the 17-522 amino acids with a deletion of the 341-346 amino acids (RRRKKR (SEQ ID NO: 7), in the cleavage site between the HA-1 and HA-2 subunits).

*E. coli* Strains Used During the Procedure:
NM522 supE thi Δ (lac-proAB) hsd5 F'[proAB+lacI$^q$ lacZΔM15]
BL21(DE3) hsdS gal (λcIts857 ind1 Sam7 nin5 lacUV5-T7 gene 1)

Vectors Used for Cloning:
A Non-Expression Bacterial Plasmid

To clone the DNA fragments after PCR amplification a non-expression plasmid (sequence available in GenBank, accession no. X52324 S52394) was used. The plasmid contains: the ColE1 replication origin, T3 and T7 promoters (for phage RNA polymerases) flanking a polylinker and the ampicillin resistance gene.

Bacterial Expression System:

A bacterial expression system, developed at the Institute of Biotechnology and Antibiotics in Warsaw was used to produce the recombinant protein. The system is the object of patent applications nos. P379905 (2007), PCT/PL2007/000037 and the American patent no. U.S. Pat. No. 8,628,954 B2. In this system proteins are produced in host cells, such as *Escherichia coli*, comprising the T7 phage RNA polymerase coding gene. A vector comprising the target gene operationally linked with a promoter recognized by the T7 phage RNA polymerase is introduced into the host cells and the host cells are cultured under controlled conditions promoting expression. The employed system enables protein expression that is stable over time thanks to the application of an expression cassette comprising a phage promoter operationally linked with the target polypeptide coding sequence and with the sequence encoding the selective marker that determines the survival of the host expressing the target polypeptide. The transcription terminator for promoters other than phage promoters is found in the cassette, between the target polypeptide coding sequence and the sequence coding for the selective marker determining host survival.

Figure 2:
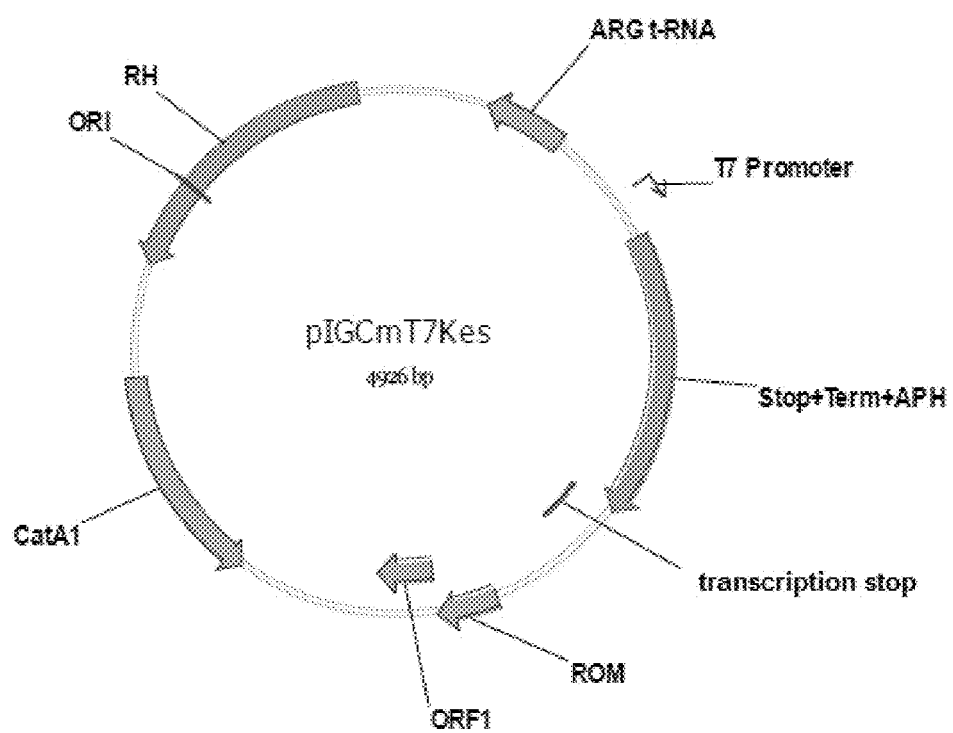

The application of the modified expression vector makes it possible to eliminate from the culture those bacterial cells, in which chromosome a mutation appeared preventing production of functional T7 phage polymerase and/or those in which, as a result of a mutation, the T7 phage promoter has lost its functionality. The expression stabilizing cassette is inserted into the vector pIGCmT7Kes (FIG. 2). The pIGCmT7Kes plasmid comprises the chloramphenicol acetyltransferase (CatA1) gene, introducing chloramphenicol resistance, a polylinker with the promoter recognized by T7 phage RNA polymerase and a transcription stop codon coding sequence derived from phage T7. The pIGCmT7Kes plasmid carries the tRNA gene coding for the AGA and AGG codons. The AGA and AGG tRNA codons supplement a deficiency of these tRNAs resulting from the frequency of codon usage in E. coli.

Production of Vector pIGKesHA17522Δ with Inserted HPAIV H5N1 Hemagglutinin Fragment (17-522 Aa, ΔRRRKKR (SEQ ID NO: 2))

Scheme for Production of Vector pIGKesHA17522

Step I.

Construction of pGEM-T Easy plasmid comprising the hemagglutinin (A/swan/Poland/305-135V08/2006 (H5N1)) coding gene sequence.

The first step was to acquire genetic material from avian influenza virus using an efficient method of viral genetic material purification. The starting material for those reactions were samples provided by veterinarians and ornithologists. The cDNA fragment was obtained by reverse transcription with subsequent amplification (RT-PCR) on the RNA template from the Polish influenza virus strain from 2006 (A/swan/Poland/305-135V08/2006). The fragment contained the full-length reading frame for hemagglutinin. The obtained fragment was cloned into the pGEM-T Easy plasmid (Promega) used in DNA sequence analysis.

Step II.

From the pGEM-T Easy plasmid comprising the hemagglutinin (A/swan/Poland/305-135V08/2006 (H5N1)) coding gene sequence, the hemagglutinin coding gene was amplified by PCR using the following primers: Ha17522 (forward primer 5'-GAGGGGATCCATATGGATCAGATTTGCATTGGTTACC-3') and HaFr522 (reverse primer 5'-GGCCCTCGAGTTATACTCCACTTATTTCCTCGCG-3'). The PCR primers were designed on the basis of the DNA sequence encoding hemagglutinin. The primer sequence complementary to the amplified gene sequence is underlined.

Primer Ha17522 introduces sites recognized by the BamHI and NdeI restriction nucleases. Primer HaFr522 primer introduces sites recognized by the XhoI restriction nuclease. The product obtained in the PCR reaction was separated by electrophoresis and isolated from the polyacrylamide gel and then digested with the BamHI and XhoI restriction enzymes and deproteinated. The obtained fragment was ligated into pBluescript SK(−) digested with the same restriction enzymes. The ligation product was used to transform E. coli NM522 cells. After plasmid DNA isolation from the transformed E. coli cells, the presence of the cloned HA insert was confirmed by restriction analysis and the sequence accuracy was verified by sequencing.

Step III.

Codons of the HA insert sequence were optimized allowing for improved expression efficiency in E. coli. For this purpose selected codons in the virus-derived sequence were replaced so that it contained those most often found in E. coli. The replacement was performed in a site-directed mutagenesis reaction. The replaced codons are marked in bold in the sequence (FIG. 3)

Step IV.

The cloned DNA fragment was digested out of the pBluescript vector with digestion enzymes NdeI and XhoI and deproteinated. The obtained DNA fragment was ligated with the vector pIGCmT7Kes, digested with the same restriction enzymes and deproteinated after digestion. The ligation product was used to transform E. coli NM522 cells. The presence of the cloned HA 17-522 aa insert in the obtained vector pIGKesHA17522 was confirmed by restriction analysis.

Scheme for Construction of Vector pIGKesHA17522Δ

The vector pIGKesHA17522 was used as the template in the amplification reaction. PCR was run using primers designed on the basis of the hemagglutinin coding sequence. The product was the HA 17-522 aa coding sequence without the fragment coding amino acids 341-346, i.e. RRRKKR SEQ ID NO: 7. The deleted amino acid 341-346 region is the HA0 cleavage site between the HA-1 and HA-2 subunits. The deleted amino acids are underlined in the nucleotide sequence (FIG. 3). The obtained HA fragment with the RRRKKR SEQ ID NO: 7 deletion (HAΔ) was the PCR template, in which primer Ha17522 introduces sites recognized by the BamHI and NdeI restriction nucleases. Primer HaFr522 introduces sites recognized by the XhoI restriction nuclease.

The PCR product was separated by electrophoresis and isolated from agarose gel, digested with the NdeI and XhoI restriction enzymes and deproteinated. The obtained fragment was ligated into the vector pIGCmT7Kes digested with the same restriction enzymes. The ligation product was used to transform E. coli NM522 cells. After plasmid DNA was isolated from the transformed E. coli cells, the presence of the cloned HA17522Δ insert in the vector pIGKesHA17522Δ (FIG. 4) was confirmed by restriction analysis and the sequence accuracy was verified by sequencing.

Construction of E. coli BL21(DE3) Strain Expressing the HPAIV H5N1 Hemagglutinin Fragment (17-522 Aa, ΔRRRKKR (SEQ ID NO: 2))

E. coli BL21(DE3) cells were transformed with the pIGKesHA17522Δ plasmid comprising the verified HA17522Δ coding sequence. Escherichia coli cells were transformed using the method for competent E. coli cell transformation proposed by Chung and Miller [Chung C T, Miller R H. A rapid and convenient method for preparation and storage of competent bacterial cells. Nucleic Acids Res. 1988 Apr. 25; 16(8):3580]. Transformants were selected on LB medium supplemented with chloramphenicol (12 μg/ml).

The product was E. coli BL21(DE3) strain expressing the HA17522Δ gene with a deletion of the HA0 cleavage region between the HA-1 and HA-2 subunits (ΔRRRKKR). The strain expresses the rH5 recombinant protein comprising the HA-1 subunit and a fragment of the HA-2 subunit, and it is deprived of the region comprising the RRRKKR SEQ ID NO: 7 amino acids in the 341-346 aa site of the HA antigen. The amino acid sequence of the rH5 protein is shown on FIG. 1.5.

Expression of the HPAIV H5N1 Hemagglutinin Fragment (17-522 Aa, ΔRRRKKR SEQ ID NO: 2) in *E. coli* BL21 (DE3).

*Escherichia coli* BL21(DE3) bacteria harboring the recombinant plasmid were cultured in LB medium with chloramphenicol (12 µg/ml) at 25° C. with shaking (150 rpm) until OD600~0.6. The rH5 expression was induced by adding isopropyl-thio-β-D-galactoside (IPTG, up to the final concentration of 0.1 µg/ml). The bacteria were cultured for 4.5 h without changing culture conditions and then centrifuged.

Isolation of Inclusion Bodies Containing rH5 from *E. coli*

The cell pellet was suspended in lysis buffer (0.5 M NaCl; 0.05 M Tris HCl pH 7.5; 0.01 M EDTA pH 7.5; 0.005 M 2-Mercaptoethanol; 0.35 mg/ml lysozyme; 1% PMSF) and incubated for 30 minutes at 20° C. Triton X-100 was added up to concentration of 1%. The suspension was sonicated and centrifuged. The inclusion bodies pellet was suspended in PBS buffer containing 1% Triton X-100 and then in PBS containing 2M urea and centrifuged. The isolated inclusion bodies were washed twice with PBS buffer. Finally, the inclusion bodies were suspended in PBS buffer, divided into batches and frozen at −20° C. for further analysis.

Analysis of Inclusion Bodies Isolated from *E. coli* BL21 (DE3)

The presence of the inclusion body fraction containing rH5 was confirmed by separating samples by electrophoresis in 15% polyacrylamide gel (SDS-PAGE). Proteins were visualized with Coomassie Brilliant Blue G. Images for electrophoretic separation of isolated inclusion body samples are shown on FIG. 6.

EXAMPLE 2 PRODUCTION OF THE HEMAGGLUTININ FRAGMENT (17-522 AA, ΔRRRKKR SEQ ID NO: 2) FROM HIGHLY PATHOGENIC AVIAN INFLUENZA VIRUS (HPAIV) H5N1 IN *ESCHERICHIA COLI* Z0526

The product was the HA 17-522 aa coding sequence fragment with the HA0 cleavage region between the HA-1 and HA-2 subunits deleted (ΔRRRKKR). This sequence encodes the HA-1 subunit and a fragment of the HA-2 subunit and is deprived of basic amino acids RRRKKR SEQ ID NO: 7 in the 341-346 aa region of the HA antigen.

The cDNA fragment comprising the hemagglutinin full-length reading frame was prepared by reverse transcription and subsequent amplification (RT-PCR) on the RNA template from the Polish influenza virus strain from 2006 (A/swan/Poland/305-135V08/2006; EpiFlu Database; access number EPI156789; gisaid.org) (Gromadzka et al., 2008) Based on the obtained nucleotide sequence (FIG. 1) the hemagglutinin protein amino acid sequence was established. A construct was produced comprising the cloned hemagglutinin coding sequence fragment. It became the starting point for the production of a modified hemagglutinin coding sequence. The modified sequence comprises the 17-522 amino acids with a deletion of the 341-346 amino acids (RRRKKR SEQ ID NO: 7, in the cleavage site between the HA-1 and HA-2 subunits).

*E. coli* Strains Used During the Procedure:
NM522 supE thi Δ (lac-proAB) hsd5 F'[proAB+ lacI$^q$ lacZΔ M15]
Z0526 F$^-$ cyt R, strA Vectors Used for Cloning:
Bacterial Expression Plasmid The pDB plasmid contains the constitutive deoP1P2 promoter. Expression of recombinant proteins produced using the pDB plasmid is regulated by the deoP1P2 promoter. The pDB plasmid also carries the tetracycline resistance gene facilitating cell selection after transformation with the plasmid.

Bacterial Expression System:

Protein production in this system is based on host cells, such as *Escherichia coli* Z0526. This strain carries the gene coding for polymerase recognizing the deoP1P2 promoter. The recognized deoP1P2 promoter is found in the pDB expression plasmid. In *Escherichia coli* Z0526, the cytR and strA gene sequence was mutated within the chromosome. The vector comprising the target gene encoding the recombinant protein is introduced to the host cells by transformation. The transformed host cells are cultured under controlled conditions promoting expression. The used system allows for constitutive recombinant protein expression.

Production of the Vector pDBHA17522Δ with the Inserted HPAIV H5N1 Hemagglutinin Fragment (17-522 Aa, ΔRRRKKR (SEQ ID NO: 2))

Scheme for Construction of the Vector pDBHA17522Δ

In the amplification reaction the vector pIGKesHA17522Δ (FIG. 4) was used as the template. The PCR reaction was run using primers designed on the basis of the hemagglutinin coding sequence. The PCR product was separated by electrophoresis and isolated from agarose gel. The obtained fragment was digested with restriction enzymes and then ligated with the vector pDB digested with the NdeI and XbaI restriction enzymes. The ligation product was used to transform *E. coli* NM522 cells. After plasmid DNA isolation from the transformed *E. coli* cells, the presence of the cloned HA17522Δ insert in the vector pDBHA17522Δ (FIG. 7), was confirmed by restriction analysis and the sequence accuracy was verified by sequencing.

Construction of the *E. coli* Z0526 Strain Expressing the HPAIV H5N1 Hemagglutinin Fragment (17-522 Aa, ΔRRRKKR (SEQ ID NO: 2))

Cells of *E. coli* Z0526 were transformed with the pDBHA17522Δ plasmid comprising the verified HA17522Δ coding sequence. The method for competent *E. coli*' cell transformation proposed by Chung and Miller [Chung C T, Miller R H. A rapid and convenient method for preparation and storage of competent bacterial cells. Nucleic Acids Res. 1988 Apr. 25; 16(8):3580] was applied to transform *E. coli* cells. Transformants were selected on LB medium with the addition of tetracycline (12.5 µg/ml).

The product was *E. coli* Z0526 strain expressing the HA17522Δ gene with deletion of the HA0 cleavage region between the HA-1 and HA-2 subunits (ΔRRRKKR). The strain expresses the rH5 recombinant protein comprising the HA-1 subunit and a fragment of the HA-2 subunit and is deprived of the region comprising the RRRKKR SEQ ID NO: 7 amino acids in the 341-346 aa site of the HA antigen. The amino acid sequence of the rH5 protein is shown on FIG. 1.5.

Expression of the HPAIV H5N1 Hemagglutinin Fragment (17-522 Aa, ΔRRRKKR (SEQ ID NO: 2)) in *E. coli* Z0526.

Bacteria *E. coli* Z0526 harboring the recombinant plasmid were cultured in mineral media containing tetracycline (12.5 µg/ml) at 37° C. with shaking (150 rpm) until reaching OD600~1.2 and then centrifuged.

Isolation of Inclusion Bodies Containing rH5 from *E. coli* Z0526

The cell pellet was suspended in lysis buffer (0.5 M NaCl; 0.05 M Tris HCl pH 7.5; 0.01 M EDTA pH 7.5; 0.005 M 2-Mercaptoethanol; 0.35 mg/ml lysozyme; 1% PMSF) and incubated for 30 minutes at 20° C. Triton X-100 was added up to the concentration of 1%. The suspension was sonicated and centrifuged. The inclusion body pellet was suspended in PBS buffer containing 1% Triton X-100 and then in PBS containing 2M urea and centrifuged. The isolated inclusion bodies were washed twice with PBS buffer. Finally, the inclusion bodies were suspended in PBS buffer, divided into batches and frozen at −20° C. for further analysis.

Analysis of Inclusion Bodies Isolated from *E. coli* Z0526

The presence of the fraction of inclusion bodies containing rH5 was confirmed by separating the samples by electrophoresis in 15% polyacrylamide gel (SDS-PAGE). The proteins were visualized with Coomassie Brilliant Blue G. The images for electrophoretic separation of the isolated inclusion bodies samples are shown on FIG. 8.

EXAMPLE 3 REFOLDING AND PURIFICATION OF H5 HEMAGGLUTININ (17-522 AA, ΔRRRKKR (SEQ ID NO: 2)) FROM A BACTERIAL EXPRESSION SYSTEM (RH5-*E. COLI*)

The isolated inclusion bodies were solubilized in DRCI buffer (50 mM TrisHCl, pH 8.0; 8 M urea; 10 mM beta-mercaptoethanol; 0.01% Triton X-100). The inclusion bodies were solubilized for 1-2 h at room temperature. After this time the solution was centrifuged and then filtered through 0.2 μm filters. At this stage protein concentration, as measured by the Bradford method (Bradford, 1976), was 5-6 mg/ml.

The protein solution, obtained by solubilization of inclusion bodies, was loaded onto a 10 ml column with the DEAE Sepharose Fast Flow bed (Amersham Pharmacia Biotech AB). The column with the bed was equilibrated with a calibration buffer (50 mM TrisHCl pH 8.0; 6 M urea; 0.1% Triton X-100). Unbound proteins were eluted with the calibration buffer. Bound proteins were eluted with an elution buffer (50 mM TrisHCl pH 8.0; 6 M urea; 800 mM NaCl). Fractions containing rH5-*E. coli* were collected. The concentration of eluted protein was determined by the Bradford method. An example chromatogram of protein separation at this stage is shown on FIG. 10A.

Proteins eluted from the DEAE Sepharose Fast Flow bed were refolded by diluting in BR buffer (40 mM TrisHCl pH 8.0; 100 mM NaCl). In this refolding method the protein was diluted to 0.07-0.09 mg/ml and then refolding was continued for 15-16 h at 4° C. with mixing. After refolding the solution was filtered through 0.4 μm filters and then protein concentration was determined by the Bradford method. At this stage protein loss was approx. 1-2%, making this developed refolding method particularly efficient. The protein solution after refolding was loaded onto a 7 ml column with the Phenyl Sepharose 6 Fast Flow High Sub bed (Amersham Pharmacia Biotech AB). The column with the bed was equilibrated with a calibration buffer (40 mM TrisHCl pH 8.0; 100 mM NaCl). Unbound proteins were eluted with the calibration buffer, while bound proteins were eluted with deionized water. Fractions containing rH5-*E. coli* were collected. The concentration of eluted protein was determined by the Bradford method. An example chromatogram of the protein separation at this stage is shown on FIG. 10B.

The eluted protein solution was supplemented with 1 M TrisHCl pH 8.0 up to the final concentration of 40 mM and protease inhibitors were added (Sigma, cat. no. P8430) according to the manufacturer's instructions, next the protein solution was filtered through 0.2 μm filters and protein concentration was determined by the Bradford method. The rH5-*E. coli* preparation obtained as above was stored at 4° C.

All purification steps can be performed within the temperature range of 4–24° C.

EXAMPLE 5 ANALYSIS OF PURIFIED AND REFOLDED RH5-*E. COLI*

Polyacrylamide Gel Electrophoresis (SDS-PAGE)

Samples were collected after each step of production of the final rH5-*E. coli* preparation and their composition was analyzed by discontinuous SDS-PAGE electrophoresis under denaturing conditions (Laemmli, 1970). Protein polyacrylamide gel electrophoresis with SDS detergent was run in a discontinuous buffer system, in double polyacrylamide gel set-up (3.5% stacking gel, pH 6.8 and 15% resolving gel, pH 9.2). An example of one such analysis is shown on FIG. 11.

On-Chip Electrophoresis in Bioanalyzer 2100

The quantitative composition of the obtained rH5-*E. coli* preparation was determined using the Agilent 2100 Bioanalyzer (Agilent Technologies) with High Sensitivity Protein 250 kit chips with increased sensitivity. The analysis was performed following the manufacturer's protocol. The method is capable of detecting proteins within the mass range of 10-250 kDa in the tested sample at concentrations starting from 1 pg/μl.

The results obtained by this method indicate a 75-85% rH5-*E. coli* content in the final protein product. An example result of qualitative analysis of the final rH5-*E. coli* preparations is given on FIG. 12 and in Tab. 1.

TABLE 1

| | Mass [kDa] | Concentration [pg/μl] | Peak surface area | Content [%] | Comments |
|---|---|---|---|---|---|
| 1 | 5.0 | 0.0 | 14 461.0 | 0.00 | Lower marker |
| 2 | 10.0 | 28.3 | 24.5 | 1.22 | |
| 3 | 18.5 | 200.4 | 173.3 | 8.60 | |
| 4 | 24.7 | 115.9 | 100.2 | 4.97 | |
| 5 | 39.8 | 60.4 | 52.3 | 2.59 | |
| 6 | 42.8 | 22.8 | 19.8 | 0.98 | |
| 7 | 48.5 | 32.7 | 28.3 | 1.40 | |
| 8 | 58.1 | 1 823.5 | 1 577.1 | 78.23 | HA monomer |
| 9 | 114.3 | 46.8 | 40.5 | 2.01 | HA dimer |

Mass Spectrometry (MS)

The exact mass of the rH5-*E. coli* hemagglutinin was determined using the MALDI TOF/TOF MDS SCIEX 4800 Plus mass spectrometer by Applied Biosystems, using the CHCA matrix, i.e. α-cyano-4-hydroxycinnamic acid (Fluka 70990-1G-F).

The rH5-*E. coli* molecular mass, determined using MS, is 56.7 kDa (FIG. 13).

Antibodies for Analyses of rH5-*E. coli* Antigenicity

Antigenicity of purified and refolded HA (17-522 aa, ΔRRRKKR (SEQ ID NO: 2)), produced by overexpression in *E. coli* (rH5-*E. coli*) was analyzed using commercially available monoclonal and polyclonal antibodies against AIV H5 HA. The monoclonal antibodies (Mabs) were supplied by the following companies: *Acris* Antibodies (5 clones), ABR/Thermo Scientific (1 clone) and USBiological (3 clones). Mabs were obtained with purified AIV H5N1 (8 clones) or recombinant AIV H5N1 HA from the A/Vietnam/1203/04 strain (1 clone) as immunogens. According to the manufacturers' specifications, the antibodies, referred to as Mab 1-2 and 6-9, react with the following influenza viruses: H5N1, H5N2 and H5N9, with H5 HA in the HI test and do not cross-react with hemagglutinins of serotypes other than H5. The specificity of the other Mab clones is described as capacity to recognize the H5 antigen in viral samples (Mab 3) or in the HI test (Mab 5). According to the manufacturer's data, the antibodies, referred to as Mab 4, are specific towards HA from A/Vietnam/1203/04 (H5N1) AIV, react with H5N1 influenza viruses of different strains (clades, subclades) and do not cross-react with hemagglutinins of other subtypes. Specifications for all the used Mab indicate that the antibodies recognize conformational epitopes. Immunoreactivity assays were also conducted with polyclonal antibodies (Pabs) against the HA-1 and HA-2 subunits of H5 HA. The antibodies, referred to as Pab 1 and Pab 2, were obtained using HA-1 (1-345 aa) from A/Bar-headed Goose/Qinghai/12/05(H5N1) and a HA-2 subunit fragment (347-523 aa) from A/VietNam/1203/2004(H5N1) (Immune Technology Corp.) as respective immunogens. It may be expected that the Pabs against HA will recognize both conformational and linear epitopes of the protein.

In order to determine the specificity of Mabs and Pabs to be used in analyses of rH5-*E. coli* properties, their reactivity was tested using commercially available recombinant hemagglutinins from different AIV strains. Based on the A/swan/Poland/305-135V08/2006(H5N1) HA sequence, a 17-530 aa fragment of the protein with deletion of the cleavage site (ΔRRRKKR) and a histidine tag-6×His (Oxford Expression Technologies) conjugated at C-terminus was produced in a baculovirus expression system. The hemagglutinins from 5 H5N1 and 1 H5N2 IV strains, used in the tests performed, were produced in a mammalian expression system without the signal sequence, the transmembrane or the cytoplasmic domains of the protein (Immune Technology Corp.). The HA fragments (17-530 aa, 18-530 aa or 19-506 aa), comprising the HA-1 subunit and a HA-2 subunit fragment, constituted the antigen. In 4 out of 5 hemagglutinins the cleavage site (ΔRRRKKR) was deleted and these proteins are, according to the specification, found primarily in the form of trimers/oligomers. Oligomerization of the produced antigens renders them similar to the HA in the viral envelope, where the protein is found in the form of trimers.

The set of hemagglutinins to be used in analyses of antibody reactivity against H5, included also recombinant HA fragments corresponding to the HA-1 subunit (Immune Technology Corp.), which in the native protein comprises essential protein neutralizing epitopes and is characterized by a greater sequence variation than the HA-2 subunit. The recombinant HA-1 from the selected H5N1 virus strains were expressed in mammalian cells with (1-345 aa) or without (17-346 aa) the signal sequence. The conformation of HA fragments corresponding to the HA-1 subunit was not specified. All recombinant hemagglutinins produced in a mammalian expression system comprised the histidine tag-6×His.

Analyses of Mab and Pab specificity against recombinant hemagglutinins from different H5 influenza virus strains were conducted by ELISA using Ni-NTA plates (Qiagen). HA proteins were applied to the plates, diluted in 1% BSA/PBS to 1 μg/ml and incubated overnight at 2-8° C. To control the level of nonspecific binding of the antibodies, some wells on the plate were filled with 1% BSA/PBS and incubated in parallel with the antigen coated wells. Anti-H5 Mab and Pab were added to the plates, diluted to 1 μg/ml in 2% BSA/PBS and incubated overnight at 2-8° C. Polyclonal antibodies against mouse IgG antibodies, specific towards the whole molecule, labeled with HRP (Sigma) or HRP-labeled monoclonal antibodies against rabbit IgG antibodies, specific towards the γ chain (Sigma) were used to develop plates. Secondary antibodies were diluted to 1:1000 with 1% BSA/PBST and incubated on plates at room temperature for 45 minutes. TMB (Sigma) was used as horseradish peroxidase substrate. The reaction was stopped after 30 minutes with 1.25 M $H_2SO_4$ solution. Sample absorption was read at 2=450 nm. The ELISA was not optimized for individual antigens and antibodies.

The results of reactivity analyses for the antibodies with rH5 from different H5 AIV strains are shown in Tab. 2 together with data concerning hemagglutinins used (EpiFlu-Database, GenBank Accession No., HA fragment, expression system for protein production, manufacturer). Hemagglutinin homology shown in Tab. 2 was established in relation to A/swan/Poland/305-135V08/2006(H5N1) HA, to the full-length protein (1-568 aa) and to the HA-1 subunit (17-340 aa). The hemagglutinins used in the assays were characterized by diverse homology with the HA from the Polish AIV isolate—from very high, as in the case of hemagglutinins from the H5N1 AIV: A/Bar-headed Goose/Qinghai/12/05 and A/chicken/India/NIV33487/2006, to the lowest, as demonstrated for the H5N2 AIV HA: A/American greenwinged teal/California/HKWF609/2007.

TABLE 2

| | Homology identical/tested % | | Mab against HA H5 (Mab 1-9) | | | | | | | | | |
|---|---|---|---|---|---|---|---|---|---|---|---|---|
| | HA | HA-1 | | | | | | | | | | |
| No. | 1-568 aa | 17-340 aa | Mab 1* | Mab 2* | Mab 3** | Mab 4*** | Mab 5*** | Mab 6* | Mab 7* | Mab 8*** | Pab 1**** | Pab 2**** |
| 1 | 568/568 100% | 324/324 100% | >4 | >4 | >4 | 0.8 | >4 | >4 | 3.6 | 3.8 | 0.2 | 0.1 |
| 2 | 562/566 99% | 322/324 99% | >4 | >4 | >4 | >4 | >4 | >4 | >4 | >4 | 1.1 | 2.2 |
| 3 | 564/568 99% | 322/324 99% | >4 | >4 | >4 | >4 | >4 | >4 | >4 | >4 | 1.1 | 2.1 |
| 4 | 549/568 96% | 308/324 99% | >4 | >4 | >4 | >4 | >4 | >4 | 0.3 | 0.2 | 1.3 | 1.6 |
| 5 | 522/556 93% | 300/324 92% | >4 | >4 | >4 | >4 | 1.4 | 0.0 | 0.3 | 0.1 | 1.1 | 1.4 |

TABLE 2-continued

| | Homology identical/tested % | | | | | | Mab against HA H5 (Mab 1-9) | | | | | |
|---|---|---|---|---|---|---|---|---|---|---|---|---|
| | HA | HA-1 | | | | | | | | | | |
| No. | 1-568 aa | 17-340 aa | Mab 1* | Mab 2* | Mab 3** | Mab 4*** | Mab 5*** | Mab 6* | Mab 7* | Mab 8*** | Pab 1**** | Pab 2**** |
| 6 | 506/568 89% | 285/324 87% | >4 | >4 | >4 | >4 | 3.4 | >4 | 0.3 | 0.2 | 0.3 | 0.5 |
| 7 | — | 308/324 99% | >4 | >4 | >4 | >4 | 3.8 | 0.0 | 0.0 | 0.0 | 0.2 | 0.1 |
| 8 | — | 303/324 93% | >4 | >4 | >4 | >4 | 0.6 | 0.0 | 0.0 | 0.0 | 0.2 | 0.1 |
| 1 | HA (H5N1) (A/swan/Poland/305-135V08/2006), EpiFluDatabase Accession No. EPI156789 HA (17-530 aa, ΔRRRKKR, 6xHis) - baculoviral (Oxford Expression Technologies) | | | | | | | | | | | |
| 2 | HA (H5N1) (A/Bar-headed Goose/Qinghai/12/05), Genbank Accession No. ABE68927 HA (17-530 aa, ΔRRRKKR, 6xHis) - mammalian (Immune Technology Corp.) | | | | | | | | | | | |
| 3 | HA (H5N1) (A/chicken/India/NIV33487/2006), Genbank Accession No. ABQ45850 HA (17-530 aa, ΔRRRKKR, 6xHis) - mammalian (Immune Technology Corp.) | | | | | | | | | | | |
| 4 | HA (H5N1) (A/Vietnam/1203/2004), Genbank Accession No. AAW80717 HA (18-530 aa, ΔRRRKKR, 6xHis) - mammalian (Immune Technology Corp.) | | | | | | | | | | | |
| 5 | HA (H5N1) (A/goose/Guiyang/337/2006), Genbank Accession No. ABJ96698 HA (17-530 aa, ΔRRRKKR, 6xHis) - mammalian (Immune Technology Corp.) | | | | | | | | | | | |
| 6 | HA (ΔTM) (H5N2), Genbank Accession No. ACF47563 HA (19-506 aa, ΔRRRKKR, 6xHis) - mammalian (Immune Technology Corp.) | | | | | | | | | | | |
| 7 | HA1 (H5N1) (A/Vietnam/1203/2004), Genbank Accession No. AAW80717 HA-1 (1-345 aa, 6xHis) - mammalian (Immune Technology Corp.) | | | | | | | | | | | |
| 8 | HA1 (H5N1) (A/Hong Kong/483/97), Genbank Accession No. AAC32099 HA-1 (17-346 aa, 6xHis) - mammalian (Immune Technology Corp.) | | | | | | | | | | | |

*Acris Antibodies,
**ABR/Thermo Scientific,
***USBiological Pab against the subunits: HA-1 (Pab 1), HA-2 (Pab 2)
****Immune Technology Corp.

Monoclonal antibodies 1-5 bound to all rH5 used in the test (17-530 aa, ±ΔRRRKKR) and the rHA-1 (1-345 aa, 17-346 aa) from a mammalian expression system, while Mab 1-4 recognized all antigens with high affinity ($A_{450}>4$). Monoclonal antibodies 6-8 demonstrated specificity towards some mammalian rH5, including HA with high homology with the Polish AIV isolate HA. Most mammalian rH5 immobilized on the Ni-NTA plate were detected by polyclonal antibodies (Pab 1, 2). Seven out of eight tested Mabs recognized rH5 (17-530 aa, ΔRRRKKR) from a baculovirus expression system with high affinity. Reactivity of Mab 4, Pab 1 and Pab 2 with the baculoviral rH5 was much lower than with proteins of similar lengths from a mammalian expression system, which probably resulted from the differences in binding of these antigens on the Ni-NTA plates.

Immunoreactivity assays for monoclonal (Mab) and polyclonal (Pab) antibodies with rH5 and rHA-1 (Tab. 2) produced in a eukaryotic expression system, combined with data from the specifications of used Mabs, Pabs and rH5 HAs, indicate that:

Mabs recognize hemagglutinins with native protein properties, so that they can be used in rH5 conformation analyses, Mabs recognize different HA epitopes, so that they may be used to test various rH5 antigenic determinants, most Mabs have the capacity to inhibit erythrocyte agglutination by H5 HA, hence they may be used in testing an antigen for the presence of epitopes essential for induction of HI antibodies, which in turns facilitates evaluation of rH5 vaccine potency, some Mabs demonstrate properties of antibodies specific towards the hemagglutinin H5 serotype—their application in rH5 analyses makes it possible to verify whether essential neutralizing HA epitopes are preserved in rH5 and thus whether the obtained antigen is a valuable immunogen, Mabs with limited specificity towards hemagglutinins of different AIV strains recognize rH5 with the sequence identical or similar to the sequence from the A/swan/Poland/305-135V08/2006 (H5N1), making them applicable in analyses of rH5-*E. coli* produced on the basis of the HA sequence from the Polish AIV isolate, Mab 4, Pab 1 and Pab 2 differentiate rH5 in a manner independent (Mab 4) or only partially dependent (Pab 1, 2) on the HA sequence, hence they may be used in comparative studies on antigens of different origin.

Immunoreactivity determined for antibodies against H5 HA with rH5 of diverse homology confirmed the applicability of the tested Mabs and Pabs in analyzing of rH5-*E. coli* properties and confirmed the interpretation of the recorded results.

rH5-*E. coli* Antigenicity

Analyses of rH5-*E. coli* properties with a panel of Mabs and Pabs against H5 HA with the above described specificity were conducted in the presence of two reference antigens. One of those was the H5 HA fragment (17-530 aa, ΔRRRKKR, 6xHis), produced in a baculovirus expression system (Oxford Expression Technologies) based on the HA sequence from the same AIV strain as rH5-*E. coli* (A/swan/Poland/305-135V08/2006(H5N1)). The other reference antigen was the HA fragment (17-530 aa, ΔRRRKKR, 6xHis) from A/Bar-headed Goose/Qinghai/12/05(H5N1), produced in a mammalian expression system (Immune Technology Corp.). The Qinghai HA sequence was the most similar to that of the Polish AIV isolate among the commercially available HA produced in a mammalian expression system. Protein homology measured by the number of identical amino acids is 99%, while the conservative amino acid replacement is found in the signal sequence, whereas the other 3 replacements are semiconservative and are in the HA-1 and HA-2 subunits of the protein. According to the specification, the protein, purified to at least 95%, is found primarily in the form of trimers/oligomers. In contrast to rH5-*E. coli*, reference hemagglutinins produced in an eukaryotic expression system are glycosylated proteins, similarly to native AIV HA.

Antigenicity of rH5-*E. coli* was analyzed in the presence of reference antigens by ELISA method. MediSorp (NUNC) plates were coated with rH5-*E. coli*, mammalian rH5 and baculoviral rH5 at 5 µg/ml PBS at 2-8° C. overnight. Nonspecific binding sites on the plates were blocked using 10% FBS/PBS. Anti-H5 Mabs and Pabs diluted to 1 µg/ml (Mab) or 10 µg/ml (Pab) in 2% BSA/PBS were applied to the plates. The plates were incubated overnight at 2-8° C. To detect antigen-bound Mabs the HRP-labeled polyclonal antibodies against murine IgG antibodies, specific towards the γ chain (Sigma), were used diluted to 1:1000 in 2% BSA/PBS. To detect antigen-bound Pabs the HRP labeled monoclonal antibodies against rabbit IgG antibodies, specific towards the γ chain (Sigma) were used, diluted 1:1000 in 1% BSA/PBS. Secondary antibodies were incubated on the plates for 1 hour at 37° C. TMB (Sigma) was used as HRP substrate. The reaction was stopped after 30 minutes with a 0.5 M H2SO4 solution. Absorption of the samples was read at λ=450 nm.

Analyses of rH5-*E. coli* have shown that the HA from a bacterial expression system is recognized by all used antibodies, similarly to reference hemagglutinins (FIG. 14). Differences in immunoreactivity for anti-H5 antibodies with recombinant proteins were observed when Mab 4 and Pab 2 were used (against the HA-2 subunit) as detection antibodies. Reactivity of these antibodies with rH5-*E. coli*, measured as $A_{450}$ level, was comparable to their reactivity with mammalian rH5 and higher than with baculoviral rH5. In specificity assays of anti-H5 Mabs and Pabs towards rH5 from the bacterial (rH5-*E. coli*) and eukaryotic expression systems (mammalian and baculoviral rH5), conducted by ELISA as described above, protein glycosylation was not found to influence reactivity of the used antibodies with hemagglutinins. Results for the analyses of HA (17-522 aa, ΔRRRKKR (SEQ ID NO: 2) from a bacterial expression system—rH5-*E. coli* (FIG. 14), conducted using antibodies with previously determined specificity profiles (Tab. 2), simultaneously with mammalian rH5 (17-530 aa, ΔRRRKKR, 6×His) having the native antigen characteristics, demonstrate that rH5-*E. coli* has the properties of H5 HA. Serotype-specific neutralizing epitopes and HI antibody binding epitopes, essential for the vaccine HA, are retained in the produced protein.

Hemagglutination Assay (HA)

Hemagglutinin with the correct conformation has the oligomerization capacity, as it is found in the native form as trimer. Such protein complexes have erythrocyte agglutinating properties, which is utilized in the hemagglutination assay (HA). Erythrocytes that are agglutinated do not settle at the bottom, but form a uniform suspension. Non-agglutinated erythrocytes precipitate rapidly, forming a distinct red dot at the bottom of the test tube. This test is a simple method of evaluating HA antigen quality.

In the test, a fresh preparation of erythrocytes collected from blood of SPF chickens was used, obtained from a sterile culture at the Department of Poultry Diseases, the National Veterinary Research Institute (NVRI) in Pulawy. The hemagglutination test was performed using a 0.5% chicken erythrocyte suspension in PBS on 96-well V-bottomed plates by Cellstar. Each cell was supplemented with 50 µl PBS, followed by a suitable amount of antigen and made up to 100 µl with PBS. Subsequently, 50 µl of 0.5% chicken erythrocyte suspension in PBS was added to each well and mixed gently by pipetting. The plates were incubated at 20° C. for 45 min. and then the result was read. The AI-H5N2 virus (x-OvO) was used as positive control. Negative controls were: 50 mM TrisHCl pH 8.0; 50 mM TrisHCl pH 8.0 with 30 mM β-mercaptoethanol; PBS and the rH5-*E. coli* protein reduced with 30 mM β-mercaptoethanol.

To compare rH5-*E. coli* with hemagglutinins from other expression systems, rH5 HA (17-530 aa, ΔRRRKKR, 6×His): from the same AIV strain as rH5-*E. coli* (A/swan/Poland/305-135V08/2006(H5N1), produced in a baculovirus expression system by Oxford Expression Technologies (OET) and from AIV A/Bar-headed Goose/Qinghai/12/05 (H5N1), produced in a mammalian expression system by Immune Technology Corp. (ITC) were also tested in the hemagglutination assay. Hemagglutinins tested in the HA assay were also used as reference antigens in the antigenicity analyses described above for rH5-*E. coli*. According to the specification, rH5 from a mammalian expression system (ITC), with purity of at least 95%, was found primarily as trimer/oligomer.

The HA assay conducted with chicken erythrocytes showed that rH5-*E. coli* exhibits the hemagglutinating capacity, similarly to baculoviral rH5 and mammalian rH5 (Tab. 3). For complete agglutination of chicken erythrocytes, a lower concentration of the rH5-*E. coli* protein than of the HA from a baculovirus expression system is required. The obtained results indicate that the produced rH5-*E. coli* protein is at least partially found in the form of oligomers, which is an advantageous characteristic for a vaccine HA.

TABLE 3

| rH5-expression system | Amount of hemagglutinin in HA assay | | | | | | |
|---|---|---|---|---|---|---|---|
| | 10 µg | 5 µg | 2.5 µg | 1 µg | 0.5 µg | 0.25 µg | 0.1 µg |
| rH5-*E. coli* | + | + | + | + | + | − | − |
| rH5-*E. coli* reduced | − | − | − | − | − | − | − |
| rH5-BEVS (OET) | + | + | + | +/− | − | − | − |
| rH5-mammalian (ITC) | + | + | + | + | + | + | + |

EXAMPLE 6 PREPARATION OF VACCINE CONTAINING RH5-*E. COLI*, CHICKEN IMMUNIZATION AND COLLECTION OF SAMPLES FOR SEROLOGICAL ANALYSES

To evaluate the applicability of purified and refolded HA (17-522 aa, ΔRRRKKR (SEQ ID NO: 2)) as a vaccine antigen, produced by overexpression in *E. coli* (rH5-*E. coli*), a vaccine composition was developed using rH5-*E. coli* and immunization trials were performed on chickens as one of the target groups for vaccinations against avian influenza.

To prepare a vaccine against avian influenza using rH5-*E. coli*, aluminium hydroxide was used as an adjuvant. Protein content in rH5-*E. coli* preparations for vaccine production was determined by the Bradford method. The HA content in rH5-*E. coli* preparations was estimated on the basis of its quantitative composition, analyzed using increased sensitivity chips of the High Sensitivity Protein 250 kit and the Agilent 2100 Bioanalyzer by Agilent Technologies. The result of the analysis for one of the protein preparations is shown in Tab. 1. To prepare the vaccine, an rH5-*E. coli* preparation was used in the amount providing the desired rH5 concentration per dose. Aluminium hydroxide—1.3% Alhydrogel (Brenntag) constituted ¼ of the vaccine volume. The rH5-*E. coli* preparation was added to aluminium hydroxide gel in PBS, shaken on a vortex mixer at 2500 rpm for 5 minutes and then incubated at room temperature for 20 min. Following incubation, the vaccine was again shaken on a vortex mixer for 5 minutes at 2500 rpm. The vaccine was prepared directly before vaccination.

Immunization trials using rH5-*E. coli* were conducted under commercial rearing conditions on broiler-type Ross 308 chickens. Experiments were performed in parallel on 4 animal groups designated A, B, C and K. Chickens in groups A, B and C, with 8 animals in each, were vaccinated, while 15 non-immunized chicken constituted the control (K). The first immunization was performed at day 7 of life. Group A chickens were given one antigen dose, whereas groups B and C were administered two doses. Group B chickens were booster vaccinated at day 21 of life, i.e. 2 weeks after the administration of priming vaccination, while group C at day 35 of life, i.e. 4 weeks after primary vaccination. In chicken immunizations identical antigen doses were used for all groups, administered in the same manner. One vaccine dose contained 25 µg rH5-*E. coli* and aluminium hydroxide as an adjuvant. Vaccine was administered subcutaneously in three areas on the back of the neck in volume of 200 µl.

To monitor chickens' response to immunization, blood was collected from the vaccinated animals at days 21, 35, 42 and 48 of life. Thus samples for serological analyses were prepared from the following stages of the experiment in individual groups: in group A—2, 4, 5 and 6 weeks after immunization, in group B—2 weeks after priming immunization and 2, 3 and 4 weeks after booster immunization, while in group C—2 and 4 weeks after priming immunization and 1 and 2 weeks after booster immunization. Samples collected in parallel from non-vaccinated chickens were the control material. Blood, collected from the wing vein was left to coagulate at room temperature for 1 h and 30 min., afterwards it was stored at 2-8° C. to allow for clotting. Serum, obtained by clot centrifugation (5000×g, 10 min., 4° C.) was aliquoted and stored at −70° C. until analysis. Chicken immunization and blood collection schedules for vaccinated and control animals were performed according to regimen A (FIG. 31).

Sera prepared during the experiments were analyzed using indirect and competitive ELISA to detect antibodies against H5 HA of AIV. Serum samples were also analyzed for the erythrocyte agglutination inhibition activity by homologous HPAIV H5N1 and heterologous LPAIV H5N2 (HI). The assays were performed on serum samples from all blood collections or from blood collected from selected experiment stages. Some samples were not analyzed in all tests due to a lack or insufficient amounts of serum, which is indicated in figures and in tables as n.a.

EXAMPLE 7 IMMUNE RESPONSE ANALYSIS WITH ELISA

Serological analyses of the samples collected during the immunization experiments described in Example 6 were carried out by ELISA to detect antibodies against H5 HA of AIV: an indirect one (H5-ELISA) and the competitive one (FLUAc H5, IDVet).

Indirect ELISA (H5-ELISA)

Indirect ELISA (H5-ELISA) was designed using recombinant HA H5 (17-530 aa, ΔRRRKKR, 6×His) homologous to the vaccine antigen and it was produced in a baculovirus expression system (Oxford Expression Technologies). Anti-HA antibody levels were treated as the main indicator of chicken humoral response to the vaccination and of rH5-*E coli* immunogenicity.

To carry out the H5-ELISA test, MediSorp plates (NUNC) were coated with rH5 (17-530 aa, ΔRRRKKR, 6×His) of (A/swan/Poland/305-135V08/2006(H5N1)) from a baculovirus expression system (Oxford Expression Technologies) at 3 μg/ml of PBS or were filled with PBS (non-specific binding control). The plates were incubated overnight at 2-8° C. and then blocked with "Protein-Free T20 (PBS) Blocking Buffer" (Pierce/Thermo Scientific) for 1 h at room temperature. Chicken sera were diluted 1:200 using 2% BSA/PBSS (phosphate buffer containing 0.3 M NaCl+KCl). In order to determine the endpoint titer, sera from individual blood collections from the analyzed chicken group were pooled and then serially diluted in 2% BSA/PBSS. The plates with serum samples and control samples—BLK (2% BSA/PBSS) were incubated overnight at 2-8° C. Assay development involved 1-hour incubation at 37° C. with HRP labeled antibodies against IgY chicken antibodies, specific towards the Fc fragment (Pierce/Thermo Scientific), diluted at 1:13000. Plates were washed with PBS buffer with Tween 20 at 0.05% (PBST) or 0.1% (PBSTT). The PBSTT buffer was used to wash only the plates with serum samples. After coating, 4 washing cycles were used, 2 after blocking and 5 between the other stages of the procedure. Color reaction for horseradish peroxidase was developed using TMB (Sigma). Plates were incubated with substrate for 30 minutes and then 0.5 M H2504 solution was added to stop the HRP reaction. Sample absorption was read at λ=450 nm.

The $A_{450}$ values obtained for the BLK samples were subtracted from the $A_{450}$ values measured for serum samples. Assay results for sera on plates not coated with rH5 constituted the control for the non-specific serum binding levels (background). Serum samples were considered H5-positive if the $A_{450}$ value for the samples was higher than the mean $A_{450}$ value for the control increased by the doubled standard deviation value (cut off). The endpoint titer was defined as the highest dilution of an immunized chicken serum giving an absorption value 4-times higher than the mean absorption value for the control.

H5-ELISA Results

Analyzing the chicken humoral response to subcutaneous administration of one 25 μg-dose of rH5-*E. coli* in the presence of aluminium hydroxide, conducted using the H5-ELISA on samples collected 2, 4, 5 and 6, and 2 or 2 and 4 weeks after immunization in chicken groups A, B and C showed the presence of IgY antibodies against H5 in sera diluted 200-fold from 23 out of 24 (96%) immunized animals (FIGS. 15, 16, 17). The high detection rate of the antigen-specific antibodies in substantially diluted samples indicates that the rH5-*E. coli* vaccine has good priming properties.

In 6 out of 8 (75%) group A animals vaccinated once with rH5-*E. coli* the anti-H5 antibody levels were the highest 2 weeks after immunization (FIG. 15). The H5-specific antibody levels in sera of these animals decreased in each consecutive analysis, so that 5 and 6 weeks after immunization the antibodies were not detected in the sera of most chickens in this group at sample dilution 1:200. The highest H5-specific antibody levels 2 weeks after administration of the first antigen dose and decreasing between week 2 and 4 after immunization was also observed in group C as well (FIG. 17). This regularity concerned all animals shown to be seropositive after the first vaccination (7/7). The similarity in the kinetics of primary immune response in chickens to the administration of the rH5-*E. coli*-containing vaccine is advantageous for optimization and standardization of vaccinations. Chicken immunization trials with one 25 µg rH5-*E. coli* dose and aluminium hydroxide as an adjuvant (FIGS. 15, 17) demonstrated good priming properties of the applied vaccine, but also showed that a single vaccination of animals is insufficient to elicit humoral response sufficiently strong to provide immunity against AIV infection.

Serological analyses of chickens after subcutaneous priming immunization with 25 µg of rH5-*E. coli* and aluminium hydroxide as an adjuvant, conducted using the H5-ELISA on samples collected directly before administering the booster dose of the antigen, i.e. 2 or 4 weeks after priming vaccination of group B and C chickens, demonstrated detectable IgY antibodies against H5 in sera diluted 1:200 amounting to 100% and 50%, respectively (FIGS. 6.2, 6.3). Two weeks after administration of booster vaccination with rH5-*E. coli* to group B chickens and one week after the second immunization of group C chickens, a considerable increase of serum antibody levels was observed in all vaccinated animals, typical of a secondary immune response (FIGS. 6.2, 6.3). High serum anti-H5 antibody levels in animals vaccinated twice, substantially exceeding antibody levels induced by a single vaccination, were observed during the whole study period. In group C chickens minor fluctuations in serum antibody levels were observed within 2 weeks after the booster dose (FIG. 6.3). In group B chickens serum anti-H5 antibody levels gradually decreased between the 2nd and the 4th week after the repeated antigen dose administration (FIG. 16).

Assays of the endpoint titer in sera analyzed 2, 3 and 4 weeks after administering the II antigen dose to group B chickens and 1 and 2 weeks after administering the 2nd antigen dose to group C chicken, demonstrated that rH5-*E. coli* induces a high titer of IgY antibodies against H5 at the second subcutaneous administration of the antigen in the presence of aluminium hydroxide (FIG. 18). The highest mean titer for these antibodies, i.e. 1:129200, was found in sera collected 1 week after the second immunization in group C chickens, vaccinated twice at a 4-week interval. Between the $1^{st}$ and the $2^{nd}$ week after the second immunization in this animal group, the mean titer for H5-specific antibodies decreased 1.6-fold. In group B chickens, vaccinated twice at a 2-week interval, the endpoint titer of the sera collected 2 weeks after booster dose administration was 1:28300 and was 2.8-fold lower than the serum titer in group C chickens, recorded 2 weeks after booster vaccination. Three weeks after the second immunization anti-H5 antibody titer in sera of group B chickens decreased 2.3-fold. A significantly lower titer for these antibodies, i.e. 1:1600, was found in sera of group B animals 4 weeks after immunization.

Competitive ELISA (FLUAc H5, IDVet)

To detect antibodies against H5 HA, a commercially available ELISA "IDScreen® Influenza H5 Competition ELISA kit" (FLUAc H5, IDVet) was also used. The assay is used in the diagnostics of H5 serotype AIV infections in birds. Results of this assay were considered as an indicator for the induction of antibodies recognizing a presumably serotype-specific, neutralizing conformational AIV epitope. The FLUAc H5 test, beside the HI test, provided a functional evaluation of antisera produced as a result of vaccination with rH5-*E. coli* and potency of HA vaccine (17-522 aa, ΔRRRKKR (SEQ ID NO: 2)), produced in a bacterial expression system.

The FLUAc H5 test was conducted according to the manufacturer's (IDVet) instructions, applying the conditions that enhance test sensitivity (serum samples diluted 1:5, incubated on plates overnight at 2-8° C.). Each analysis of serum samples from rH5-*E. coli* immunized chickens met the test's validation requirements. The competition level was determined by calculating the ratio of mean absorption values of the analyzed samples at λ=450 ($A_{450}$) to the mean $A_{450}$ value for the negative control (NC). The competition values for serum samples were expressed in percent. According to the FLUAc H5 manufacturer's data, competition values of ≥40%, between 35 and 40% and ≤35% indicate that the samples are seronegative, doubtful and seropositive, respectively.

FLUAc H5 Assay Results

Analysis of humoral response in group A chickens to subcutaneous administration of 25 μg of rH5-*E. coli* in the presence of aluminium hydroxide, conducted using the FLUAc H5 test on samples having the highest anti-H5 IgY antibody levels in individual chickens (FIG. 15), demonstrated a lack or at most a slight competition in the analyzed sera (Tab. 4.1). The calculated competition values for sera in this group were within the 73-103% range. Competition values higher than 90% were shown for 5 out of 8 vaccinated chickens and for the other 3 animals it was below 90% (73% or 82%). None of the analyzed sera met the limits to be classified as positive or doubtful, according to the FLUAc H5 test criteria.

The serological analysis conducted using the FLUAc H5 test on samples collected 2, 3 and 4 weeks after booster immunization in group B chickens vaccinated subcutaneously twice at a 2-week interval with 25 μg-doses of rH5-*E. coli* in the presence of aluminium hydroxide, demonstrated varied competition levels for the analyzed sera (Tab 4.2). The calculated competition levels for serum samples from group B chickens were 47-97% (Tab. 4.2) and were usually lower than those recorded in the group of chickens immunized once (Tab. 4.1). None of the analyzed sera from the group vaccinated twice at a 2-week interval was positive or doubtful, according to the FLUAc H5 test classification criteria.

The competition percentage values for individual group B animals increased in successive assays (Tab. 4.2). As a result, the range of serum competition values obtained 2 weeks after booster immunization (47-69%) shifted towards higher values with time from the second immunization, amounting to 59-86% after 3 weeks and 72-97% 4 weeks from the 2nd antigen dose administration. Results of the analyses, obtained with the FLUAc H5 test (Tab. 4.2) indicate a decrease in the levels of antibodies recognizing a presumably serotype-specific epitope in group B chicken sera within 4 weeks after the second immunization, which may be associated with a decrease in total levels of anti-H5 antibodies in the sera, shown by H5-ELISA (FIG. 16).

TABLE 4.1

| | FLUAc H5 competition | |
|---|---|---|
| ID | % | result |
| A-1* | 82 | – |
| A-2* | 73 | – |
| A-3* | 92 | – |
| A-4* | 82 | – |
| A-5** | 103 | – |
| A-6* | 101 | – |
| A-7* | 102 | – |
| A-8*** | 103 | – |

TABLE 4.1-continued

| ID | FLUAc H5 competition | |
|---|---|---|
| | % | result |
| Group A | 73-103 | – |
| 35% < competition < 40% doubtful | 0/8 (0%) | |
| competition ≤ 35% seropositive | 0/8 (0%) | |

*2 weeks after immunization with rH5
**4 weeks after immunization with rH5
***5 weeks after immunization with rH5

TABLE 4.2

| | FLUAc H5 After 2nd dose of rH5 | | | | | |
|---|---|---|---|---|---|---|
| | 2 weeks competition | | 3 weeks competition | | 4 weeks competition | |
| ID | % | result | % | result | % | result |
| B-1 | 69 | – | 68 | – | 91 | – |
| B-2 | 67 | – | 86 | – | 97 | – |
| B-3 | 48 | – | 63 | – | 73 | – |
| B-4 | n.a. | n.a. | 62 | – | 78 | – |
| B-5 | n.a. | n.a. | 68 | – | 84 | – |
| B-6 | 56 | – | 82 | – | 94 | – |
| B-7 | n.a. | n.a. | 59 | – | 72 | – |
| B-8 | 47 | – | 70 | – | 87 | – |
| Group B | 47-69 | – | 59-86 | – | 72-97 | – |
| 35% < competition < 40% doubtful | 0/5 (0%) | | 0/8 (0%) | | 0/8 (0%) | |
| competition ≤ 35% seropositive | 0/5 (0%) | | 0/8 (0%) | | 0/8 (0%) | | n.a.—not available

The analyses performed on samples collected 1 and 2 weeks after booster immunization from group C chickens, vaccinated twice subcutaneously with 25 μg of rH5-*E. coli* and aluminium hydroxide as an adjuvant at an interval of 4 weeks, demonstrated competitive activity against the FLUAc H5 test antibodies for a large proportion of analyzed sera (Tab. 4.3). The competition range for group C chicken sera was 10-95% (Tab. 4.3) and included markedly lower values than those obtained in group B chickens, vaccinated twice at a 2-week interval (Tab. 4.2). Among the 14 analyzed group C sera, 7 samples showed competition % below 40% (Tab. 4.3), indicating that the samples are positive or doubtful, according to the test classification. These samples were collected from 5 out of 8 examined chickens, among which 3 should be considered seropositive according to the FLUAc H5 test criteria (competition ≤35%). The seropositivity of the other 2 chickens was doubtful, since samples of their collected sera showed competition at 37 and 38%.

In 3 of the analyzed group C chickens, serum competition % decreased by 6-13% between the 1″ and the 2nd week after booster dose administration and in 3 others it increased during that time by 4-9% (Tab. 4.3). Slight fluctuations in antibody levels within 2 weeks after booster immunization were also observed in the H5-ELISA detecting total anti-H5 antibody levels (FIG. 17). Results of serum analyses for animals vaccinated twice with rH5-*E. coli* at a 4-week interval (Tab. 4.3) indicate potency of the applied vaccine in inducing active antibodies in the FLUAc H5 test, which titer may match that associated with bird AIV infection.

TABLE 4.3

| | FLUAc H5 After 2nd rH5 dose | | | |
|---|---|---|---|---|
| | 1 week competition | | 2 weeks competition | |
| ID | % | result | % | result |
| C-1 | 38 | ± | 25 | + |
| C-2 | 34 | + | 43 | – |
| C-3 | 50 | – | 37 | ± |
| C-4 | 55 | – | n.a. | n.a. |
| C-5 | 10 | + | 14 | + |
| C-6 | 44 | – | 38 | ± |
| C-7 | 95 | – | n.a. | n.a. |
| C-8 | 82 | – | 91 | – |
| Group C | 10-95 | +, ±, – | 14-91 | +, ±, – |
| 35% < competition < 40% doubtful | 1/8 (12.5%) | | 2/6 (33%) | |
| competition ≤ 35% seropositive | 2/8 (25%) | | 2/6 (33%) | | n.a.—not available

Summary

The analysis of humoral response in broiler-type Ross 308 chickens to subcutaneous administration of one or two doses of vaccine containing 25 μg of rH5-*E. coli* and aluminium hydroxide as an adjuvant, performed by ELISAs (H5-ELISA, FLUAc H5) demonstrated that:
  recombinant H5 HA (17-522 aa, ΔRRRKKR (SEQ ID NO: 2)) from a bacterial expression system—rH5-*E. coli* is strongly immunogenic,
  the vaccine has good priming properties—it elicits primary humoral response in chickens, with a similar kinetics between individuals, which is advantageous for vaccination optimization and standardization,
  two vaccine doses are required, but also sufficient to elicit a strong humoral response in all vaccinated chickens (H5-positive/analyzed—16/16),
  immunizations of chickens with rH5-*E. coli* repeated twice at a 4-week interval are much more effective in inducing anti-H5 IgY antibodies and anti-H5 antibodies competing with the FLUAc H5 test antibodies, than the immunizations performed at a 2-week interval,
  the vaccine induces antibodies recognizing the neutralizing, presumably conformational AIV epitope, specific to the H5 HA serotype; the titer of active antibodies in the FLUAc H5 test may reach the level observed during AIV infection in animals.

EXAMPLE 8 ANALYSIS OF IMMUNE RESPONSE WITH HEMAGGLUTINATION INHIBITION (HI) TESTS

Serum samples collected during the immunization experiments described in example 6 were analyzed for the presence of antibodies inhibiting hemagglutination (HI) by the H5 serotype AIV. Titers of HI antibodies in chicken sera were determined by hemagglutination inhibition tests with homologous HPAIV H5N1 and heterologous LPAIV H5N2 as antigens and the hemagglutination inhibition unit (HIU) of 1:8. The HI tests, commonly used in influenza virus infection diagnostics, provided functional evaluation of antibodies produced as a result of vaccination with rH5-*E. coli* and their potential capacity to protect against homologous and heterologous AIV infection. The principle of the HI test and its performance are described below.

Hemagglutinin—a protein found on the surface of influenza viruses—has the capacity to agglutinate erythrocytes.

This characteristic is the basis for identification of influenza virus isolates. The HI test utilizes the fact that specific binding of antibodies to antigenic sites on the HA molecule alters the capacity of this protein to bind erythrocyte surface receptors, thus preventing agglutination. The tests were conducted according to the current recommendations (Minta, 2008; Avian Influenza in: OIE Manual of Diagnostic Tests and Vaccines for Terrestrial Animals 2012).

HI Tests with AI Viruses

Two HI tests were performed using two H5 AI viruses and antisera described in line-up A.

| Line-up A Viruses and sera used in HI tests | | |
|---|---|---|
| HI-H5N1, HP | HI test with homologous HPAIV H5N1 | Origin |
| Antigen | HPAIV A

TABLE 5.2

| | HI AIV | | | | | | | |
|---|---|---|---|---|---|---|---|---|
| | After the 1st rH5 dose | | After the 2nd rH5 dose | | | | | |
| | 2 weeks | | 2 weeks | | 3 weeks | | 4 weeks | |
| ID | H5N1 HP | H5N2 LP | H5N1 HP | H5N2 LP | H5N1 HP | H5N2 LP | H5N1 HP | H5N2 LP |
| B-1 | <8 | <8 | 8 | <8 | <8 | <8 | <8 | <8 |
| B-2 | <8 | <8 | <8 | <8 | <8 | <8 | <8 | <8 |
| B-3 | 8 | <8 | 16 | <8 | 8 | <8 | 8 | <8 |
| B-4 | <8 | <8 | n.a. | <8 | 8 | <8 | <8 | <8 |
| B-5 | <8 | 8 | n.a. | <8 | <8 | <8 | <8 | <8 |
| B-6 | <8 | <8 | <8 | <8 | <8 | <8 | <8 | <8 |
| B-7 | <8 | <8 | 16 | <8 | 16 | 8 | 16 | <8 |
| B-8 | <8 | <8 | <8 | <8 | <8 | <8 | <8 | <8 |
| Seropositive | 1/8 (12.5%) | 1/8 (12.5%) | 3/6 (50%) | 0/8 (0%) | 3/8 (37.5%) | 1/8 (12.5%) | 2/8 (25%) | 0/8 (0%) |
| HI titer | 8 | 8 | 8-16 | <8 | 8-16 | 8 | 8-16 | <8 |

TABLE 5.3

| | HI AIV | | | | | | | |
|---|---|---|---|---|---|---|---|---|
| | After the 1st rH5 dose | | | | After the 2nd rH5 dose | | | |
| | 2 weeks | | 4 weeks | | 1 week | | 2 weeks | |
| ID | H5N1 HP | H5N2 LP | H5N1 HP | H5N2 LP | H5N1 HP | H5N2 LP | H5N1 HP | H5N2 LP |
| C-1 | 8 | <8 | 8 | 64 | <8 | 64 | 32 | 32 |
| C-2 | 8 | <8 | <8 | <8 | 32 | 32 | 64 | <8 |
| C-3 | <8 | <8 | <8 | <8 | <8 | <8 | <8 | 16 |
| C-4 | <8 | <8 | 8 | <8 | 8 | <8 | 8 | <8 |
| C-5 | <8 | <8 | <8 | 32 | 32 | <8 | 16 | 16 |
| C-6 | <8 | <8 | <8 | <8 | 8 | <8 | 8 | <8 |
| C-7 | <8 | <8 | <8 | 16 | <8 | <8 | <8 | <8 |
| C-8 | <8 | <8 | <8 | <8 | 8 | <8 | 8 | <8 |
| Seropositive | 2/8 (25%) | 0/8 (0%) | 2/8 (25%) | 3/8 (37.5%) | 5/8 (62.5%) | 2/8 (25%) | 6/8 (75%) | 3/8 (37.5%) |
| HI titer | <8 | <8 | 8 | 16-64 | 8-32 | 32-64 | 8-64 | 16-32 |

Summary

Analyses of humoral response in broiler-type Ross 308 chickens to subcutaneous administration of vaccine comprising 25 μg of rH5-*E. coli* and aluminium hydroxide as an adjuvant, conducted using the HI tests with homologous HPAIV H5N1 and heterologous LPAIV H5N2, demonstrated that:

- immunizations of chickens with rH5-*E. coli* repeated at an interval of 4 weeks are much more effective in inducing hemagglutination inhibiting antibodies than the immunizations at a 2-week interval,
- rH5-*E. coli* vaccination provides induction of antibodies inhibiting hemagglutination by AIV (HI-positive with H5N1 and/or H5N2/analyzed—8/8 chickens vaccinated twice at a 4-week interval),
- HI titer for antibodies induced by vaccination with rH5-*E. coli* reaches levels considered protective (≥1:16), also including a titer desired for the prevention of AIV infection (?1:64).

EXAMPLE 9 EFFECTIVENESS OF CHICKEN IMMUNIZATION WITH RH5-*E. COLI* AT DIFFERENT IMMUNIZATION SCHEDULES

In order to evaluate rH5-*E. coli* vaccine potency the results of analyses of sera prepared during immunization trials of broiler-type Ross 308 chickens, described in example 6, are summarized in the present example. Assays were performed using indirect and competitive ELISA to detect anti-H5 antibodies in chicken serum (H5-ELISA; FLUAc H5, IDVet). The HI tests were conducted using the following AI viruses as antigens: homologous HP H5N1 and heterologous LP H5N2 and the hemagglutination inhibition unit (HIU) of 1:8. The method of serological assays (ELISA, HI) and the results of these tests for chickens immunized with rH5-*E. coli* were described in detail in examples 7 and 8, with regard to the kinetics of humoral immune response and the individual nature of the response.

The analysis of immune response to vaccination in chickens, shown in the present example, includes results obtained from all blood collections in groups A, B and C (antibody detection, H5-ELISA), from blood collections after the administration of the 2nd rH5 dose to group B and C chickens (endpoint titer, H5-ELISA, FLUAc H5) or blood collected 2, 4 or 5 weeks after rH5 immunization of group B animals (FLUAc H5). The positivity of individual animals in the tests was evaluated here independently of the experimental stage at which it was assayed.

Efficacy of immunization of broiler-type chickens using rH5-*E. coli* is evaluated based on the statistics of animal response to the vaccination, the titer of IgY antibodies against H5, the titer of active antibodies in the FLUAc H5 test and the titer of HI antibodies. The titer of induced antibodies inhibiting erythrocyte agglutination by AIV should preferably be at least 1:16 (minimal protection level), it is optimal to reach 1:64 or higher. Assessment of the potential applicability of the tested vaccine to immunize birds against avian influenza, apart from the efficacy of vaccinations applying it, should also take into account the unit production cost of the vaccine and animal immunization costs. The number and size of antigen doses required to elicit immune response in animals and the type of adjuvant in the vaccine composition are significant components of these costs.

The results of analysis of broiler-type Ross 308 breed chicken humoral response to subcutaneous administration of one or two doses of vaccine comprising 25 μg of rH5-*E. coli* and aluminium hydroxide as an adjuvant, conducted using ELISAs (H5-ELISA, FLUAc H5) and HI tests (HI-H5N1, HI-H5N2) are summarized in Tab. 6. The data shown indicate that:

- two doses of the vaccine are required and sufficient to elicit a strong humoral response in all vaccinated chickens (H5-positive/analyzed—16/16),
- immunizations of chickens with rH5-*E. coli* repeated at a 4 week interval are much more effective in inducing anti-H5 IgY antibodies and active antibodies in the FLUAc H5 test as well as HI antibodies than immunizations at a 2 week interval, The results obtained for chickens vaccinated twice at an interval of 4 weeks using 25 μg-doses of rH5-*E. coli* with aluminium hydroxide (Tab. 6) demonstrated that in a specific number of animals within a group the vaccine induces, antibodies having the following properties:

- IgY specific towards H5 HA in all immunized chickens (H5-positive/analyzed—8/8); the endpoint titer for antigen-specific antibodies reaches high levels (1:129 200-1 week, 1:80 000-2 weeks after the 2nd rH5 dose),
- recognizing the presumably serotype-specific, neutralizing conformational AIV epitope; the titer for the antibodies competing with antibodies from the FLUAc H5 test may reach the levels observed during AIV infection in animals (FLUAc H5 positive/analyzed—3/8, FLUAc H5 doubtful/analyzed—2/8),
- inhibiting hemagglutination by homologous and heterologous AIV (HI-positive with H5N1/analyzed—6/8, HI-positive with H5N2/analyzed—5/8); the HI antibody titer reaching the levels considered as protective (≥1:16), also including the titer desired for prevention of AIV infection (≥1:64).

TABLE 6

| | CHICKEN GROUP | | |
|---|---|---|---|
| TEST TYPE | A | B | C |
| H5-ELISA | * | * | * |
| positive/analyzed | 8/8 | 8/8 | 8/8 |
| positivity [%] | 100% | 100% | 100% |
| End-point titer | — | 28 300 | 80 000 |
| 2 weeks after the 2nd rH5 dose | | | |
| FLUAc H5 | *** | ** | ** |
| competition < 90% | 3/8 | 8/8 | 7/8 |
| 35% < competition < 40% (±) | 0/8 | 0/8 | 2/8 |
| competition ≤ 35% (+) | 0/8 | 0/8 | 3/8 |
| positivity [%] | 0% | 0% | 37.5% |
| HI-H5N1 (HP) | * | * | * |
| HIU = 1:8 | | | |
| positive/analyzed | 1/8 | 4/8 | 6/8 |
| positivity [%] | 12.5% | 50% | 75% |
| HI titer | 8 | 8-16 | 8-64 |
| HI-H5N2 (LP) | * | * | * |
| HIU = 1:8 | | | |
| positive/analyzed | 0/8 | 2/8 | 5/8 |
| positivity [%] | 0% | 25% | 62.5% |
| HI titer | <8 | 8 | 16-64 |

* serum samples from all blood collections
** serum samples from blood collections after administration of 2nd rH5 dose
*** serum samples from blood collected 2, 4 or 5 weeks after immunization with rH5

Good results for immunization of broiler-type chickens with rH5-*E. coli* were obtained by administering only two doses of the antigen in the presence of aluminium hydroxide as an adjuvant. Aluminium hydroxide adjuvant has been commonly used for more than 80 years, primarily to enhance humoral immune response. Its activity enhancing cellular response is debatable. Efficacy of an inexpensive adjuvant, approved for animal and human immunization, such as aluminium hydroxide, in a vaccine composition with rH5-*E. coli* would result in the estimated unit cost of the vaccine not being excessively burdened by the price of its additional components. The efficacy of double vaccinations with rH5-*E. coli* in the presence of aluminium hydroxide has a positive effect on the costs of animal immunization using the tested vaccine.

Serological analyses of chickens vaccinated twice at a 4-week interval with 25 μg-doses of rH5-*E. coli* with aluminium hydroxide showed that all animals were responsive to the vaccination, as indicated by the high anti-H5 IgY antibody levels in animal sera (Tab. 6). The activity of the induced antibodies in tests evaluating their immunoprotective properties (FLUAc H5, HI-H5N1, HI-H5N2) varied within the vaccinated animal group (Tab. 6). Positivity in the group, reaching 37.5% in the FLUAc H5 test, 75% in the HI-H5N1 test and 62.5% in the HI-H5N2 test, demonstrates the vaccine potency in terms of the induction of desired functional antibodies and simultaneously indicates the necessity to optimize vaccinations such to increase the number of seropositive animals after vaccination in the aforementioned tests. Demonstration that two immunizations of broiler-type chickens at a 4-week interval are much more effective, if not exclusively effective, in inducing active antibodies in the FLUAc H5 test and in HI tests in comparison to two vaccinations at a 2-week interval (Tab. 6) shows the direction for optimization of animal vaccinations against avian influenza. Specification of the optimal time interval between the priming and booster doses seems to be crucial to increase efficacy of vaccinations of broiler-type chickens with the rH5-*E. coli* vaccine.

Immunizations of broiler-type chicken and vaccination response tests were performed during the period between day 7 of life, when the immunological system of birds is already mature and blood levels of maternal antibodies decrease, and the end of chicken production cycle (day 45 of life). This made it possible to examine immunogenicity of the rH5 (17-522 aa, ΔRRRKKR (SEQ ID NO: 2)) fragment produced by overexpression in *E. coli* (rH5-*E. coli*) and to test the efficacy of various immunization regimens. Short life-cycle of broiler-type chickens in commercial rearing systems considerably limits the potential for optimization of vaccinations; moreover, there is no economic justification for the use of the tested vaccine for mass vaccinations in this animal group. Studies on the optimization of rH5-*E. coli* dosage and vaccination regimen will target chicken groups with long life-cycles, such as laying hens in commercial flocks and breeding flocks of hens and broilers.

The final criteria in assessment of efficacy of rH5-*E. coli* vaccination are provided by the results of experimental infection of chickens with AI viruses. The challenge experiment was performed in laying-type SPF chickens. Chickens vaccinated with rH5-*E. coli* were infected with HPAIV H5N1. The method of the experiment and its results are described in example 10.

EXAMPLE 10 EXPERIMENTAL INFECTION OF CHICKENS VACCINATED WITH RH5-*E. COLI* WITH HIGHLY PATHOGENIC (HP) AVIAN INFLUENZA VIRUSES (AIV) H5N1 (CHALLENGE)

In order to evaluate the capacity of rH5-*E. coli* vaccine to provide protection against AIV infection, an experimental infection of vaccinated chickens was performed using the following HPIV H5N1 viruses: homologous from clade 2.2 (experiment 1) and heterologous from clade 1 (experiment 2). The challenge experiments were conducted in laying-type SPF White Leghorn chickens, at the National Veterinary Research Institute (NVRI) in Pulawy, in PCL3 containment.

Immunization with rH5-*E. coli*, Infection with HPAIV H5N1 and Sample Collection for Analyses A group of 3-week old (experiment 1) or 3½-week old (experiment 2) SPF chickens (10 animals) were vaccinated subcutaneously by administering 25 µg of rH5-*E. coli* in the volume of 200 µl with aluminium hydroxide as an adjuvant. The vaccine composition was prepared as described in example 6. The booster dose—25 µg of rH5-*E. coli* with aluminium hydroxide, was administered 4 (experiment 1) or 4½ (experiment 2) weeks later. Two and four weeks after the administration of the $1^{st}$ dose and two and three weeks after administration of the 2nd antigen dose, blood was collected for serological analyses.

Three weeks after the second immunization the chickens were infected with homologous HPAIV—A/turkey/Poland/35/07(H5N1) from clade 2.2 (experiment 1) or heterologous HPAIV-A/crested eagle/Belgium/01/2004(H5N1) from clade 1 (experiment 2). The viral infection titer was $10^9$ $EID_{50}$/ml. Viruses were administered intranasally and conjunctivally (i.n./i.o.) at the dose of $10^6$ $EID_{50}$ in 0.1 ml (1:100 dilution). To analyze the potential of AI virus transmission from chickens infected after vaccination to fully susceptible birds, approx. 24 hours after HPAIV infection, 2 non-vaccinated SPF chickens (contact animals) were introduced to each experimental group. During 14 days after infection clinical observations of the animals were conducted. Three, seven and ten days after infection, throat and cloacal swabs for real time RT-qPCR analyses were collected from vaccinated and contact chickens. Fourteen days after infection, blood samples for serological analyses were collected from all challenge surviving birds, as well as throat and cloacal swabs for real time RT-qPCR analyses.

The positive control for the challenge experiments comprised SPF chickens, 5 in each group, that at the same age as the experimental group chickens were infected with A/turkey/Poland/35/07(H5N1) from clade 2.2 (experiment 1) or with A/crested eagle/Belgium/01/2004(H5N1) from clade 1 (experiment 2), applying identical doses and administration method as for vaccinated animals, i.e. i.n./i.o., dose of $10^6$ $EID_{50}$ in 0.1 ml (1:100 dilution). Throat and cloacal swabs as well as body organs (lungs, spleen, kidneys, brain) were collected for real time RT-qPCR from the chickens that died during the observation period.

The experiments were conducted according to the requirements for vaccine testing in challenge experiments, e.g. regarding the dose ($10^6$ $EID_{50}$) and the interval between vaccination and experimental infection (3 weeks), as described in "The Manual of Diagnostic Tests and Vaccines for Terrestrial Animals, 2012" OIE.

The course of immunization, infection and sample collection for analyses in experiments 1 and 2 were applied according to regimens B (FIG. 32) and C (FIG. 33), respectively.

Serological Analyses

Serum samples collected during the experiment were analyzed using the hemagglutination inhibition (HI) tests and commercial ELISA tests: FLUAc H5 (IDVet) and IDEXX AI MultiS-Screen (Idexx Laboratories). The results of the HI tests with H5 viruses and the FLUAc H5 test to detect antibodies against AIV H5 made it possible to evaluate humoral response of chickens to rH5-*E. coli* vaccination and serum functional antibody levels in vaccinated animals directly before the HPAIV H5N1 infection. The IDEXX AI MultiS-Screen (Idexx Laboratories) is designed to detect anti-AIV antibodies in bird sera. The application of this test on the samples collected during the challenge experiments was to monitor exposure of chickens to AI viruses. Serological analyses of samples collected after HPAIV infection from vaccinated and contact chickens with the IDEXX AI MultiS-Screen test were complementary in relation to the analyses of viral genetic material levels in swabs that were performed using real time RT-qPCR.

The HI activity of chicken sera collected during the challenge experiments was tested using inactivated HPAIV H5N1: homologous and heterologous. Viruses and antisera used in the HI tests are described in line-up B.

| Line-up B Viruses and sera used in HI tests | | |
|---|---|---|
| HI-H5N1/homologous - HI test with homologous HPAIV H5N1 | | Origin |
| Antigen | HPAIV A/turkey/Poland/35/07 (H5N1) | DPD NVRI |
| Positive control | Anti- HPAIV serum against the A/turkey/Poland/35/07 (H5N1) | DPD NVRI |
| Negative control | SPF chicken serum | AHLA |
| HI-H5N1/heterologous - HI test with heterologous HPAIV H5N1 | | Origin |
| Antigen | HPAIV A/CK/Scot/59 (H5N1) | AHLA |
| Positive control | Anti- HPAIV serum against the A/CK/Scot/59 (H5N1) | AHLA |
| Negative control | SPF chicken serum | AHLA |

DPD NVRI Department of Poultry Diseases, the National Veterinary Research Institute, Pulawy, Poland
AHLA Animal Health and Veterinary Laboratories Agency, Waybridge, UK The HI test was conducted with SPF chicken erythrocytes using the hemagglutination inhibition unit (HIU) of 1:8. The tests were performed as described in example 8. Serum HI titers ≥1:16 were considered as indicative of the protective activity of induced antibodies, according to the currently binding requirements for influenza vaccines.

The FLUAc H5 test was performed according to the manufacturer's (IDVet) instructions, however, conditions enhancing test sensitivity were not applied. According to the basic protocol, serum samples were diluted 1:5 and then incubated on plates for 1 hour at 37° C. The method to calculate competition levels and interpretation of the results, according to the manufacturer's data, are described in example 7. The IDEXX AI MultiS-Screen test was conducted according to the manufacturer's (Idexx Laboratories) instructions. Interpretation of results in this test depends on the value of absorption reading for the analyzed sample (S) in relation to the value read for the negative control (N). Calculated values S/N≥0.5 and <0.5 obtained for the analyzed samples indicate that the samples are negative and positive, respectively, with respect to anti-AIV antibodies.

Determination of AIV Levels after Infection

The aim of real time RT-qPCR analyses was to detect viral genetic material in throat and cloacal swabs and in the case of dead animals also in their organs (lungs, spleen, kidneys, brain). Results of these analyses made it possible to determine the degree of AIV propagation and multiplication in the infected birds and the probability of virus shedding to the environment and its transmission to other birds.

Samples collected for analyses with real time RT-qPCR were stored in a universal transport medium (COPAN Diagnostics Inc.). Total RNA was extracted from 0.1 ml medium using the RNeasy Mini Kit (Qiagen). Real time mRT-PCR was performed as described by Spackman E et al. (2002). The following oligonucleotides: M-25 (5'-AGATGAGTCT-TCTAACCGAGGTCG-3') SEQ ID NO: 10 and M-124 (5'-TGCAAAAACATCTTCAAGTCTCT-3') SEQ ID NO: 11 were used as primers, while the probe was M-64 (5'-FAMTCAGGCCCCCTC AAAGCCGA-TAMRA-3') SEQ ID NO: 12. Qualitative RNA standards with known virus titers, extracted from 10-fold dilutions of viruses used in experimental infection of chickens were used to convert the Ct value of RT-qPCR to values equivalent to $EID_{50}$ ($eqEID_{50}$) per ml of swab fluid or per gram of tissue. The amounts of viral RNA in the tested samples were extrapolated from the standard curve.

Functional Anti-H5 Antibody Levels Before Infection

The results of serological analyses of laying-type SPF chickens after subcutaneous administration of two rH5-*E. coli* doses, 25 μg each, with aluminium hydroxide as an adjuvant, conducted on samples collected 3 weeks after administration of the 2nd dose of antigen using the HI tests are shown in FIG. 19, whereas those for the FLUAc H5 (IDVet) test are given in FIG. 20. Directly before infection with the homologous (experiment 1) or heterologous (experiment 2) HPAIV H5N1, no animal from the group vaccinated with rH5-*E. coli* in either experiment exhibited a protective titer, i.e. ≥1:16, for antibodies inhibiting hemagglutination by heterologous HPAIV H5N1 (FIG. 19). The protective antibody titer in HI tests with homologous HPAIV H5N1 was detected within the range of 1:16-1:128 in 5 out of 10 chickens vaccinated in the first experiment and at 1:16-1:256 in all studied chickens (9/9) vaccinated in the second challenge experiment.

Chickens denoted 2-2 . . . 2-10 responded more strongly to rH5-*E. coli* vaccination with production of HI antibodies active against homologous HPAIV H5N1 than chickens denoted 1-1 . . . 1-10, as indicated by the number of seropositive chickens in the group (100% vs. 50%) and the HI antibody titers (mean 65.8 vs 26.4). In the FLUAc H5 test, seropositivity of chickens 2-2 . . . 2-10 vaccinated before infection with heterologous HPAIV H5N1, was 56% and it was lower than that for chickens 1-1 . . . 1-10 from the group vaccinated in the challenge experiment with homologous HPAIB H5N1, in which 100% animals were seropositive (FIG. 20). The serum competition levels in the FLUAc H5 test for seronegative chickens denoted 27 . . . 2-10 varied greatly, ranging from 51 to 96%.

Influenza Morbidity and Infection Survival Rate

The results of experimental infection of vaccinated and control laying-type SPF chickens with the following HPAI H5N1 viruses: a clade 2.2 homologous one (experiment 1) and a clade 1 heterologous one (experiment 2), expressed as % survival rate of infected and contact animals during 14 days after infection are shown in FIGS. 21A-21B. Chickens vaccinated with rH5-*E. coli* and then infected with homologous HPAIV H5N1, as well as contact chickens were alive and did not exhibit clinical influenza symptoms during the whole observation period (FIG. 21A). Control group animals, which had not been vaccinated, died 2 days (2 chickens) or 3 days (3 chickens) after infection.

In the experiment with heterologous HPAIV H5N1 from clade 1, 3 out of 10 vaccinated chickens died—one animal on the second and two others on the third day after infection (FIG. 21B). Among the 7 chickens surviving the challenge, 4 were found to exhibit no disease symptoms and 3 contracted influenza. An animal denoted 2-6 exhibited symptoms of influenza between days 4 and 11 after infection: infraorbital sinus swelling, evident weakening, squatting, blueness and edema of the comb. Two chickens, denoted 2-3 and 2-5, were ill from the 5th day after infection with less severity than animal 2-6—infraorbital sinus swelling and weakening were observed. Chickens 2-3, 2-5 and 2-6 recovered and did not show any disease symptoms at day 14 after infection. Contact chickens were alive until day 7 after infection of vaccinated animals. Between days 7 and 8 after infection one contact chicken died and on day 8 after infection another contact animal died. Control group chickens that had not been vaccinated died 2 days after infection.

Anti-H5 Antibodies and Immunity Against Infection

The results of the FLUAc H5 test and the HI test with homologous HPAIV H5N1 recorded for chickens directly before infection with homologous HPAIV H5N1 (FIG. 19, FIG. 20) demonstrate that chicken immunity against infection with the homologous HPAI virus was probably associated primarily with the high level of active antibodies in the FLUAc H5 (IDVet) test and in 5 out of 10 chickens possibly also with the presence of antibodies inhibiting hemagglutination by homologous HPAIV H5N1.

The results of the FLUAc H5 test and the HI test with heterologous HPAIV H5N1 obtained for chickens directly before infection with heterologous HPAIV H5N1 (FIG. 19, FIG. 20) demonstrate that immunity against infection in 7 out of 10 vaccinated chickens is not a result of inducing HI antibodies. All chickens seropositive in the FLUAc H5 test survived the infection with heterologous HPAIV H5N1, and only one animal, denoted 2-7, from among the 4 seronegative animals, whose serum was found to have the lowest competition value in the test (FIG. 20). This suggests that chicken immunity against infection with heterologous HPAIV was associated with a high titer of antibodies competing with the FLUAc H5 test antibodies, presumably for a serotype-specific neutralizing epitope of AIV H5.

Anti-AIV Antibody Levels

The results of serological analyses of laying-type SPF chickens, conducted using the IDEXX AI MultiS-Screen test (Idexx Laboratories) on samples collected 3 weeks after administration of the 2nd dose of rH5-*E. coli* and 2 weeks after experimental infection with homologous (experiment 1) and heterologous (experiment 2) HPAIV H5N1 and in parallel from contact chickens are shown in Tab. 7. Directly before infection with HPAI viruses, all studied chickens from the rH5-*E. coli* vaccinated and contact groups were seronegative. Two weeks after infection with homologous HPAIV H5N1 all vaccinated chickens and 1 out of 2 in-contact animals, denoted 1-KK-2, produced antibodies against AIV. Among the 7 chickens that survived infection with heterologous HPAIV H5N1, 4 were seropositive, while 3 others remained seronegative in the IDEXX AI MultiS-Screen test. Among the 3 chickens, 2-3, 2-5 and 2-6, showing symptoms of influenza after infection with heterologous HPAIV H5N1 animals 2-5 and 2-6, in contrast to animal 2-3, produced antibodies detectable by the test.

TABLE 7

| | Experiment 1 with homologous HPAIV H5N1 (clade 2.2) | | | Experiment 2 with heterologous HPAIV H5N1 (clade1) | |
|---|---|---|---|---|---|
| | IDEXX AI MultiS-Screen | | | IDEXX AI MultiS-Screen | |
| ID | Before infection result | 2 weeks after infection result | ID | Before infection result | 2 weeks after infection result |
| 1-1 | − | + | 2-1 | n.d. | − |
| 1-2 | − | + | 2-2 | − | − |
| 1-3 | − | + | 2-3* | − | − |
| 1-4 | − | + | 2-4 | − | + |
| 1-5 | − | + | 2-5* | − | + |
| 1-6 | − | + | 2-6** | − | + |
| 1-7 | − | + | 2-7 | − | + |
| 1-8 | − | + | 2-8$^a$ | − | n.a. |
| 1-9 | − | + | 2-9$^a$ | − | n.a. |
| 1-10 | − | + | 2-10$^b$ | − | n.a. |
| Vaccinated seropositive | 0/10 | 10/10 | Vaccinated seropositive | 0/9 | 4/7 |
| 1-KK-1 | − | − | 2-KK-1$^c$ | − | n.a. |
| 1-KK-2 | − | + | 2-KK-2$^d$ | n.a. | n.a. |
| Contact seropositive | 0/2 | 1/2 | Contact seropositive | 0/1 | n.a. | n.a.—not available
Chickens with transient symptoms of influenza:
*, **more severe disease symptoms
Chickens dying:
$^a$3 dpi,
$^b$2 dpi,
$^c$8 dpi,
$^d$7-8 dpi The obtained results confirmed that chickens selected for challenge experiments did not have contact with AIV before the experimental infection and immunity against the infection was induced exclusively by rH5-*E. coli* vaccination. Among the 17 vaccinated chickens that survived infection with HPAI viruses, a majority, i.e. 82%, of animals produced antibodies against AIV, detected with the IDEXX AI MultiS-Screen test. Assays of anti-AIV antibody levels in contact chickens that were introduced to the group infected with homologous HPAIV H5N1 after vaccination, demonstrate that only one of the two fully susceptible animals had contact with AIV originating from the infected animals.

Amount of HPAIV RNA in Swabs after Infection

The results of viral RNA level analysis in throat (T) and cloacal (C) swabs collected from chickens vaccinated with rH5-*E. coli* and from contact chickens after infection with the HPAI H5N1 viruses—3, 7, 10 and 14 days post infection (dpi) or post mortem, are shown in Tab. 8. In the group of vaccinated chickens infected with the homologous HPAIV H5N1, genetic material of the virus was detected in 8 out of 10 chickens 3 dpi and only in throat swabs, wherein levels thereof reached values in the range of 2.4-3.8 $\log_{10}$ EID$_{50}$/ml. In the next days after infection, i.e. 7 and 10 dpi, viral RNA was not detected in swabs from this animal group. Seven days post infection of the vaccinated animals, viral RNA was found in throat swab from 1 out of 2 contact chickens (1-KK-2) but was no longer detected on 10 dpi.

TABLE 8

Viral RNA levels in throat (T) and cloacal (C) swabs after HPAIV infection [$\log_{10}$ EID$_{50}$/ml]

| | Days post infection (dpi) with the homologous HPAIV H5N1 from clade 2.2 (experiment 1) | | | | | | | |
|---|---|---|---|---|---|---|---|---|
| | 3 | | 7 | | 10 | | 14 | |
| ID | T | C | T | C | T | C | T | C |
| 1-1 | U | U | U | U | U | U | n.a. | n.a. |
| 1-2 | U | U | U | U | U | U | n.a. | n.a. |
| 1-3 | 3.4 | U | U | U | U | U | n.a. | n.a. |
| 1-4 | 2.7 | U | U | U | U | U | n.a. | n.a. |
| 1-5 | 3.8 | U | U | U | U | U | n.a. | n.a. |
| 1-6 | 2.8 | U | U | U | U | U | n.a. | n.a. |
| 1-7 | 3.5 | U | U | U | U | U | n.a. | n.a. |
| 1-8 | 2.4 | U | U | U | U | U | n.a. | n.a. |
| 1-9 | 3.8 | U | U | U | U | U | n.a. | n.a. |
| 1-10 | 3.3 | U | U | U | U | U | n.a. | n.a. |
| Vaccinated positive | 8/10 | 0/10 | 0/10 | 0/10 | 0/10 | 0/10 | — | — |
| 1-KK-1 | U | U | U | U | U | U | n.a. | n.a. |
| 1-KK-2 | U | U | 4.9 | U | U | U | n.a. | n.a. |
| Contact positive | 0/2 | 0/2 | 1/2 | 0/2 | 0/2 | 0/2 | — | — |

| | Days post infection (dpi) with the heterologous HPAIV H5N1 from clade 1 (experiment 2) | | | | | | | |
|---|---|---|---|---|---|---|---|---|
| | 3 $2^b$ or $3^a$ pm | | 7 | | 10 $8^{c,d}$ pm | | 14 | |
| ID | T | C | T | C | T | C | T | C |
| 2-1 | U | U | U | U | U | U | U | U |
| 2-2 | U | U | U | U | U | U | U | U |
| 2-3* | U | U | U | U | U | U | U | U |
| 2-4 | U | U | U | U | U | U | U | U |
| 2-5* | U | U | U | U | U | U | U | U |
| 2-6** | 4.9 | U | 4.6 | U | U | U | U | U |

TABLE 8-continued

Viral RNA levels in throat (T) and cloacal (C) swabs after HPAIV infection [$\log_{10}$ EID$_{50}$/ml]

| | | | | | | | | | |
|---|---|---|---|---|---|---|---|---|---|
| 2-7 | 3.8 | U | 6.2 | 7.1 | U | 6.0 | U | U | |
| 2-8$^a$ | 7.0 | U | — | — | — | — | — | — | |
| 2-9$^a$ | 6.7 | 6.7 | — | — | — | — | — | — | |
| 2-10$^b$ | 8.3 | 7.2 | — | — | — | — | — | — | |
| Vaccinated positive | 5/10 | 2/10 | 2/7 | 1/7 | 0/7 | 1/7 | 0/7 | 0/7 | |
| 2-KK-1$^c$ | U | U | 5.4 | 5.3 | 6.8 | 7.2 | — | — | |
| 2-KK-2$^d$ | U | U | 4.9 | 5.0 | 7.0 | 7.7 | — | — | |
| Contact positive | 0/2 | 0/2 | 2/2 | 2/2 | 2/2 | 2/2 | — | — | |

EID$_{50}$—50% Egg Infectious Dose
U—no AIV genetic material detected
n.a.—not determined
Chickens with transient symptoms of influenza:
*, **more severe disease symptoms
Chickens dying:
$^a$3 dpi.
$^b$2 dpi.
$^c$8 dpi.
$^d$7-8 dpi - swabs collected post mortem (pm)

In the group of chickens vaccinated with rH5-*E. coli* and then infected using the heterologous HPAIV H5N1, genetic material of the virus was not detected in throat and cloacal swabs of 5 out of 10 vaccinated animals in none of the assays performed on samples collected in the 2-week observation period. Analysis of samples collected post mortem from 3 chickens-denoted 2-8, 2-9 and 2-10 that died 2 or 3 dpi, demonstrated the presence of substantial amounts of viral RNA in the range of 6.7-8.3 $\log_{10}$ EID$_{50}$/ml in throat or throat and cloacal swabs. Among the chickens that survived infection with the heterologous HPAIV, viral genetic material was detected in 2 animals. For the 2-6 denoted animal viral genetic material was detected at the level of 4.9 and 4.6 $\log_{10}$ EID50/ml in throat swabs collected 3 and 7 dpi and for the 2-7 denoted animal in throat, in throat and cloacal and in cloacal swabs, on 3, 7 and 10 dpi respectively at the level in the range of 3.8-7.1 $\log_{10}$ EID$_{50}$/ml. The results of virus level analysis in swabs collected from the 2-7 animal additionally confirm the hypothesis of the crucial role of antibodies active in the FLUAc H5 test in the immunity against infection, described in the 'Anti-H5 antibodies and immunity against infection' chapter. Two weeks after infection, viral RNA was not detected in swabs collected from all animals that survived the challenge (7/10). Among the 3 chickens: 2-3, 2-5 and 2-6 showing symptoms of influenza after infection with the heterologous HPAIV H5N1, viral presence in swabs was found only for the animal with more severe disease symptoms, denoted 2-6. In the 2 other chickens: 2-3 and 2-5 no viral RNA was found in samples collected from throat and cloaca, which may indicate a systemic nature of the infection. In the contact chickens no viral genetic material was detected on 3 dpi, however on 7 dpi viral RNA was found in the range of 5.0-5.4 $\log_{10}$ EID50/ml in both throat and cloacal swabs, suggesting replication of AI viruses deriving from vaccinated chickens with detectable levels of viral particles. Analysis of samples collected post mortem from contact chickens on 8 dpi demonstrated an even greater amounts of viral RNA in swabs, wherein levels thereof reached values in the range of 6.8-7.7 $\log_{10}$ EID$_{50}$/ml.

The results of the first challenge experiment unambiguously demonstrated that rH5-*E. coli* vaccination induces immune response in chickens, preventing multiplication of homologous HPAIV H5N1. Furthermore, the vaccination limited shedding of HPAI viruses to a few days after infection at most, maximally to 7 dpi, and eliminated effective HPAIV transmission to fully susceptible contact chickens. The results of the second challenge experiment demonstrated that rH5-*E. coli* vaccination induces immune response in 7 out of 10 chickens, preventing (5 chickens) or limiting to a large extent (2 chickens) multiplication of heterologous HPAIV H5N1. Moreover, vaccination decreased by 70% the number of chickens excreting the heterologous AIV during a period longer than 10-14 dpi and in that sense caused a decrease in shedding of HPAI viruses as well as delayed effective HPAIV transmission to fully susceptible contact animals, but did not prevent it.

Summary

The results of challenge experiments, wherein laying-type SPF chickens (White Leghorn) were vaccinated twice at an interval of 4 or 4½ weeks, using 25 µg-doses or rH5-*E. coli* (17-522 aa, ΔRRRKKR (SEQ ID NO: 2) with aluminium hydroxide and next infected with HPAIV H5N1: a homologous one from clade 2.2 or a heterologous one from clade 1, demonstrated that:

rH5-*E. coli* immunization provides 100% protection of chickens against infection with the homologous HPAIV H5N1;—shedding of animals infected after vaccination was minimized; no transmission of HPAI viruses to fully susceptible contact animals occurred, rH5-*E. coli* vaccination protects 70% of chickens against infection with the heterologous HPAIV H5N1; shedding of animals infected after vaccination was limited; AIV levels in chickens infected after vaccination was sufficient for effective transmission of HPAI viruses to contact chickens but animal deaths did not occur before between the 7$^{th}$ and 8$^{th}$ or on the 8$^{th}$ day after infection of vaccinated chickens, chicken immunity against HPAIV H5N1 infection is associated with the level of antibodies active in the FLUAc H5 test (IDVet).

At the present study stage, the vaccine containing rH5-*E. coli* was shown to be effective increasing immunity against infection, decreasing morbidity and mortality at infection with different variants of viruses from the same serotype and limiting HPAI viruses virus shedding to environment.

EXAMPLE 11 OPTIMIZATION OF VACCINATION REGIMEN WITH RH5-*E. COLI*

In order to determine the optimal rH5-*E. coli* dose and the interval between the doses that is advantageous for immunization effectiveness, immunization studies were performed on laying-type chickens, using antigen doses in range of 5-25 µg and 4- and 6-week interval between the I and the II immunization.

Chicken Immunization and Sample Collection for Serological Studies

The vaccine containing rH5-*E. coli* and aluminium hydroxide as an adjuvant was prepared directly before use, as described in example 6. Experiments were performed simultaneously in 8 groups of laying-type Rossa 1 breed chickens under production rearing conditions. Chickens from groups 1A-4A, 1B-4B, 10 animals each, were vaccinated, whereas 15 non-immunized chickens formed control group K. First immunization was done in the 3$^{rd}$ week of life of the animals. Chickens from groups 1A-4A were immunized for the second time in the 7$^{th}$ week of life, i.e. 4 weeks after administering the I dose, while groups 1B-4B in the 9$^{th}$ week of life, i.e. 6 weeks after administering the I dose. rH5-*E. coli* was used for animal immunization at doses of 25, 15, 10 and 5 µg, administered subcutaneously in three areas on the back of the neck in volume of 200 µl with aluminium hydroxide as an adjuvant.

In order to monitor chicken response to immunization, blood was collected from vaccinated animals directly before and 1 and 2 weeks after administering the II antigen dose. Samples collected in parallel from non-vaccinated chickens were the control material. Serum samples were prepared and stored as described in example 6. Schedule of chicken immunizations and blood collection from vaccinated and control animals was according to regimen D (FIG. 34).
Immune Response Analysis with Serological Assays Sera prepared during the experiment were analyzed using ELISAs: indirect—H5-ELISA and competitive—FLUAc H5 (IDVet) for detection of antibodies against AIV H5 HA and the hemagglutination inhibition (HI) test. The test detecting antibodies recognizing the presumably serotype-specific neutralizing conformational epitope of AIV (FLUAc H5) and the HI test, detecting antibodies recognizing HA antigenic sites in viral particles which are essential for binding to cellular receptors, enabled a functional analysis of the antisera produced as a result of vaccination.

The H5-ELISA was done according to the description in example 7. The FLUAc H5 test was conducted according to the manufacturer's (IDVet) instructions, applying the conditions increasing the test sensitivity (serum samples diluted 1:1, incubated on plates for 1 hour at temperature of 37° C.). The method of calculating competition levels and of interpretation of the results, according to the manufacturer's data, is described in example 7. The HI test was conducted with SPF chicken erythrocytes, using the heterologous LPAIV H5N2 as an antigen and hemagglutination inhibition unit (HIU) of 1:8. The principle of the HI test and the method of conducting it are shown in example 8. Assays were done on serum samples from all blood collections. Samples were considered positive if they reached the titer of ≥1:8. It was considered that, according to the requirements for influenza vaccines currently in force, the HI titer indicating a protective effect of the induced antibodies should be ≥1:16.

Results of Serological Studies

Serological studies of laying-type chickens after subcutaneous priming immunization using 25 μg (groups: 1A, 1B), 15 μg (groups: 2A, 2B), 10 μg (groups: 3A, 3B) or 5 μg (groups: 4A, 4B) of rH5-*E. coli* and aluminium hydroxide as an adjuvant, performed with the H5-ELISA on samples collected 4 weeks (groups: 1A-4A) or 6 weeks (groups: 1B-4B) after vaccination, demonstrated detectable IgY antibodies against H5 in the sera, diluted 1:200, at the level in range of 60%-100% and 0%-33%, respectively (FIG. 22). One and two weeks after administering the antigen booster dose, high anti-H5 antibody levels in all vaccinated chickens were found indicating 100% seropositivity. Endpoint titer for serum anti-H5 IgY antibodies in all animal groups after two immunizations was very high—1 week and 2 weeks after administering the II antigen dose it reached values in range of: 320 000-850 000 and 200 000-430 000, respectively (FIG. 23).

Changes in anti-H5 IgY antibody levels after second immunization were accompanied by changes in levels of functional antibodies, detected with the FLUAc H5 (IDVet) and HI test with the heterologous LPAIV H5N2. Directly before administering the II antigen dose, no positive samples were found in the FLUAc H5 test (FIG. 24). The HI-H5N2 test demonstrated that only 11% of animals vaccinated with one antigen dose, in 2 out of 8 studied groups, had protective HI antibody titer (≥1:16) in serum (FIG. 25). One week after second immunization, positivity in the FLUAc H5 test in groups vaccinated with rH5-*E. coli* at doses of 10, 15 and 25 μg reached values in range of 70-100%, while in groups vaccinated with 5 μs of antigen it was 50 and 60% (FIG. 24). At the same time, chickens having protective HI antibody titer constituted 80-100% of the chickens vaccinated twice using 5-25 μs rH5-*E. coli* (FIG. 25). The high positivity level in chickens in the HI and FLUAc H5 tests was retained during the observation period, that is up to the $2^{nd}$ week after vaccination (FIG. 24, 25).

In Tab. 9 the results of chicken positivity assays during 2 weeks after vaccinations are summarized, the results being obtained using the FLUAc H5 and the HI-H5N2 tests. Positivity in the FLUAc H5 test in groups vaccinated with rH5-*E. coli* at doses of 10, 15 and 25 μg reached values in range of 68-90%, in the group vaccinated with 5 μg of antigen it was 52.5%±10, whereas the percentage of chickens vaccinated twice using 5-25 μg of rH5-*E. coli* showing protective HI antibody titer was in range of 81-87%.

TABLE 9

| Group | Interval between doses [weeks] | Dose [μg] | FLUAc H5 (IDVet) positive after the II dose mean (n=4) | HI - H5N2 LPAIV HI ≥ 1:16 after the II dose mean (n = 4) |
|---|---|---|---|---|
| 1A | 4 | 25 | 90% ± 8 | 87% ± 12.5 |
| 1B | 6 | | | |
| 2A | 4 | 15 | 68% ± 4 | 85% ± 19 |
| 2B | 6 | | | |
| 3A | 4 | 10 | 85% ± 6 | 87% ± 12.5 |
| 3B | 6 | | | |
| 4A | 4 | 5 | 52.5% ± 10 | 81% ± 15 |
| 4B | 6 | | | |
| 2 × 5-25 μg rH5-*E. coli* interval of 4 or 6 weeks mean (n = 16) | | | 74% ± 16.5 | 85% ± 14 |

The results of analyses of sera collected 1 and 2 weeks after administering two doses of rH5-*E. coli*, 5, 10, 15 or 25 μg each, shown in FIG. 26 and FIG. 27 as the serum HI antibody titer levels for individual animals and as a mean HI titer value in each studied group, demonstrate that a large portion of the animals exhibited not only the minimal protective HI antibody titer (≥1:16) but also a titer desired for preventing AIV infection (≥1:64). Among the chickens analyzed after administering the II antigen dose in the range of 5-25 μg, 50% were the animals exhibiting titer of the 1:64 level or higher in sera collected 1 and/or 2 weeks after second immunization, reaching the value of 1:512 in 3 chickens.

Summary

Analyses of laying-type Rossa 1 breed chicken humoral response to subcutaneous administration, at an interval of 4 or 6 weeks, of two vaccine doses comprising 5-25 μg of rH5-*E. coli* and aluminium hydroxide as an adjuvant, conducted on 8 chicken groups of 10 animals each, using ELISAs (H5-ELISA; FLUAc H5, IDVet) and the HI test with the heterologous LPAIV H5N2, demonstrated that:

- recombinant H5 HA (17-522 aa, ΔRRRKKR (SEQ ID NO: 2)) from a bacterial expression system—rH5-*E. coli* is strongly immunogenic,
- two vaccine doses, administered at a 4- or 6-week interval are essential, but also sufficient to elicit a strong humoral response in all vaccinated chickens (H5-positive—100%); the endpoint titer of antigen-specific antibodies reaches high values (200 000-850 000—within 2 weeks after the II rH5 dose),
- two immunizations of chickens with rH5-*E. coli* at doses of 5-25 μg with aluminium hydroxide as an adjuvant, at an interval of 4 or 6 weeks, induce in most animals functional anti-H5 antibodies:
- active in the FLUAc H5 test (IDVet) at the level observed during infection with AI viruses of the H5 serotype (FLUAc H5-positive—74%±16.5% of chickens), inhibiting hemagglutination by LPAIV H5N2 at a level considered as protective (with HI titer ≥1:16-85%±14% of chickens) and also at a level desired for preventing an AIV infection (with HI titer ≥1:64-50% of chickens).

Immunization studies of laying-type Rossa 1 breed chickens, wherein the animals were administered twice at a 4 week interval with 25 μg of rH5-*E. coli* and aluminium hydroxide as an adjuvant, described in example 11, demonstrated a much higher vaccination effectiveness than the immunization studies conducted using an identical antigen dose, adjuvant and interval between the doses in broiler-type Ross 308 breed chickens, described in examples: 6-9. Immunization regimens differed only in that the immunization of laying-type chickens was started in the third week of life, whereas that of broiler-type chickens out of necessity in the first week. However, the difference in humoral response to the vaccination for laying-type and broiler-type chickens, primarily concerning the presence and levels of functional anti-H5 antibodies (FIG. 28), was rather an effect of different immunoreactivity in both animal groups than of the age difference in immunized animals. Lower immunoreactivity of broiler-type chickens than laying-type chickens was shown by Koenen M E et al. in studies, wherein both animal types were at the same age immunized using a model TNP-KLH antigen (Koenen M E et al. 2002). The observed differences in response to vaccination of broiler-type and laying-type chickens are probably associated with different metabolism, lifespan and body mass of the animals.

EXAMPLE 12 ENHANCING IMMUNE RESPONSE BY INTRANASAL ADMINISTRATION OF RH5-*E. COLI*

In order to investigate the potential of rH5-*E. coli* to induce immune response in birds by mucosa, a vaccine composition was developed comprising rH5-*E. coli* and a mucoadhesive adjuvant (chitosan glutamate) for mucosal immunization and an immunization study was conducted on laying-type chickens, wherein the parenterally primed animals were given an intranasal booster dose.

Vaccine Preparation, Chicken Immunization and Sample Collection for Serological Studies Protein and hemagglutinin content in the rH5-*E. coli* preparations for production of vaccines, were determined according to the description in example 6. The vaccine for parenteral immunization, comprising rH5-*E. coli* and aluminium hydroxide as an adjuvant, was prepared directly before use as described in example 6. For the preparation of the intranasal vaccine with rH5-*E. coli*, PROTASAN™ UP G 113 (NovaMatrix/FMC Corp.) was used, being a highly purified chitosan glutamate—a bioadhesive polymer with <20 mPa·s viscosity, molecular mass of <200 kDa and deacetylation level of 75-90%. PROTASAN was dissolved in deionized water by intense shaking on a vortex mixer, and next a 10× concentrated PBS solution, pH=7.4 was added in volume ensuring buffer dilution and it was shaken on a vortex mixer for 1 minute at 2500 rpm, thus obtaining a 1% (w/v) adjuvant solution in PBS, pH~6. The rH5-*E. coli* preparation was added to the prepared PROTASAN solution in 1:1 ratio (v/v), followed by shaking the mixture on a vortex mixer at 2500 rpm for 5 minutes. The vaccine composition with pH-6.5, comprising the antigen and 0.5% (w/v) PROTASAN™ UP G 113, was prepared directly before performing the vaccinations.

Immunization studies were done in a group of 15 laying-type Rossa 1 breed chickens (group no. 5) under production rearing conditions. The control group (K) was composed of 15 non-immunized chickens. The first vaccination was performed in the 3' week of animal life by subcutaneous administration of 25 μg of rH5-*E. coli* with aluminium hydroxide in three areas on the back of the neck in volume of 200 In the 7th week of life, i.e. 4 weeks after administering the I dose, intranasal vaccination of the animals was performed by administering 25 μg of rH5-*E. coli* with PROTASAN in volume of 272 IA, interchangeably to the left and right nostril. In order to monitor chicken response to immunization, blood was collected from vaccinated animals directly before administering the booster dose and within one month after administering the II antigen dose at one-week intervals. Samples collected in parallel from non-vaccinated chickens were the control material. Serum samples were prepared and stored as described in example 6. The schedule for immunizations and blood collection from vaccinated and control animals was according to regimen E (FIG. 35).

Analysis of Chicken Immune Response Using Serological Studies

Sera prepared during the experiment were analyzed using tests detecting antibodies against H5 AIV: the indirect and the competitive ELISAs (H5-ELISA; FLUAc H5 IDVet) and the hemagglutination inhibition (HI) test. The tests were conducted in order to investigate chicken humoral response to vaccination by administering a subcutaneous priming dose and an intranasal booster dose. The H5-ELISA test allowed to determine antigen-specific IgY antibodies, whereas the FLUAc H5 and HI tests allowed to evaluate functional properties of induced antibodies.

The H5-ELISA was performed as described in example 7, but the endpoint titer was determined for selected samples collected from individual animals. The method of calculating the cut-off value for H5-positive serum samples and the definition of the endpoint titer were shown in example 7. The FLUAc H5 test was done according to the manufacturer's (IDVet) instruction, applying the conditions increasing the test sensitivity (serum samples diluted 1:1, incubated on plates for 1 hour at temperature of 37° C.). The method of calculating competition levels and of interpretation of the results, according to the manufacturer's data, is described in example 7. The HI test was conducted with SPF chicken erythrocytes, using the heterologous LPAIV H5N2 as an antigen and hemagglutination inhibition unit (HIU) of 1:8. The principle of the HI test and the method of conducting it are shown in example 8. Assays were done on serum samples from all blood collections. Samples were considered positive if they reached the titer of at least 1:8.

Results of Serological Studies

Serological studies of chickens after subcutaneous priming immunization using 25 μs of rH5-*E. coli* and aluminium hydroxide as an adjuvant, conducted using the H5-ELISA on samples collected directly before administering the II antigen dose, i.e. 4 weeks after the first chicken vaccination, demonstrated the presence of anti-H5 IgY antibodies in 200-fold diluted sera from 13 out of 15 (87%) immunized animals. After intranasal administration of the vaccine comprising 20 μs of rH5-*E. coli* and PROTASAN™ UP G 113 as an adjuvant, in 10 out of 15 vaccinated animals an increase of serum antibody levels was observed, typical for secondary immune response (FIG. 29). Response level in the vaccinated group after administration of the II antigen varied, so that in 7 out of 10 chickens enhanced response was shown in samples diluted 200-fold, whereas in the other 3 chickens in samples diluted 800-fold. In most chickens that reacted positively to intranasal vaccination, the anti-H5 antibody level reached maximum value 1 week (9/10), exceptionally 2 weeks (1/10) after second immunization. Further analyses of the samples containing the highest level for individual animals of anti-H5 IgY antibodies after intranasal immunization, demonstrated that in 6 out of 10 chickens the endpoint titer for antibodies reached high values exceeding 1:10 000 and was within the range of 1:11 200-1:80 600.

Analyses of sera obtained from chickens 4 weeks after subcutaneous administration of priming dose of antigen using the FLUAc H5 test demonstrated that none of the studied samples was seropositive according to the classification criteria of the test and that competition values are within the range of 49-93% (FIG. 30). The decrease of the % competition value in serum samples after administration of the intranasal booster dose was observed only in the group of 10 chickens, wherein an increase of anti-H5 antibody levels was found after the intranasal vaccination, demonstrated with the H5-ELISA (FIG. 29, FIG. 30). In 5 out of 10 animals in this group, a decrease of the % competition value was observed after intranasal vaccination, the strongest being 1 week after this vaccination, wherein results obtained for 2 chickens determined them as seropositive (FIG. 30). The appearance of functional antibodies against H5 in serum or the increase of level thereof after intranasal administration of the antigen were also observed in the HI test in 4 out of 10 chickens reacting to the intranasal vaccination with the production of anti-H5 IgY-antibodies, detected with the H5-ELISA—(FIG. 29, Tab. 10).

TABLE 10

| | HI AIV | | | | |
|---|---|---|---|---|---|
| | After the I rH5 dose- s.c. | After the II rH5 dose - i.n. | | | |
| ID | 4 weeks H5N2 LP | 1 week H5N2 LP | 2 weeks H5N2 LP | 3 weeks H5N2 LP | 4 weeks H5N2 LP |
| 5-2 | <8 | <8 | <8 | <8 | <8 |
| 5-4 | <8 | <8 | <8 | <8 | <8 |
| 5-7 | <8 | <8 | <8 | <8 | <8 |
| 5-8 | <8 | <8 | <8 | <8 | <8 |
| 5-9 | <8 | 8 | 16 | <8 | <8 |
| 5-10 | 8 | <8 | <8 | <8 | <8 |
| 5-11 | <8 | <8 | <8 | <8 | <8 |
| 5-12 | <8 | 16 | <8 | <8 | <8 |
| 5-14 | 8 | 16 | <8 | 8 | <8 |
| 5-15 | 8 | 8 | 8 | 16 | na. |
| Seropositive | 3/10 (30%) | 4/10 (40%) | 2/10 (20%) | 1/10 (10%) | 0/9 (0%) |
| HI titer | 8 | 8-16 | 8-16 | 16 | <8 |

All of the conducted serological tests demonstrated a considerable variation in animal response to intranasal immunization, which was most probably caused by the observed partial swallowing of the vaccine by chickens when it was administered in too large volumes (272 μl).

Summary

Analyses of humoral response of laying-type Rossa 1 breed chickens to intranasal administration of the booster dose, comprising 20 μg of rH5-*E. coli* and PROTASAN™ UP G 113 (NovaMatrix/FMC Corp.) as an adjuvant, conducted using serological tests (H5-ELISA, FLUAc H5, HI-H5N2) suggest that:
  boosting immune response intranasally in chickens using the protein antigen—rH5-*E. coli* in the applied vaccine composition is possible,
  the developed vaccine has the potential to induce a high titer of antigen-specific IgY antibodies and functional antibodies against H5, such as antibodies competing with the FLUAc H5 test antibodies for a presumably conformational neutralizing epitope of H5 serotype AI viruses and antibodies inhibiting hemagglutination by the heterologous AIV H5N2.

REFERENCES

Avian Influenza in: OIE Manual of Diagnostic Tests and Vaccines for Terrestrial Animals 2012 [http://www.oie.int/international-standard-setting/terrestrial-manual/access-online/]

Aguilar-Yáñez J M, Portillo-Lara R, Mendoza-Ochoa G I, García-Echauri S A, López-Pacheco F, Bulnes-Abundis D, Salgado-Gallegos J, Lara-Mayorga I M, Webb-Vargas Y, León-Angel F O, Rivero-Aranda R E, Oropeza-Almazán Y, Ruiz-Palacios G M, Zertuche-Guerra M I, DuBois R M, White S W, Schultz-Cherry S, Russell C J, Alvarez M M. An influenza A/H1N1/2009 hemagglutinin vaccine produced in *Escherichia coli*. PLoS One. 2010; 5:e11694.

Biesova Z, Miller M A, Schneerson R, Shiloach J, Green K Y, Robbins J B, Keith J M. Preparation, characterization, and immunogenicity in mice of a recombinant influenza H5 hemagglutinin vaccine against the avian H5N1 A/Vietnam/1203/2004 influenza virus. Vaccine. 2009; 27:6234-8.

Bommakanti G, Citron M P, Hepler R W, Callahan C, Heidecker G J, Najar T A, Lu X, Joyce J G, Shiver J W, Casimiro D R, ter Meulen J, Liang X, Varadarajan R. Design of an HA2-based *Escherichia coli* expressed influenza immunogen that protects mice from pathogenic challenge. Proc Natl Acad Sci USA. 2010; 107:13701-6.

Bommakanti G, Lu X, Citron M P, Najar T A, Heidecker G J, ter Meulen J, Varadarajan R, Liang X. Design of *Escherichia coli*-expressed stalk domain immunogens of H1N1 hemagglutinin that protect mice from lethal challenge. J Virol. 2012; 86:13434-44.

Bosch B J, Bodewes R, de Vries R P, Kreijtz J H, Bartelink W, van Amerongen G, Rimmelzwaan G F, de Haan C A, Osterhaus A D, Rottier P J. Recombinant soluble, multimeric HA and NA exhibit distinctive types of protection against pandemic swine-origin 2009 A(H1N1) influenza virus infection in ferrets. J Virol. 2010; 84:10366-74.

Bradford M M. A rapid and sensitive method for the quantitation of microgram quantities of protein utilizing the principle of protein-dye binding. Anal Biochem. 1976; 72:248-54.

Chiu F F, Venkatesan N, Wu C R, Chou A H, Chen H W, Lian S P, Liu S J, Huang C C, Lian W C, Chong P, Leng C H. Immunological study of HA1 domain of hemagglutinin of influenza H5N1 virus. Biochem Biophys Res Commun. 2009; 383:27-31.

Chung C T, Miller R H. A rapid and convenient method for preparation and storage of competent bacterial cells. Nucleic Acids Res. 1988; 16:3580.

DuBois R M, Aguilar-Yáñez J M, Mendoza-Ochoa G I, Oropeza-Almazán Y, Schultz-Cherry S, Alvarez M M, White S W, Russell C J. The receptor-binding domain of influenza virus hemagglutinin produced in *Escherichia coli* folds into its native, immunogenic structure. J Virol. 2011; 85:865-72.

Ekiert D C, Bhabha G, Elsliger M A, Friesen R H, Jongeneelen M, Throsby M, Goudsmit J, Wilson I A. Antibody recognition of a highly conserved influenza virus epitope. Science. 2009; 324:246-51.

Gromadzka B, Smietanka K, Dragun J, Minta Z, Gora-Sochacka A, Szewczyk B. Detection of changes in avian influenza genome fragments by multitemperature single-strand conformational polymorphism. Mol Cell Probes. 2008; 22:301-4.

Hong M, Lee P S, Hoffman R M, Zhu X, Krause J C, Laursen N S, Yoon S I, Song L, Tussey L, Crowe J E Jr, Ward A B, Wilson I A. Antibody recognition of the pandemic H1N1 Influenza virus hemagglutinin receptor binding site. J Virol. 2013; 87:12471-80.

Horthongkham N, Srihtrakul T, Athipanyasilp N, Siritantikorn S, Kantakamalakul W, Poovorawan Y, Sutthent R. Specific antibody response of mice after immunization with COS-7 cell derived avian influenza virus (H5N1) recombinant proteins. J Immune Based Ther Vaccines. 2007; 5:10.

Jegerlehner A, Zabel F, Langer A, Dietmeier K, Jennings G T, Saudan P, Bachmann M F. Bacterially produced recombinant influenza vaccines based on virus-like particles. PLoS One. 2013; 8:e78947.

Jeon S H, Arnon R. Immunization with influenza virus hemagglutinin globular region containing the receptor-binding pocket. Viral Immunol. 2002; 15:165-76.

Khurana S, Chearwae W, Castellino F, Manischewitz J, King L R, Honorkiewicz A, Rock M T, Edwards K M, Del Giudice G, Rappuoli R, Golding H. Vaccines with MF59 adjuvant expand the antibody repertoire to target protective sites of pandemic avian H5N1 influenza virus. Sci Transl Med. 2010; 2:15ra5.

Khurana S, Verma S, Verma N, Crevar C J, Carter D M, Manischewitz J, King L R, Ross T M, Golding H. Properly folded bacterially expressed H1N1 hemagglutinin globular head and ectodomain vaccines protect ferrets against H1N1 pandemic influenza virus. PLoS One. 2010; 5:e11548.

Khurana S, Larkin C, Verma S, Joshi M B, Fontana J, Steven A C, King L R, Manischewitz J, McCormick W, Gupta R K, Golding H. Recombinant HA1 produced in *E. coli* forms functional oligomers and generates strain-specific SRID potency antibodies for pandemic influenza vaccines. Vaccine. 2011; 29:5657-65.

Khurana S, Verma S, Verma N, Crevar C J, Carter D M, Manischewitz J, King L R, Ross T M, Golding H. Bacterial HA1 vaccine against pandemic H5N1 influenza virus: evidence of oligomerization, hemagglutination, and cross-protective immunity in ferrets. J Virol. 2011; 85:1246-56.

Koenen M E, Boonstra-Blom A G, Jeurissen S H. Immunological differences between layer- and broiler-type chickens. Vet Immunol Immunopathol. 2002; 89:47-56.

Laemmli U K. Cleavage of structural proteins during the assembly of the head of bacteriophage T4. Nature. 1970; 227:680-5.

Liu G, Song L, Reiserova L, Trivedi U, Li H, Liu X, Noah D, Hou F, Weaver B, Tussey L. Flagellin-HA vaccines protect ferrets and mice against H5N1 highly pathogenic avian influenza virus (HPAIV) infections. Vaccine. 2012; 30:6833-8.

Liu G, Tarbet B, Song L, Reiserova L, Weaver B, Chen Y, Li H, Hou F, Liu X, Parent J, Umlauf S, Shaw A, Tussey L. Immunogenicity and efficacy of flagellin-fused vaccine candidates targeting 2009 pandemic H1N1 influenza in mice. PLoS One. 2011; 6:e20928.

Loeffen W L, de Vries R P, Stockhofe N, van Zoelen-Bos D, Maas R, Koch G, Moormann R J, Rottier P J, de Haan C A. Vaccination with a soluble recombinant hemagglutinin trimer protects pigs against a challenge with pandemic (H1N1) 2009 influenza virus. Vaccine. 2011; 29:1545-50.

Minta Z. 2008 HPAI-PLAN Instrukcje przeprowadzania laboratoryjnych badán diagnostycznych w kierunku grypy ptaków.

Okuno Y, Isegawa Y, Sasao F, Ueda S. A common neutralizing epitope conserved between the hemagglutinins of influenza A virus H1 and H2 strains. J Virol. 1993; 67:2552-8.

Sagawa H, Ohshima A, Kato I, Okuno Y, Isegawa Y. The immunological activity of a deletion mutant of influenza virus haemagglutinin lacking the globular region. J Gen Virol. 1996; 77:1483-7.

Sánchez-Arreola P B, López-Uriarte S, Marichal-Gallardo P A, González-Vázquez J C, Pérez-Chavarría R, Soto-Vázquez P, López-Pacheco F, Ramírez-Medrano A, Rocha-Pizaña M R, Alvarez M M. A baseline process for the production, recovery, and purification of bacterial influenza vaccine candidates. Biotechnol Prog. 2013; 29:896-908.

Shen S, Mahadevappa G, Oh H L, Wee B Y, Choi Y W, Hwang L A, Lim S G, Hong W, Lal S K, Tan Y J. Comparing the antibody responses against recombinant hemagglutinin proteins of avian influenza A (H5N1) virus expressed in insect cells and bacteria. J Med Virol. 2008; 80:1972-83.

Skibinski D A, Hanson B J, Lin Y, von Messling V, Jegerlehner A, Tee J B, Chye de H, Wong S K, Ng A A, Lee H Y, Au B, Lee B T, Santoso L, Poidinger M, Fairhurst A M, Matter A, Bachmann M F, Saudan P, Connolly J E Enhanced neutralizing antibody titers and Th1 polarization from a novel *Escherichia coli* derived pandemic influenza vaccine. PLoS One. 2013; 8:e76571.

Song L, Nakaar V, Kavita U, Price A, Huleatt J, Tang J, Jacobs A, Liu G, Huang Y, Desai P, Maksymiuk G, Takahashi V, Umlauf S, Reiserova L, Bell R, Li H, Zhang Y, McDonald W F, Powell T J, Tussey L. Efficacious recombinant influenza vaccines produced by high yield bacterial expression: a solution to global pandemic and seasonal needs. PLoS One. 2008; 3:e2257.

Song L, Zhang Y, Yun N E, Poussard A L, Smith J N, Smith J K, Borisevich V, Linde J J, Zacks M A, Li H, Kavita U, Reiserova L, Liu X, Dumuren K, Balasubramanian B, Weaver B, Parent J, Umlauf S, Liu G, Huleatt J, Tussey L, Paessler S. Superior efficacy of a recombinant flagellin: H5N1 HA globular head vaccine is determined by the placement of the globular head within flagellin. Vaccine. 2009; 27:5875-84.

Spackman E, Senne D A, Myers T J, Bulaga L L, Garber L P, Perdue M L, Lohman K, Daum L T, Suarez D L. Development of a real-time reverse transcriptase PCR assay for type A influenza virus and the avian H5 and H7 hemagglutinin subtypes. J Clin Microbiol. 2002; 40:3256-60.

Steel J, Lowen A C, Wang T T, Yondola M, Gao Q, Haye K, Garcia-Sastre A, Palese P. Influenza virus vaccine based on the conserved hemagglutinin stalk domain. M Bio. 2010; 1(1).

Suarez D L. Overview of avian influenza DIVA test strategies. Biologicals. 2005; 33:221-6. Sui J, Hwang W C, Perez S, Wei G, Aird D, Chen L M, Santelli E, Stec B, Cadwell G, Ali M, Wan H, Murakami A, Yammanuru A, Han T, Cox N J, Bankston L A, Donis R O, Liddington R C, Marasco W A. Structural and functional bases for broad-spectrum neutralization of avian and human influenza A viruses. Nat Struct Mol Biol. 2009; 16:265-73.

Taylor D N, Treanor J J, Sheldon E A, Johnson C, Umlauf S, Song L, Kavita U, Liu G, Tussey L, Ozer K, Hofstaetter T, Shaw A. Development of VAX128, a recombinant hemagglutinin (HA) influenza-flagellin fusion vaccine with improved safety and immune response. Vaccine. 2012 30:5761-9.

Taylor D N, Treanor J J, Strout C, Johnson C, Fitzgerald T, Kavita U, Ozer K, Tussey L, Shaw A. Induction of a potent immune response in the elderly using the TLR-5 agonist, flagellin, with a recombinant hemagglutinin influenza-flagellin fusion vaccine (VAX125, STF2.HA1 SI). Vaccine. 2011 29: 4897-902.

Treanor J J, Taylor D N, Tussey L, Hay C, Nolan C, Fitzgerald T, Liu G, Kavita U, Song L, Dark I, Shaw A. Safety and immunogenicity of a recombinant hemagglutinin influenza-flagellin fusion vaccine (VAX125) in healthy young adults. Vaccine. 2010; 28:8268-74.

van den Berg T, Lambrecht B, Marché S, Steensels M, Van Borm S, Bublot M. Influenza vaccines and vaccination strategies in birds. Comp Immunol MicrobiolInfect Dis. 2008; 31:121-65.

Verma S, Dimitrova M, Munjal A, Fontana J, Crevar C J, Carter D M, Ross T M, Khurana S, Golding H. Oligomeric recombinant H5 HA1 vaccine produced in bacteria protects ferrets from homologous and heterologous wild-type H5N1 influenza challenge and controls viral loads better than subunit H5N1 vaccine by eliciting high-affinity antibodies. J Virol. 2012; 86:12283-93.

Wei C J, Xu L, Kong W P, Shi W, Canis K, Stevens J, Yang Z Y, Dell A, Haslam S M, Wilson I A, Nabel G J. Comparative efficacy of neutralizing antibodies elicited by recombinant hemagglutinin proteins from avian H5N1 influenza virus. J Virol. 2008; 82:6200-8.

Weldon W C, Wang B Z, Martin M P, Koutsonanos D G, Skountzou I, Compans R W Enhanced immunogenicity of stabilized trimeric soluble influenza hemagglutinin. PLoS One. 2010; 5:e12466 Wiley D C, Wilson I A, Skehel J J. Structural identification of the antibody-binding sites of Hong Kong influenza haemagglutinin and their involvement in antigenic variation. Nature. 1981; 289:373-8.

Wilson I A, Cox N J. Structural basis of immune recognition of influenza virus hemagglutinin. Annu Rev Immunol. 1990; 8:737-71.

Xie Q M, Ji J, Du L Q, Cao Y C, Wei L, Xue C Y, Qin J P, Ma J Y, Bi Y Z. Preparation and immune activity analysis of H5N1 subtype avian influenza virus recombinant protein-based vaccine. Poult Sci. 2009; 88:1608-15.

Xuan C, Shi Y, Qi J, Zhang W, Xiao H, Gao G F. Structural vaccinology: structure-based design of influenza A virus hemagglutinin subtype-specific subunit vaccines. Protein Cell. 2011; 2:997-1005.

---

The invention claimed is:

1. A recombinant influenza virus (IV) hemagglutinin (HA) polypeptide consisting of:
   - a HA-1 subunit, forming the viral HA globular domain with a protein binding site for the host cells receptors and involved in the formation of the native HA stalk domain; and
   - a HA-2 subunit fragment with an N-terminal fusion peptide, forming the native HA stalk domain, wherein the HA-2 subunit fragment is fused directly to the HA-1 subunit,
   - wherein the recombinant polypeptide lacks a polybasic cleavage site between the HA-1 subunit and the HA-2 subunit fragment,
   - wherein the recombinant polypeptide lacks a N-terminal signal peptide,
   - wherein the C-terminal protein region of the recombinant polypeptide is truncated downstream of the bromelain cleavage site on the HA-2 subunit fragment,
   - wherein the transmembrane and cytoplasmic domains downstream of the bromelain cleavage site on the HA-2 subunit fragment of the IV HA polypeptide are not present in the recombinant polypeptide, and
   - wherein the recombinant polypeptide is not glycosylated.

2. The polypeptide according to claim 1, wherein the influenza virus is highly-pathogenic avian influenza virus (HPAIV) H5N1.

3. The polypeptide according to claim 2, wherein the influenza virus is the HPAIV H5N1 A/swan/Poland/305-135V08/2006 strain.

4. The polypeptide according to claim 1, wherein the HA-1 subunit consists of amino acids 1-324 of SEQ ID NO: 1 and the HA-2 subunit fragment consists of amino acids 331-506 of SEQ ID NO: 1.

5. The recombinant polypeptide according to claim 1, wherein the recombinant polypeptide structurally corresponds to the amino acids 17-340 and 347-522 of the HA from the H5N1 strain of the avian influenza virus (AIV) A/swan/Poland/305-135V08/2006.

6. The recombinant polypeptide according to claim 1, wherein the recombinant polypeptide has an amino acid sequence identical to SEQ ID NO: 2.

7. The recombinant polypeptide according to claim 1, wherein the recombinant polypeptide is produced in a prokaryotic expression system.

8. The recombinant polypeptide according to claim 7, wherein the prokaryotic expression system is E. coli.

9. The polypeptide according to claim 7, wherein the recombinant polypeptide is expressed in the form of inclusion bodies in the prokaryotic expression system.

10. A formulation comprising:
    a carrier; and
    the polypeptide as defined in claim 1 in an effective amount to elicit immune response or treat an influenza virus infection.

11. The formulation according to claim 10, wherein the carrier is an adjuvant capable of stimulating a humoral-immune response or a cellular immune response, and wherein the carrier is selected from the group consisting of: mineral salts, oil emulsions, mycobacterial products, saponins, synthetic products and cytokines.

12. The formulation according to claim 11, wherein the adjuvant is aluminum hydroxide, chitosan salts, an adjuvant comprising saponin, an adjuvant comprising a water soluble deacetylated chitosan glutamate, an adjuvant comprising an oil-in-water emulsion with a detergent surfactant, and squalene, an adjuvant comprising squalene, and an adjuvant comprising saponin, cholesterol/DPPC in detergent, and a buffer.

13. The formulation according to claim 10, wherein the formulation is formulated for subcutaneous, intradermal, intramuscular, mucosal, conjunctival, naso-conjunctival, intranasal, or gastrointestinal administration to a subject.

14. The formulation as defined in claim 10, wherein the formulation is formulated for use in prophylactic vaccination of humans or for immunization of birds against influenza virus.

15. The formulation of claim 10, wherein the influenza virus is the highly pathogenic avian influenza virus H5N1 strain.

* * * * *